(12) United States Patent
Lee et al.

(10) Patent No.: US 11,832,962 B2
(45) Date of Patent: Dec. 5, 2023

(54) METHOD FOR DETERMINING WHETHER MEDICATION HAS BEEN ADMINISTERED AND SERVER USING SAME

(71) Applicant: INHANDPLUS INC., Pohang-si (KR)

(72) Inventors: Hwiwon Lee, Seoul (KR); Sang Pil Yoo, Seoul (KR)

(73) Assignee: INHANDPLUS INC., Pohang-si (KR)

( * ) Notice: Subject to any disclaimer, the term of this patent is extended or adjusted under 35 U.S.C. 154(b) by 0 days.

(21) Appl. No.: 17/883,635

(22) Filed: Aug. 9, 2022

(65) Prior Publication Data

US 2022/0384029 A1    Dec. 1, 2022

Related U.S. Application Data

(63) Continuation of application No. 17/356,528, filed on Jun. 24, 2021, now Pat. No. 11,457,862.

(30) Foreign Application Priority Data

Aug. 19, 2020  (KR) .................. 10-2020-0103633
Nov. 4, 2020   (KR) .................. 10-2020-0146394
(Continued)

(51) Int. Cl.
*G06K 9/00*    (2022.01)
*A61B 5/00*    (2006.01)
(Continued)

(52) U.S. Cl.
CPC ........ *A61B 5/4833* (2013.01); *G06F 18/2148* (2023.01); *G06N 20/00* (2019.01);
(Continued)

(58) Field of Classification Search
None
See application file for complete search history.

(56) References Cited

U.S. PATENT DOCUMENTS 10,025,908 B1   7/2018  Orellano et al.
2013/0245389 A1* 9/2013 Schultz ............... A61B 5/0002
                                                600/301
(Continued)

FOREIGN PATENT DOCUMENTS

JP    2004-280376 A    10/2004
JP    2015-126451 A    7/2015
(Continued)

OTHER PUBLICATIONS

International Search Report of PCT/KR2019/001118 dated May 8, 2019.
(Continued)

*Primary Examiner* — Wei Wen Yang
(74) *Attorney, Agent, or Firm* — Revolution IP, PLLC

(57) ABSTRACT

Provided is a server for determining whether medication has been administered, the server including: a transceiver receiving a video recorded by a wearable device; a memory storing a detection model and a confirmation model, wherein the detection model is trained to output whether each of preset targets appears in an image, and the confirmation model is trained to output whether medication has been administered, wherein the preset targets include an object related to a medicine or a medicine container and a posture related to medication administration; and one or more processors configured to detect the preset targets by inputting image frames of the video to the detection model and to determine whether medication has been administered by inputting confirmation model input data to the confirmation model, the confirmation model input data generated based on a detection result of the detection model.

10 Claims, 44 Drawing Sheets

(30) Foreign Application Priority Data

Jan. 4, 2021 (KR) ........................ 10-2021-0000496
Mar. 30, 2021 (KR) ........................ 10-2021-0040853

(51) Int. Cl.

| | |
|---|---|
| G06T 7/20 | (2017.01) |
| H04W 76/10 | (2018.01) |
| G08C 17/02 | (2006.01) |
| G06T 7/246 | (2017.01) |
| G16H 50/20 | (2018.01) |
| G16H 20/10 | (2018.01) |
| G06N 20/00 | (2019.01) |
| G06V 20/40 | (2022.01) |
| G06V 10/94 | (2022.01) |
| G06V 40/20 | (2022.01) |
| H04N 5/765 | (2006.01) |
| G16H 40/63 | (2018.01) |
| G06F 18/214 | (2023.01) |

(52) U.S. Cl.

CPC ................ *G06T 7/20* (2013.01); *G06T 7/251* (2017.01); *G06V 10/95* (2022.01); *G06V 20/41* (2022.01); *G06V 40/20* (2022.01); *G08C 17/02* (2013.01); *G16H 20/10* (2018.01); *G16H 40/63* (2018.01); *G16H 50/20* (2018.01); *H04N 5/765* (2013.01); *H04W 76/10* (2018.02); *G06T 2207/10016* (2013.01); *G06T 2207/20081* (2013.01); *G06T 2207/30196* (2013.01); *G06V 2201/03* (2022.01)

(56) References Cited

U.S. PATENT DOCUMENTS

| | | | |
|---|---|---|---|
| 2015/0215443 | A1 | 7/2015 | Heo et al. |
| 2015/0216413 | A1 | 8/2015 | Soyao et al. |
| 2015/0363570 | A1 | 12/2015 | Hanina et al. |
| 2016/0027284 | A1 | 1/2016 | Kamp et al. |
| 2016/0287166 | A1 | 10/2016 | Tran |
| 2016/0306932 | A1 | 10/2016 | Fateh et al. |
| 2016/0354283 | A1 | 12/2016 | Cho et al. |
| 2017/0004283 | A1 | 1/2017 | Lewis |
| 2017/0111565 | A1 | 4/2017 | Shibahara et al. |
| 2018/0132783 | A1 | 5/2018 | Wang et al. |
| 2019/0065970 | A1 | 2/2019 | Bonutti et al. |
| 2019/0385717 | A1 | 12/2019 | Guan et al. |
| 2021/0058590 | A1 | 2/2021 | Lee |

FOREIGN PATENT DOCUMENTS

| | | |
|---|---|---|
| JP | 2015-197803 A | 11/2015 |
| JP | 2016-091567 A | 5/2016 |
| JP | 2017-169732 A | 9/2017 |
| JP | 2019-213886 A | 12/2019 |
| KR | 10-2015-0088599 A | 8/2015 |
| KR | 10-2016-0008448 A | 1/2016 |
| KR | 10-2016-0099435 A | 8/2016 |
| KR | 10-2016-0104288 A | 9/2016 |
| KR | 10-2016-0108051 A | 9/2016 |
| KR | 10-2016-0120131 A | 10/2016 |
| KR | 10-2017-0054861 A | 5/2017 |
| KR | 10-2017-0084657 A | 7/2017 |
| KR | 10-2017-0112704 A | 10/2017 |
| KR | 10-1798890 B1 | 11/2017 |
| KR | 10-2018-0028701 A | 3/2018 |
| KR | 10-2018-0054453 A | 5/2018 |
| KR | 10-2018-0084576 A | 7/2018 |
| KR | 10-1949102 B1 | 2/2019 |
| KR | 10-2019-0067686 A | 6/2019 |
| KR | 10-2019-0125143 A | 11/2019 |
| KR | 10-2019-0126773 A | 11/2019 |
| KR | 10-2020-0080047 A | 7/2020 |

OTHER PUBLICATIONS

Written opinion of PCT/KR2019/001118 dated May 8, 2019.
International Search Report of PCT/KR2020/006008 dated Aug. 24, 2020.
Written opinion of PCT/KR2020/006008 dated Aug. 24, 2020.
Office Action of KR Application No. 10-2019-7023063 dated Feb. 6, 2020.
Office Action of KR Application No. 10-2019-7023063 dated Apr. 17, 2020.
Office Action of KR Application No. 10-2019-7023063 dated Sep. 1, 2020.
Notice of Allowance of KR Application No. 10-2019-7023063 dated Sep. 28, 2020.
Office Action of KR Application No. 10-2020-7029786 dated Feb. 5, 2021.
Office Action of KR Application No. 10-2021-0040855 dated Jun. 14, 2021.
Office Action of KR Application No. 10-2021-0039622 dated Jun. 17, 2021.
Office Action of KR Application No. 10-2021-0040853 dated Jun. 23, 2021.
Office Action of KR Application No. 10-2021-0040854 dated Jun. 23, 2021.
Office Action of Korean Patent Application No. 10-2020-7013576 dated Jun. 30, 2021.
Notice of Allowance of U.S. Appl. No. 17/358,116 dated Nov. 8, 2021.
Non-Final Office Action of U.S. Appl. No. 17/051,436 dated Dec. 7, 2021.
International Search Report of PCT/KR2021/011033 dated Dec. 7, 2021.
Written Opinion of PCT/KR2021/011033 dated Dec. 7, 2021.
International Search Report of PCT/KR2021/011057 dated Dec. 7, 2021.
Written Opinion of PCT/KR2021/011057 dated Dec. 7, 2021.
Haik Kalantarian et al. "A Wearable Sensor System for Medication Adherence Prediction", Artificial Intelligence in Medicine, May 2016, vol. 69, pp. 43-52.
Non-Final Office Action of U.S. Appl. No. 17/518,615 dated Jan. 13, 2022.
Office Action of KR Application No. 10-2021-0186342 dated Jan. 19, 2022.
Office Action of JP Application No. 2020-560911 dated Feb. 1, 2022.

\* cited by examiner

FIG. 13
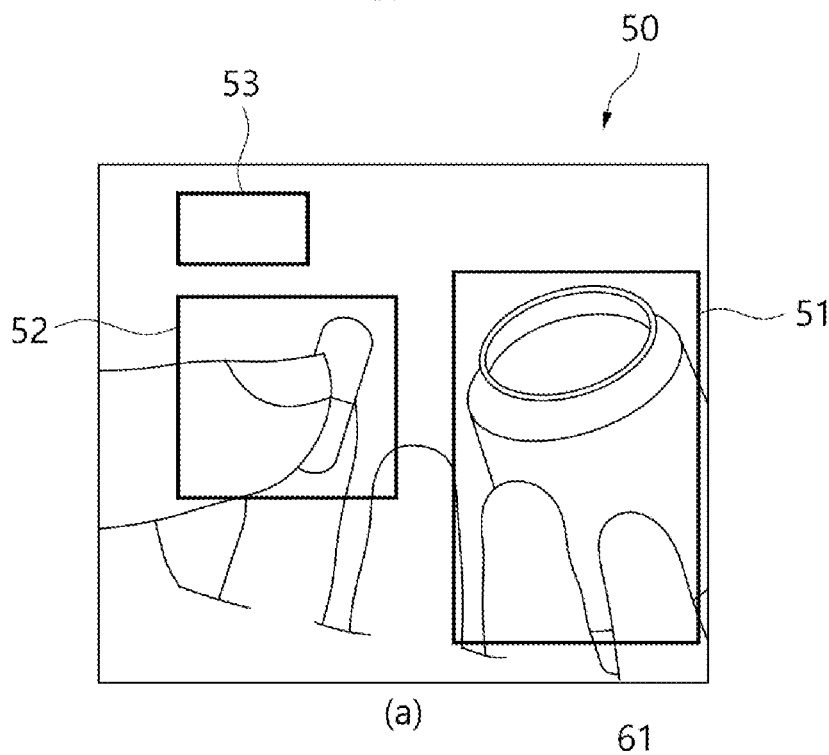
(a)
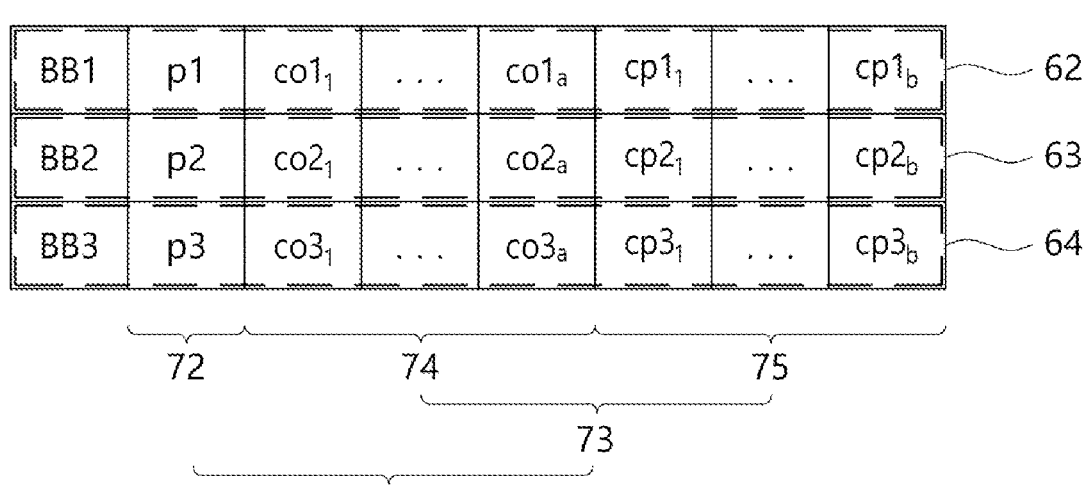
(b)

FIG. 29

| MODEL TYPE | ACCURACY |
|---|---|
| I3D | 77.8 ~ 81% |
| SlowFast | 74 ~ 80% |

FIG. 30

| VERSION | ACCURACY | |
| --- | --- | --- |
| | DETECTION MODEL | CONFIRMATION MODE |
| 1 | 85.1% | 90.5% |
| 2 | 88.8% | 94.5% |

FIG. 32

| MODEL TYPE | CATEGORY | ACCURACY | NOTE |
|---|---|---|---|
| MONITORING MODEL | MEDICINE BOTTLE | 60.1% | |
| | INHALER | | |
| | BLISTER PACK | | |
| CLASSIFICATION MODEL + MONITORING MODEL | MEDICINE BOTTLE | 77% | AVERAGE ACCURACY 79.8% |
| | INHALER | 78.4% | |
| | BLISTER PACK | 83.9% | |

FIG. 35

| DISTINGUISHING MAIN/SUB HANDS | VALIDATION ACCURACY | TEST ACCURACY |
|---|---|---|
| O | 98.8% | 96.8% |
| X | 97.7% | 88.8% |

FIG. 39

| DETECTION MODEL | CONFIRMATION MODEL | ENTIRE MEDICATION ADMINISTRATION PROCESS | OMITTING SOME OF MEDICATION ADMINISTRATION PROCESS |
|---|---|---|---|
| COMMON | 1 | 96.5% | 83.7% |
| | 2 | 99.8% | 95.8% |

FIG. 40

| CONFIRMATION MODEL | ENTIRE MEDICATION ADMINISTRATION PROCESS | OMITTING SOME OF MEDICATION ADMINISTRATION PROCESS |
|---|---|---|
| 3 | 98.9% | 93.1% |
| 4 | 99.3% | 90.0% |

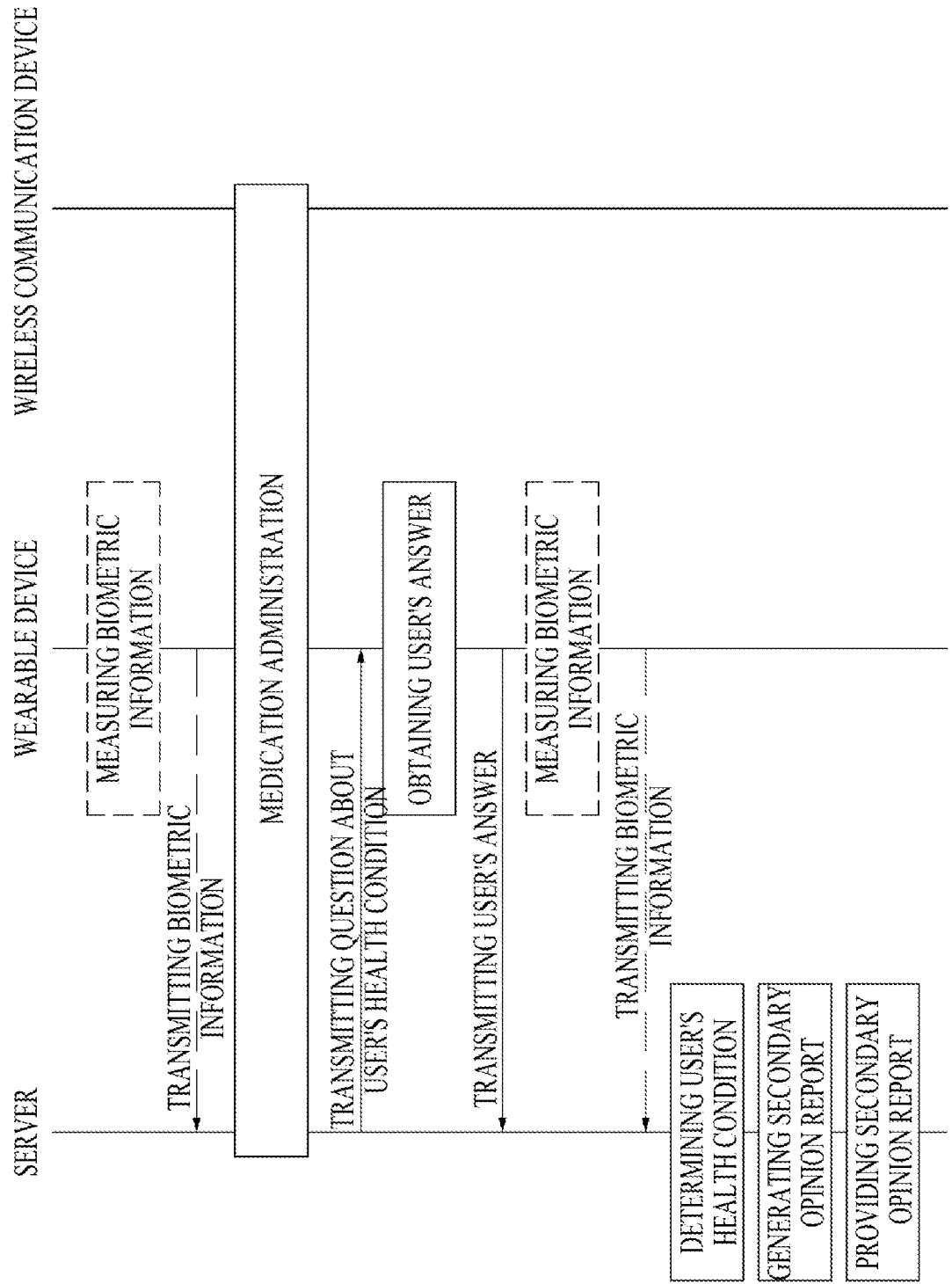

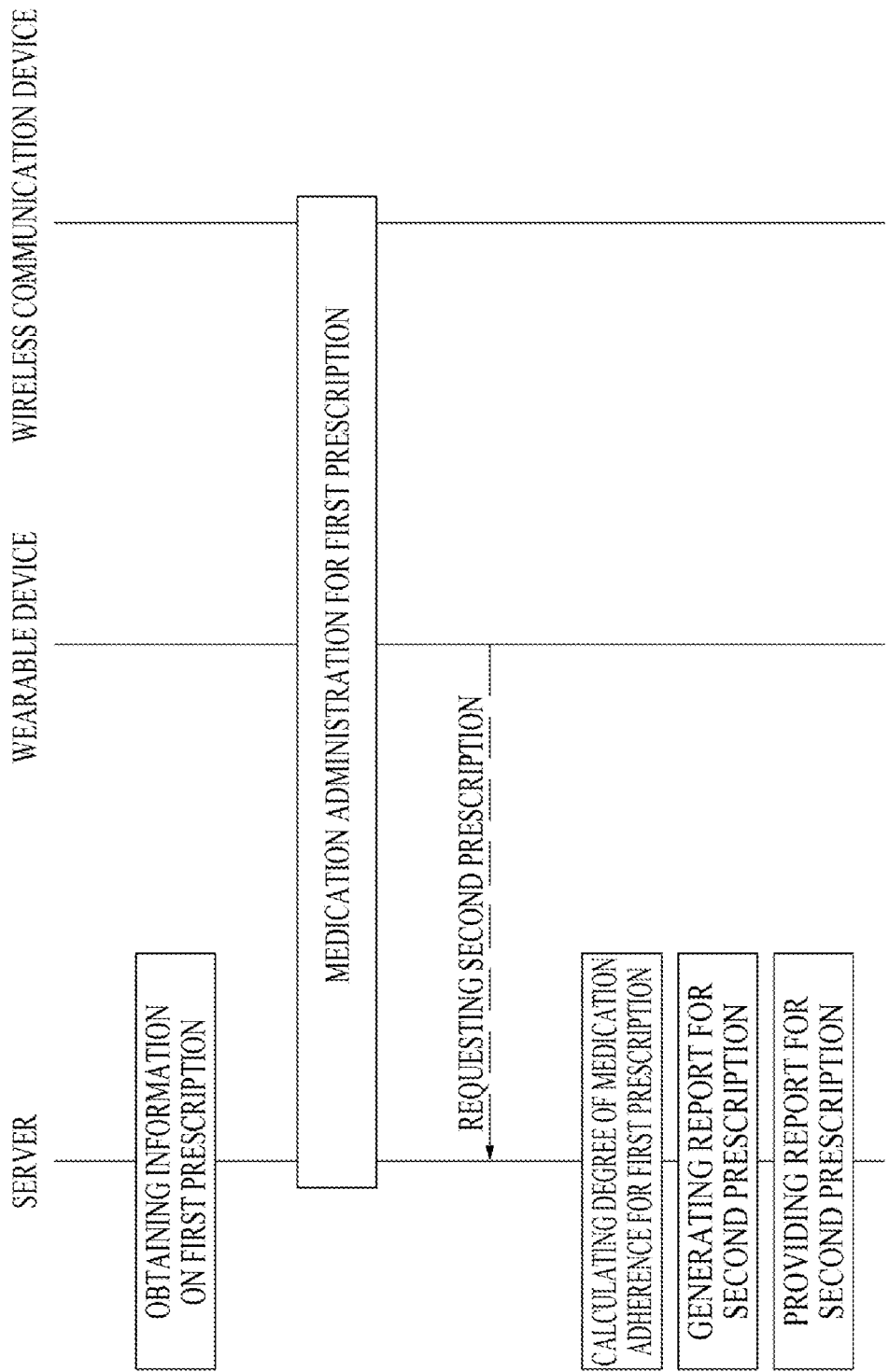

METHOD FOR DETERMINING WHETHER MEDICATION HAS BEEN ADMINISTERED AND SERVER USING SAME

CROSS REFERENCE TO RELATED APPLICATION

This application is a Continuation Application of U.S. patent application Ser. No. 17/356,528 filed on Jun. 24, 2021, which claims priority to Korean Patent Applications No. 10-2020-0103633, filed Aug. 19, 2020, No. 10-2020-0146394, filed Nov. 4, 2020, No. 10-2021-0000496, filed Jan. 4, 2021, and No. 10-2021-0040853, filed Mar. 30, 2021, the entire contents of which are incorporated herein for all purposes by this reference.

BACKGROUND OF THE INVENTION

Field of the Invention

The present disclosure relates to a method for determining whether medication has been administered, and a server using the method.

Description of the Related Art

There has been a constant interest in health care based on medical treatment and medical science from the past. Recently, as life expectancy increases with development of medical technology, such interest has further increased. Such health care needs to be performed regularly by a user himself/herself in daily life, for example, taking prescribed medicines in daily life, periodically injecting medicine into the body, measuring a health indicator using medical devices, and so on.

To enhance the effects of the above-described health care, it is necessary to induce or force the user to conduct behavior related to health care. To this end, there is a need for a solution for detecting a user's action related to health care in daily life and checking whether health care is well conducted.

In the meantime, in monitoring a user's behavior related to health care in the related art, the user's effort is required, for example, making a monitoring device operate before medication administration, recording the user's behavior himself/herself, and so on. Unfortunately, when a user forgets to do this, information related to health care is not collected.

Therefore, when considering user convenience and accuracy of health care, it is necessary to develop a solution for automatically monitoring the user's behavior for health care in daily life even without the user's effort.

The foregoing is intended merely to aid in the understanding of the background of the present disclosure, and is not intended to mean that the present disclosure falls within the purview of the related art that is already known to those skilled in the art.

SUMMARY OF THE INVENTION

The present disclosure is directed to providing a method for determining exactly whether medication has been administered, and a server using the method.

The present disclosure is directed to providing a method for determining whether medication has been administered using a video acquired by a wearable device, such as a smart watch, and a server using the method.

The present disclosure is directed to providing a method for handling various types of medication administration situations, and a server using the method.

Technical problems to be solved by the present disclosure are not limited to the aforementioned technical problems and other technical problems which are not mentioned will be clearly understood by those skilled in the art from the present disclosure and the accompanying drawings.

According to an embodiment, a server for determining whether medication has been administered, the server may comprising: a transceiver receiving a video recorded by a wearable device; a memory storing a detection model and a confirmation model, wherein the detection model is trained to output whether each of preset targets appears in an image, and the confirmation model is trained to output whether medication has been administered, wherein the preset targets include an object related to a medicine or a medicine container and a posture related to medication administration; and one or more processors configured to detect the preset targets by inputting image frames of the video to the detection model and to determine whether medication has been administered by inputting confirmation model input data to the confirmation model, the confirmation model input data generated based on a detection result of the detection model, wherein the posture may include at least one of a posture of holding a medicine container or a posture of taking a medicine.

According to an embodiment, a method, performed by one or more processors, for determining whether medication has been administered, the method may comprising: receiving a video recorded by a wearable device; detecting one or more preset targets by inputting image frames of the video to a detection model, wherein the detection model is trained to output whether each of the preset targets appears in an image, and wherein the preset targets include an object related to a medicine or a medicine container and a posture related to medication administration; and determining whether medication has been administered by inputting confirmation model input data generated based on a detection result of the detection model to the confirmation model, wherein the posture may include at least one of a posture of holding a medicine container or a posture of taking a medicine.

According to an embodiment, a method, performed by one or more processors, for training a detection model and a confirmation model to determine whether medication has been administered, the method may comprising: obtaining detection model training data including training images and detection model labels corresponding to the training images, wherein each of the detection model labels may have a class for a medicine or a medicine container and a class for a posture related to medication administration, and wherein the detection model labels may include a first detection model label corresponding to a first image of the training images, and a second detection model label corresponding to a second image of the training images; obtaining output data by inputting the training images to the detection model; updating the detection model by comparing the detection model labels and the output data of the detection model; obtaining confirmation model training data including confirmation model input data and a confirmation model label corresponding to the confirmation model input data, wherein the confirmation model label may include a label for determining whether medication has been administered, and wherein the confirmation model input data may be generated based on the output data of the detection model; obtaining output data by inputting the confirmation model input data to the confirmation model; and updating the confirmation model by comparing the confirmation model label and the output data of the confirmation model, wherein the posture may include at least one of a posture of holding a medicine container or a posture of taking a medicine.

Technical solutions in the present disclosure are not be limited to the above, and other not-mentioned technical solutions will be clearly understandable to those skilled in the art from the present disclosure and the accompanying drawings.

According to embodiments in the present disclosure, provided are the method for determining whether medication has been administered, and the server for using the method, wherein the method and the server are capable of improving the accuracy of determining whether medication has been administered, considering both medication-administration related postures and medication-administration related objects.

Effects of the present disclosure are not limited to the aforementioned effects, and other effects which are not described herein should be clearly understood by those skilled in the art from the present disclosure and the accompanying drawings.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 13 is a diagram illustrating an example of detection model output data;

FIG. 29 is a diagram illustrating a first embodiment that is an example of a method for determining whether medication has been administered using a monitoring model;

FIGS. 30 and 31 are diagrams illustrating a second embodiment that is an example of a method for determining whether medication has been administered using a detection model and a confirmation model;

FIG. 32 is a diagram illustrating a third embodiment that is an example of a method for determining whether medication has been administered using a classification model;

FIG. 35 is a diagram illustrating a result of determining whether medication has been administered, depending on whether medication administration mainly performed by a main hand and medication administration mainly performed by a sub hand are distinguished, according to an embodiment;

FIG. 39 is a diagram illustrating a model that is trained considering a situation in which some of a medication administration process is omitted, according to an embodiment;

FIG. 40 is a diagram illustrating removal of consecutive image frames and removal of random image frames according to an embodiment;

FIG. 43 is a diagram illustrating provision of a secondary opinion report as an example of application to telemedicine; and FIG. 44 is a diagram illustrating provision of a prescription report as another example to application of telemedicine.

DETAILED DESCRIPTION OF THE INVENTION

Figure 1:
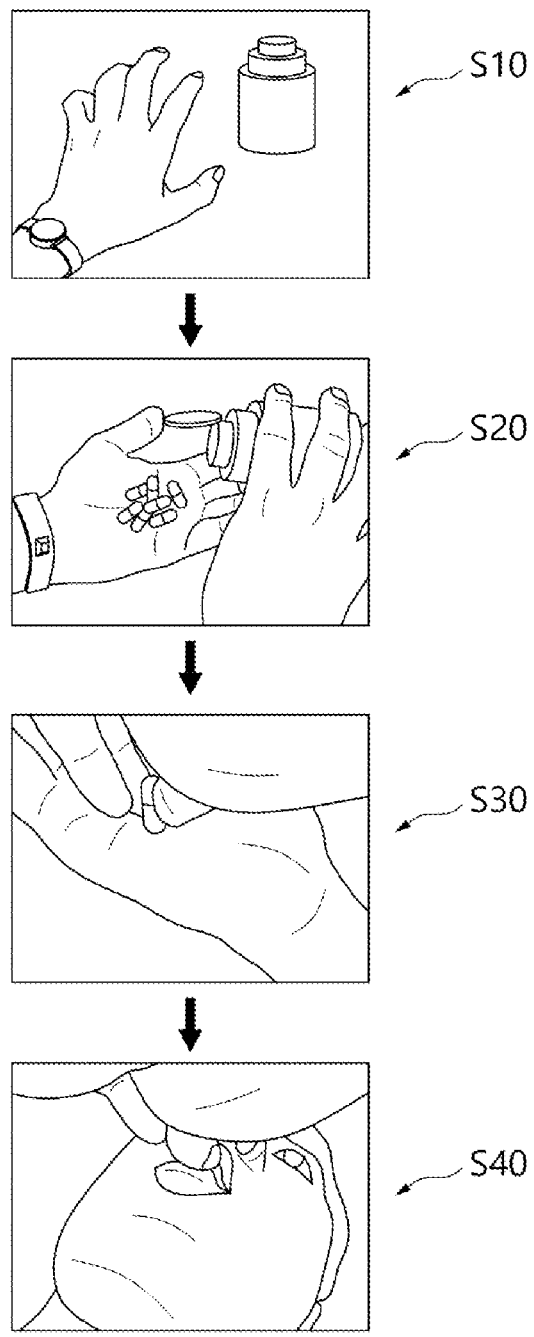
FIG. 1 is a diagram illustrating a medication administration process according to an embodiment.

Embodiments described in the present disclosure are intended to clearly describe the scope of the present disclosure to those having ordinary skill in the art to which the present disclosure pertains, and do not limit the present disclosure. It should be understood that the present disclosure includes modifications or variations within the scope of the present disclosure.

The terms used in the present disclosure are selected from general terms, which are widely used currently, considering functions of elements in the present disclosure, and may have meanings varying according to the intention of those skilled in the art, the custom in the art, or the advent of new technology. If a specific term is used with a specific meaning, the meaning of the term will be described specifically. Accordingly, the terms used in the present disclosure should not be interpreted as simple names of the terms, but be interpreted on the basis of the actual meanings of the terms and the whole context throughout the present disclosure.

The accompanying drawings of the present disclosure are to facilitate the description of the present disclosure and the shape in the drawings may be exaggerated to help understanding of the present disclosure, so the present disclosure is not limited to the drawings.

In the present disclosure, if it is determined that detailed descriptions of known configurations or functions related to the present disclosure make the gist of the present disclosure unclear, the detailed descriptions will be omitted when necessary.

According to an embodiment, a server for determining whether medication has been administered, the server may comprising: a transceiver receiving a video recorded by a wearable device; a memory storing a detection model and a confirmation model, wherein the detection model is trained to output whether each of preset targets appears in an image, and the confirmation model is trained to output whether medication has been administered, wherein the preset targets include an object related to a medicine or a medicine container and a posture related to medication administration; and one or more processors configured to detect the preset targets by inputting image frames of the video to the detection model and to determine whether medication has been administered by inputting confirmation model input data to the confirmation model, the confirmation model input data generated based on a detection result of the detection model, wherein the posture may include at least one of a posture of holding a medicine container or a posture of taking a medicine.

The detection result may include a plurality of detection model output data, each of the detection model output data corresponding to each of the image frames of the video, and wherein the one or more processors may be further configured to generate the confirmation model input data by synthesizing the plurality of detection model output data.

The confirmation model input data may be generated by arranging a plurality of the detection model output data in series of time information of the corresponding image frame.

The detection model may include an object detection model and a posture detection model, and wherein the one or more processors may be further configured to detect the object by inputting the image frames of the video to the object detection model and to detect the posture by inputting the image frames of the video to the posture detection model.

The detection model may include a first detection model for detecting one or more preset targets of a first type and a second detection model for detecting one or more preset targets of a second type, wherein the memory storing a classification model for classifying a category of the video, and wherein the one or more processors may be further configured to: define the category of the video using the video and the classification model; when the category of the video is defined to a first category corresponding to the first type, detect the preset targets by inputting the image frames of the video to the first detection model; and when the category of the video is defined to a second category corresponding to the second type, detect the preset targets by inputting the image frames of the video to the second detection model.

The confirmation model may include a first confirmation model corresponding to the first detection model and a second confirmation model corresponding to the second detection model, and wherein the one or more processors may be further configured to: when the category of the video is defined to the first category, determine whether medication has been administered by inputting the confirmation model input data to the first confirmation model; and when the category of the video is defined to the second category, determine whether medication has been administered by inputting the confirmation model input data to the second confirmation model.

The one or more processors may be further configured to: estimate a location of the preset targets in the image frames of the video so that the detection result and the confirmation model input data reflect the location of the preset targets; and determine whether medication has been administered considering the location of the preset targets.

According to an embodiment, a method, performed by one or more processors, for determining whether medication has been administered, the method may comprising: receiving a video recorded by a wearable device; detecting one or more preset targets by inputting image frames of the video to a detection model, wherein the detection model is trained to output whether each of the preset targets appears in an image, and wherein the preset targets include an object related to a medicine or a medicine container and a posture related to medication administration; and determining whether medication has been administered by inputting confirmation model input data generated based on a detection result of the detection model to the confirmation model, wherein the posture may include at least one of a posture of holding a medicine container or a posture of taking a medicine.

The detection result may include a plurality of detection model output data, each of the detection model output data corresponding to each of the image frames of the video, and wherein the method may further comprise generating the confirmation model input data by synthesizing the plurality of detection model output data.

The confirmation model input data may be generated by arranging at least some of the detection model output data in time series.

The detection model may include an object detection model and a posture detection model, and wherein the detecting may comprise: detecting the object by inputting the image frames of the video to the object detection model, and detecting the posture by inputting the image frames of the video to the posture detection model.

The detection model may include a first detection model for detecting one or more preset targets of a first type and a second detection model for detecting one or more preset targets of a second type, wherein the method may further comprise defining a category of the video using the video and a classification model, and wherein the detecting may comprises: when the category of the video is defined to a first category corresponding to the first type, detect the preset targets by inputting the image frames of the video to the first detection model, and when the category of the video is defined to a second category corresponding to the second type, detect the preset targets by inputting the image frames of the video to the second detection model.

The confirmation model may include a first confirmation model corresponding to the first detection model and a second confirmation model corresponding to the second detection model, and wherein the determining may comprise: when the category of the video is defined to the first category, determine whether medication has been administered by inputting the confirmation model input data to the first confirmation model, and when the category of the video is defined to the second category, determine whether medication has been administered by inputting the confirmation model input data to the second confirmation model.

The detecting may comprise estimating a location of the preset targets in the image frames of the video so that the detection result and the confirmation model input data reflect the location of the preset targets, and wherein the determining may comprise determining whether medication has been administered considering the location of the preset targets.

According to an embodiment, a method, performed by one or more processors, for training a detection model and a confirmation model to determine whether medication has been administered, the method may comprising: obtaining detection model training data including training images and detection model labels corresponding to the training images, wherein each of the detection model labels may have a class for a medicine or a medicine container and a class for a posture related to medication administration, and wherein the detection model labels may include a first detection model label corresponding to a first image of the training images, and a second detection model label corresponding to a second image of the training images; obtaining output data by inputting the training images to the detection model; updating the detection model by comparing the detection model labels and the output data of the detection model; obtaining confirmation model training data including confirmation model input data and a confirmation model label corresponding to the confirmation model input data, wherein the confirmation model label may include a label for determining whether medication has been administered, and wherein the confirmation model input data may be generated based on the output data of the detection model; obtaining output data by inputting the confirmation model input data to the confirmation model; and updating the confirmation model by comparing the confirmation model label and the output data of the confirmation model, wherein the posture may include at least one of a posture of holding a medicine container or a posture of taking a medicine.

According to an embodiment, a method, performed by one or more processors, for training a monitoring model determining whether a user has administered medication using a video recorded by a wearable device worn on the user's wrist, the method may comprising: obtaining main-hand training data including a main-hand training video and a first label corresponding to the main-hand training video, wherein the main-hand training video was recorded by a first wearable device when a first person administered medication mainly by a main hand that the first person worn the first wearable device on the main hand, and wherein the first label indicates medication administration; obtaining sub-hand training data including a sub-hand training video and a second label corresponding to the sub-hand training video, wherein the sub-hand training video was recorded by a second wearable device when a second person administered medication mainly by a sub hand that the second person worn the second wearable device on the opposite hand of the sub hand, and wherein the second label indicates medication administration; updating the monitoring model using one of the main-hand training data and the sub-hand training data; and updating the updated monitoring model again using the other of the main-hand training data and the sub-hand training data.

The first label may include a main-hand label indicating medication administration mainly performed by the main hand, wherein the second label may include a sub-hand label indicating medication administration mainly performed by the sub hand, and wherein the monitoring model may determine whether the user has administered medication distinguishing medication administration mainly performed by the main hand and medication administration mainly performed by the sub hand.

The method may further comprise: obtaining medication non-administration training data including a medication non-administration training video and a medication non-administration label corresponding to the medication non-administration training video, wherein the medication non-administration training video represents medication non-administration and the medication non-administration label indicates medication non-administration; and updating the updated monitoring model again using the medication non-administration training data.

According to an embodiment, a method, performed by one or more processors, for training a detection model and a confirmation model to determine whether a user has administered medication using a video recorded by a wearable device worn on the user's wrist, the method may comprising: obtaining main-hand training data including a main-hand training video, first detection model labels and a first confirmation model label, wherein the main-hand training video might be recorded by a first wearable device when a first person administered medication mainly by a main hand that the first person worn the first wearable device on the main hand, wherein each of the first detection model labels may include a class for detecting an appearance of a medicine or a medicine container and a class for detecting a posture related to medication administration, and wherein the first confirmation model label may indicate medication administration; obtaining sub-hand training data including a sub-hand training video, second detection model labels and a second confirmation model label, wherein the sub-hand training video might be recorded by a second wearable device when a second person administered medication mainly by a sub hand that the second person worn the second wearable device on the opposite hand of the sub hand, wherein each of the second detection model labels may include a class for detecting an appearance of a medicine or a medicine container and a class for detecting a posture related to the medication administration, and wherein the second confirmation model label may indicate medication administration; updating the determination model using at least a portion of the main-hand training data and at least a portion of the sub-hand training data; and updating the confirmation model using at least a portion of the main-hand training data and at least a portion of the sub-hand training data.

The confirmation model may be updated, further using output data of the updated determination model.

The determination model may be updated using the main-hand training video, the first detection model labels, the sub-hand training video, and the second detection model labels, and wherein the confirmation model may be updated using the first detection model labels, the first confirmation model label, the second detection model labels, and the second confirmation model label.

The first confirmation model label may include a main-hand label indicating medication administration mainly performed by the main hand, wherein the second confirmation model label may include a sub-hand label indicating medication administration mainly performed by the sub hand, and wherein the confirmation model may determine whether the user has administered medication distinguishing medication administration mainly performed by the main hand and medication administration mainly performed by the sub hand.

According to an embodiment, a method, performed by one or more processors, for determining whether a user has administered medication using a video recorded by a wearable device worn on the user's wrist, the method may comprising: receiving the video recorded by the wearable device; and determining whether the user has administered medication by inputting the video to a monitoring model, wherein the monitoring model may be updated using one of main-hand training data and sub-hand training data, and then updated again using the other of the main-hand training data and the sub-hand training data, wherein the main-hand training data may include a main-hand training video and a first label corresponding to the main-hand training video, wherein the main-hand training video might be recorded by a first wearable device when a first person administered medication mainly by a main hand that the first person worn the first wearable device on the main hand, and wherein the first label may indicate medication administration, and wherein the sub-hand training data may include a sub-hand training video and a second label corresponding to the sub-hand training video, wherein the sub-hand training video might be recorded by a second wearable device when a second person administered medication mainly by a sub hand that the second person worn the second wearable device on the opposite hand of the sub hand, and wherein the second label may indicate medication administration.

The first label may include a main-hand label indicating medication administration mainly performed by the main hand, wherein the second label may include a sub-hand label indicating medication administration mainly performed by the sub hand, and wherein the monitoring model may determine whether the user has administered medication distinguishing medication administration mainly performed by the main hand and medication administration mainly performed by the sub hand.

According to an embodiment, a server for determining whether a user has administered medication using a video recorded by a wearable device worn on the user's wrist, the server may comprising: a transceiver receiving the video recorded by the wearable device; a memory storing a monitoring model for determining whether the user has administered medication; and one or more processors configured to determine whether the user has administered medication using the video received through the transceiver and the monitoring model, wherein the monitoring model may be trained using at least a main-hand training video being recorded by a first wearable device when a first person administered medication mainly by a main hand that the first person worn the first wearable device on the main hand, and wherein the one or more processors may be further configured to determine medication administration using the video and the monitoring model, wherein the video is recorded by the wearable device when the user administered medication mainly by a sub hand that the user worn the wearable device on the opposite hand of the sub hand.

The one or more processors may be further configured to determine whether the user has administered medication distinguishing medication administration mainly performed by the main hand and medication administration mainly performed by the sub hand.

According to an embodiment, a server for determining whether medication administration has been performed, the server may comprising: a transceiver receiving a video recorded by a wearable device; a memory storing a first model and a second model, wherein the first model may be trained to output whether medication administration related to a medical supply of a first category has been performed, and the second model may be trained to output whether medication administration related to a medical supply of a second category has been performed; and one or more processors configured to determine whether medication administration has been performed by inputting the video to the first model or the second model, wherein the one or more processors may be further configured to: define a category of the video based on image frames of the video; when the category of the video is defined to the first category, determine whether medication administration corresponding to the first category has been performed by inputting the video to the first model; and when the category of the video is defined to the second category, determine whether medication administration corresponding to the second category has been performed by inputting the video to the second model.

The memory may store a classification model for defining the category of the video, and wherein the one or more processors may be further configured to define the category of the video using the classification model and the video.

The classification model may define the category of the video considering both the medical supply of the first category and the medical supply of the second category, and wherein the one or more processors may be further configured to: when determining whether medication administration has been performed using the first model, determine whether medication administration has been performed considering the medical supply of the first category and a posture of the first category related to medication administration and not considering the medical supply of the second category, and when determining whether medication administration has been performed using the second model, determine whether medication administration has been performed considering the medical supply of the second category and a posture of the second category related to medication administration and not considering the medical supply of the first category.

The classification model may define the category of the video further considering the posture of the first category and the posture of the second category.

The video may include a plurality of image frames, and wherein the one or more processors may be further configured to: calculate a first value and a second value reflecting the number of image frames in which the medical supply of the first category and the second category, respectively, appears by inputting each of the plurality of image frames to the classification model, and define the category of the video using the first value and the second value.

The video may include a plurality of image frames, and wherein the one or more processors may be further configured to: calculate a first value and a second value reflecting the number of the medical supply of the first category and the second category, respectively, appeared in the plurality of image frames by inputting each of the plurality of image frames to the classification model, and define the category of the video using the first value and the second value.

The transceiver may receive data indicating the category of the video, and wherein the one or more processors may be further configured to define the category of the video according to the received data.

The one or more processors may be further configured to store information related to whether the user has administered medication determined by the model and information related to the category of the video to the memory.

According to an embodiment, a system for determining whether medication administration has been performed, the system may comprising: the server of the present disclosure; and a management server, wherein the management server may be configured to: receive the information related to whether the user has administered medication and the information related to the category of the video from the server, acquire a medication administration schedule of the user, and determine medication adherence of the user by comparing the information related to whether the user has administered medication and the information related to the category of the video to the medication administration schedule.

In the present disclosure, medication administration is meant to encompass various types of taking medications: a swallow of medicine (for example, pills, tablets, capsules, powders, and liquids) such as oral administration of medicine; inhalation of medicine using an inhaler, a turbuhaler, a nasal spray, or the like; administration of an eyedrop using an eye dropper; and injection of medicine using a syringe.

In the present disclosure, determination of whether medication has been administered is to determine, for example, whether medicine has been swallowed, whether medicine has been inhaled using an inhaler, a turbuhaler, a nasal spray, or the like, whether an eyedrop has been administered, and whether medicine has been injected using a syringe.

FIG. 1 is a diagram illustrating a medication administration process according to an embodiment, which shows the entire process in which a user administers medication. Referring to FIG. 1, the entire process of administering medication may include: a user approaches a medicine bottle storing pills therein (S10); the user pours pills out of the medicine bottle into the palm (S20); the user picks up the pills on the palm with the fingers (S30); and the user brings the pills to his/her mouth to swallow the pills (S40). However, patterns of performing a medication administration process (hereinafter, referred to as "medication administration patterns") may differ between users, and even for the same user, the medication administration patterns may vary from time to time. For example, in some cases, a user may bring a medicine bottle directly to his/her mouth and swallow the pills. In addition, FIG. 1 shows the case in which a user pours the pills out of the medicine bottle and swallows the pills, but the medication administration processes or the medication administration patterns may differ when different types of medication administration are performed. In some embodiments, the medication administration process may include: pressing a pill out of a blister pack and swallowing the pill; inhalation of medicine using an inhaler, a turbuhaler, a nasal spray, or the like; administration of an eyedrop using an eye dropper; and/or injection of medicine using a syringe. For example, in the case of inhalation of medicine using an inhaler, the entire process for administering medication may include: a user approaches an inhaler, opens a cap of the inhaler, brings the inhaler to his/her mouth, and/or inhales medicine. Accordingly, the medication administration patterns of a user may also vary.

In the present disclosure, the following will be described: a method for determining whether medication has been administered, on the basis of a video; a server using the method; and a system including the server. In particular, described are a method for determining whether medication has been administered, a server using the method, and a system including the server, wherein the method is applicable even to the cases in which the medication administration processes are performed according to the various medication administration patterns as described above.

1. System for Determining Whether Medication has been Administered

According to an embodiment of the present disclosure, disclosed is a system for determining whether medication has been administered.

The system for determining whether medication has been administered according to the embodiment is a system for determining whether a user has administered medication, in the case in which the user administers medication in order to diagnose, treat, or prevent diseases or disorders, or to promote health.

The system according to the embodiment may include multiple devices, and the multiple devices may determine whether medication has been administered, being in association with each other, for example, transmission and reception of data.

Figure 2:
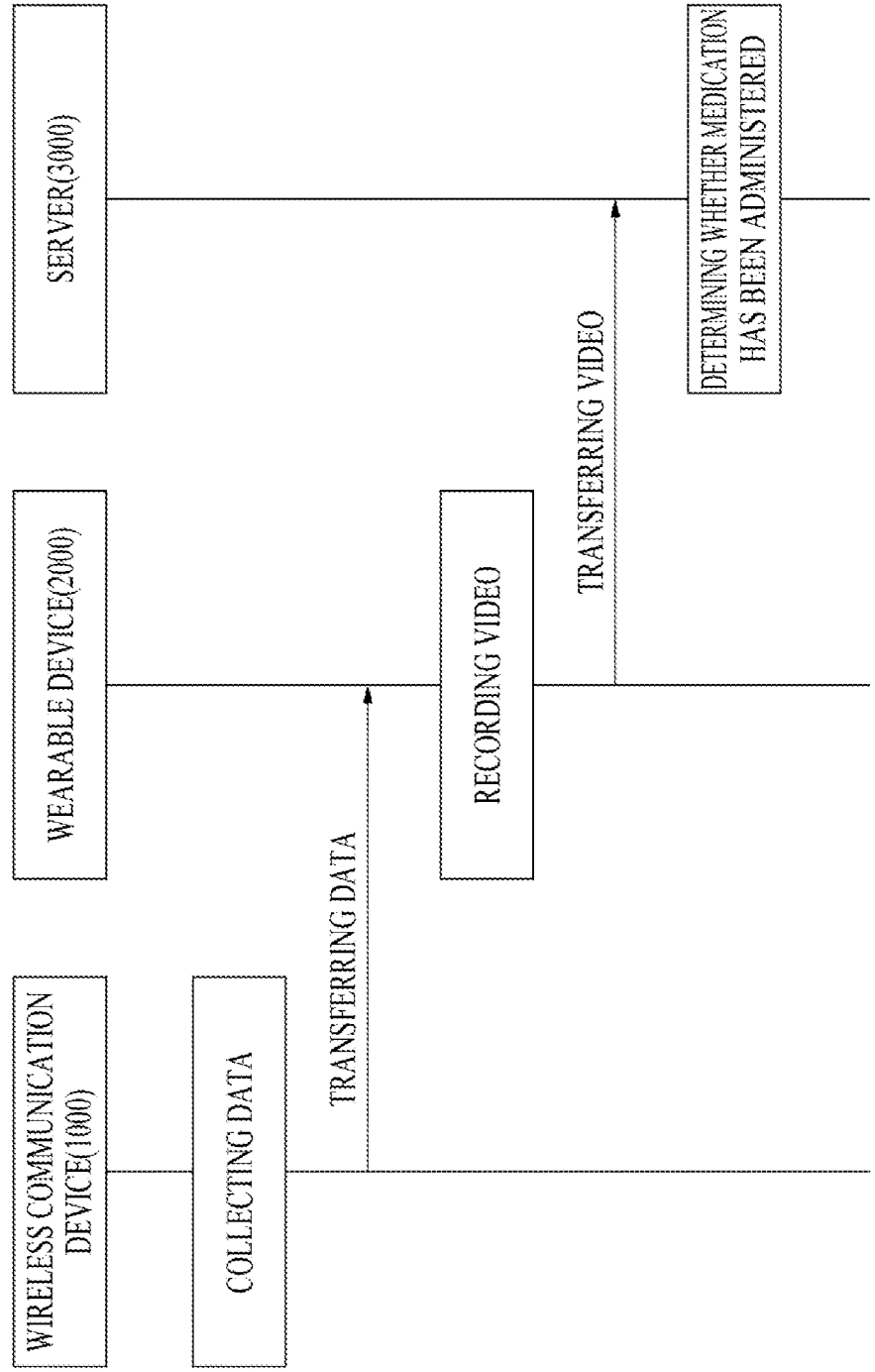
FIG. 2 is a diagram illustrating a system for determining whether medication has been administered, according to an embodiment.

FIG. 2 is a diagram illustrating a system for determining whether medication has been administered, according to an embodiment. Referring to FIG. 2, the system may include a wireless communication device 1000, a wearable device 2000, and a server 3000.

The wireless communication device 1000 may be attached to or located near medical supplies (for example, medicine containers such as a medicine bottle, an inhaler, a turbuhaler, a nasal spray, an eye dropper, and a syringe).

The wireless communication device 1000 may collect data. For example, the wireless communication device 1000 may collect data of a motion of a medical supply or ambient light or both.

The wireless communication device 1000 may transmit the collected data to the outside, such as the wearable device 2000 or the server 3000.

The wireless communication device 1000 may check whether the user has started a medication administration behavior using the collected data. For example, the wireless communication device 1000 may determine that the user has started the medication administration behavior when the motion of the medical supply is made to a predetermined degree or more. As another example, the wireless communication device 1000 may determine that the user has started the medication administration behavior when the ambient light is at a predetermine d illuminance or more. As still another example, the wireless communication device 1000 may determine that the user has started the medication administration behavior when the motion of the medical supply is made to a predetermined degree or more and the ambient light is at a predetermine d illuminance or more.

The wireless communication device 1000 may transfer a signal commanding activation of a camera unit (hereinafter, referred to as an "activation signal") to the outside, such as the wearable device 2000 or the server 3000. For example, when it is determined that the user has started the medication administration behavior, the wireless communication device 1000 may transmit the activation signal to the outside. The camera unit may be a camera unit of the wearable device 2000. Activating the camera unit may mean producing a video through photographing.

The wireless communication device 1000 may be a short-range wireless communication device, but is not limited thereto.

The wearable device 2000 may refer to a device that is provided in a form that the user is able to wear on the body. Examples of the wearable device 2000 include a smart watch, a smart band, a smart neckband, a smart ring, and a smart necklace, but are not limited thereto.

The wearable device 2000 may communicate with the wireless communication device 1000. For example, the wearable device 2000 may receive, from the wireless communication device 1000, the data of the motion of the medical supply or the ambient light or both. As another example, the wearable device 2000 may receive the activation signal for the camera unit from the wireless communication device 1000.

The wearable device 2000 may produce an image or video. For example, the wearable device 2000 may produce the image or video of medication administration.

The wearable device 2000 may produce the image or video on the basis of the data received from the wireless communication device 1000. For example, the wearable device 2000 may produce the image or video on the basis of the data of the motion of the medical supply or the ambient light or both, or on the basis of the activation signal. As a more specific example, the wearable device 2000 may produce the image or video when the motion of the medical supply is made to a predetermine d degree or more. As another more specific example, the wearable device 2000 may produce the image or video when the ambient light is at a predetermined illuminance or more. As still another more specific example, the wearable device 2000 may produce the image or video when the motion of the medical supply is made to a predetermine d degree or more and the ambient light is at a predetermined illuminance or more. As still another more specific example, the wearable device 2000 may produce the image or video when the activation signal is received.

The wearable device 2000 may produce the image or video on the basis of a signal strength of the data received from the wireless communication device 1000. For example, the wearable device 2000 may produce the image or video when the signal strength is in a predetermined range. The signal strength may be expressed as received signal strength indicator (RSSI), but is not limited thereto. When the signal strength is expressed as RSSI, examples of the predetermined range include a range equal to or greater than −90 dBm, a range equal to or greater than −70 dBm, and a range from −70 dBm to −50 dBm, but are not limited thereto.

The wearable device 2000 may produce the image or video, considering the signal strength of the data received from the wireless communication device 1000 and the content of the data, wherein the signal strength has priority over the content. For example, the wearable device 2000 does not produce the image or video when the signal strength is not in the predetermined range even though the motion of the medical product is made to a predetermine d degree or more. As another example, the wearable device 2000 does not produce the image or video when the signal strength is not in the predetermined range even though the ambient light is at a predetermined illuminance or more. As still another example, the wearable device 2000 does not produce the image or video when the signal strength is not in the predetermined range even though the motion of the medical product is made to a predetermine d degree or more and the ambient light is at a predetermined illuminance or more. As still another example, the wearable device 2000 does not produce the image or video when the signal strength is not in the predetermined range even though the activation signal is received. That is, the wearable device 2000 may produce the image or video, considering the signal strength of the data received from the wireless communication device 1000, prior to considering the content of the data.

The wearable device 2000 may produce the image or video by photographing the surroundings. In particular, in the case in which the wearable device 2000 is a smart watch or a smart band, the wearable device 2000 may photograph the surroundings of the user's hand to produce the image or video. In this case, the image or video may include at least a partial area of a palm of the user. That is, at least a portion of the image or at least a portion of at least one image frame of the video may include at least a partial area of a palm of the user.

The wearable device 2000 may measure information on the user wearing the wearable device 2000. For example, the wearable device 2000 may measure biometric information on the user wearing the wearable device 2000. Examples of the biometric information include information on movement, such as the number of steps, as well as a heart rate, blood oxygen saturation, and an electrocardiogram, but are not limited thereto. As another example, the wearable device 2000 may measure information on the surroundings of the user wearing the wearable device 2000. As a specific example, the wearable device 2000 may measure light around the user wearing the wearable device 2000.

The wearable device 2000 may communicate with the server 3000. For example, the wearable device 2000 may transmit the produced image or video to the server 3000. As another example, the wearable device 2000 may transmit the measured information on the user to the server 3000.

The server 3000 may communicate with the wireless communication device 1000 or the wearable device 2000 or both. The server 3000 may receive the image or video from the wearable device 2000. The server 3000 may receive the data of the motion of the medical supply or the ambient light or both from the wireless communication device 1000 or the wearable device 2000 or both.

The server 3000 may determine whether medication has been administered. For example, the server 3000 may determine whether medication has been administered, on the basis of information acquired from the wireless communication device 1000 or the wearable device 2000 or both. As a specific example, the server 3000 may determine whether medication has been administered, by analyzing the image or video received from the wearable device 2000.

1.1 Wireless Communication Device

Figure 3:
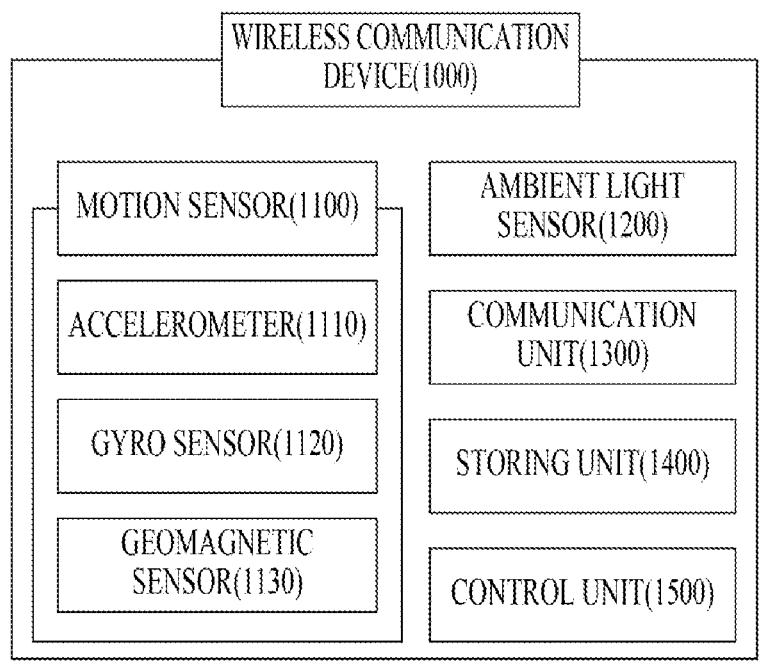
FIG. 3 is a block diagram illustrating a wireless communication device according to an embodiment.

FIG. 3 is a block diagram illustrating a wireless communication device according to an embodiment. Referring to FIG. 3, the wireless communication device 1000 may include a motion sensor 1100, an ambient light sensor 1200, a communication unit 1300, a storing unit 1400, and a control unit 1500.

The motion sensor 1100 may sense a motion of the wireless communication device 1000. In the case in which the wireless communication device 1000 is attached to the medical supply, the motion sensor 1100 may sense the motion of the medical supply by sensing the motion of the wireless communication device 1000. The motion sensor 1100 may include at least some among an accelerometer 1110, a gyro sensor 1120, and a geomagnetic sensor 1130. The motion sensor 1100 may be a six-axis sensor, a nine-axis sensor, or the like, but is not limited thereto.

The ambient light sensor 1200 may measure light around the wireless communication device 1000. In the case in which the wireless communication device 1000 is attached to or located near the medical supply, the ambient light sensor 1200 may measure light around the medical supply.

The communication unit 1300 may communicate with the outside, such as the wearable device 2000 or the server 3000. The communication unit 1300 may perform bi-directional or uni-directional communication. Examples of the communication unit 1300 include a transceiver, a beacon, a Bluetooth module, a WiFi module, a Zigbee module, an RF module, an NFC module, and combinations thereof, but are not limited thereto.

The communication unit 1300 may transmit data of a motion or light or both to the outside. For example, the communication unit 1300 may transmit data measured by the motion sensor 1100 or the ambient light sensor 1200 or both to the outside, such as the wearable device 2000 or the server 3000.

The communication unit 1300 may transmit the activation signal to the outside, such as the wearable device 2000 or the server 3000.

The storing unit 1400 may store various types of data and programs required for the wireless communication device 1000 to operate. The storing unit 1400 may store information that the wireless communication device 1000 acquires. For example, the storing unit 1400 may store data of a motion or light or both. As a specific example, the storing unit 1400 may store data measured by the motion sensor 1100 or the ambient light sensor 1200 or both. As another example, the storing unit 1400 may store the activation signal. Examples of the storing unit 1400 include anonvolatile semiconductor memory, a hard disk, flash memory, random-access memory (RAM), read-only memory (ROM), electrically erasable programmable read-only memory (EEPROM), other tangible non-volatile recording media, and combinations thereof, but are not limited thereto.

The control unit 1500 may perform processing and operation of various types of information within the wireless communication device 1000. The control unit 1500 may control the other elements constituting the wireless communication device 1000.

The control unit 1500 may be realized as a computer or a device similar thereto according to hardware, software, or a combination thereof. In hardware, the control unit 1500 may be one or multiple processors. Alternatively, the control unit 1500 may be provided as physically separate processors cooperating through communication. Examples of the control unit 1500 include a central processing unit (CPU), a graphics processing unit (GPU), a digital signal processor (DSP), a state machine, an application-specific integrated circuit (ASIC), a radio-frequency integrated circuit (RFIC), and combinations thereof, but are not limited thereto. In software, the control unit 1500 may be provided as a program for operating the hardware control unit 1500.

The control unit 1500 may perform control such that the motion sensor 1100 senses a motion, or such that the ambient light sensor 1200 measures light.

The control unit 1500 may perform control such that data of a motion or light or both is transmitted to the outside through the communication unit 1300. For example, the control unit 1500 may perform control such that data measured by the motion sensor 1100 or the ambient light sensor 1200 or both is transmitted through the communication unit 1300 to the outside, such as the wearable device 2000 or the server 3000.

The control unit 1500 may perform control such that data of a motion or light or both is stored in the storing unit 1400. For example, the control unit 1500 may perform control such that data measured by the motion sensor 1100 or the ambient light sensor 1200 or both is stored in the storing unit 1400.

The control unit 1500 may check whether the user has started a medication administration behavior using data of a motion or light or both. For example, the control unit 1500 may determine that the user has started the medication administration behavior when the motion is made to a predetermined degree or more. As another example, the control unit 1500 may determine that the user has started the medication administration behavior when the light is at a predetermined illuminance or more. As still another example, the control unit 1500 may determine that the user has started the medication administration behavior when the motion is made to a predetermined degree or more and the light is at a predetermined illuminance or more. The data of the motion may be data measured by the motion sensor 1100. The data of the light may be data measured by the ambient light sensor 1200.

The control unit 1500 may transmit the activation signal through the communication unit 1300 to the outside, such as the wearable device 2000 or the server 3000. For example, when it is determined that the user has started the medication administration behavior, the control unit 1500 may transmit the activation signal to the outside through the communication unit 1300.

Hereinafter, unless otherwise specially described, the operation of the wireless communication device 1000 may be interpreted as being performed under the control of the control unit 1500.

Not all the elements shown in FIG. 3 are essential elements of the wireless communication device 1000. The wireless communication device 1000 may further include an element not shown in FIG. 3. In addition, at least some of the elements of the wireless communication device 1000 shown in FIG. 3 may be omitted. For example, the wireless communication device 1000 may not include the motion sensor 1100 or the ambient light sensor 1200 or either.

1.2 Wearable Device

Figure 4:
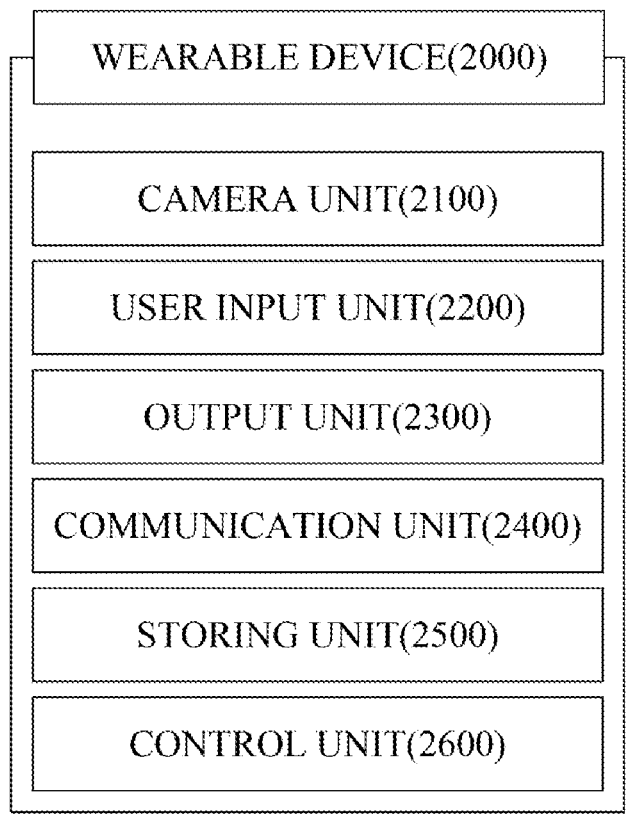
FIG. 4 is a block diagram illustrating a wearable device according to an embodiment.

FIG. 4 is a block diagram illustrating a wearable device according to an embodiment. Referring to FIG. 4, the wearable device 2000 may include a camera unit 2100, a user input unit 2200, an output unit 2300, a communication unit 2400, a storing unit 2500, and a control unit 2600.

The camera unit 2100 may produce an image or video. For example, the camera unit 2100 may photograph the surroundings of the wearable device 2000 to produce an image or video. The camera unit 2100 may include one or more camera modules. Examples of the camera module include an RGB camera, a thermal imaging camera, and a night vision device, but are not limited thereto.

The video that the camera unit 2100 produces may include multiple image frames. At least some of the multiple image frames may include at least a partial area of a palm of the user. The video may include a predetermined number of multiple image frames. The video may be a video acquired by photographing for a predetermined time.

The camera unit 2100 may be placed at a point in the wearable device 2000. For example, in the case in which the wearable device 2000 is a smart watch or a smart band, the camera unit 2100 may be placed at a strap part. Herein, the camera unit 2100 may be placed such that when the user wears the wearable device 2000 on the wrist, the camera unit 2100 is located on the inner side of the wrist. In addition, the camera unit 2100 may be placed such that when the user wears the wearable device 2000 on the wrist, the camera unit 2100 faces the direction of the user's hand so as to photograph the surroundings of the user's hand. The description of such location or direction in which the camera unit 2100 is placed is only an example and is not limited thereto.

The user input unit 2200 may perform a function of acquiring information from the user. The user input unit 2200 may receive user input from the user. Examples of the user input include key input, touch input, voice input, and combinations thereof, but are not limited thereto.

The user input unit 2200 may be realized as a user input device that is generally used. Examples of the user input device include a touch sensor sensing user touch, a microphone receiving audio signals, a gesture sensor recognizing user gestures, and combinations thereof, but are not limited thereto.

The output unit 2300 may perform a function of outputting information so that the user is able to check the information. The output unit 2300 may output information acquired from the user or information acquired from and/or processed by an external device. Output of information may be visual, auditory, and/or tactile output, or may be provided in various forms without being limited thereto.

The output unit 2300 may be realized as a display outputting images, a speaker outputting sound, a haptic device generating vibration, and/or other output means.

Alternatively, instead of a device itself outputting information to the outside, the output unit 2300 may be realized as an output interface (a USB port, the PS/2 port, or the like) that connects an external output device outputting information with the wearable device 2000.

The output unit 2300 may be integrated with the user input unit 2200. For example, in the case in which the output unit 2300 is a display, the output unit 2300 may be a touch display that is integrated with a touch sensor which is the user input unit 2200.

Like or similarly to the communication unit 1300 of the wireless communication device 1000 described above, the communication unit 2400 may perform a function of communicating with the outside, for example, transmitting or receiving data to or from the outside, or so on. For example, the communication unit 2400 may receive, from the wireless communication device 1000, the data of the motion or the light or both. As another example, the communication unit 2400 may receive the activation signal from the wireless communication device 1000. As still another example, the communication unit 2400 may transmit the image or video to the server 3000. As still another example, the communication unit 2400 may transmit the data of the motion or the light or both to the server 3000. A redundant description of a part the same as or similar to the communication unit 1300 of the wireless communication device 1000 will be omitted.

Like or similarly to the storing unit 1400 of the wireless communication device 1000 described above, the storing unit 2500 may store various types of data and programs required for the wearable device 2000 to operate. The storing unit 2500 may store information that the wearable device 2000 acquires. For example, the storing unit 2500 may store the image or video that the camera unit 2100 produces. As another example, the storing unit 2500 may store user input. As still another example, the storing unit 2500 may store information to be output so that the user is able to check the information. As still another example, the storing unit 2500 may store the data of the motion or the light or both received from the wireless communication device 1000. As still another example, the storing unit 2500 may store the activation signal. A redundant description of a part the same as or similar to the storing unit 1400 of the wireless communication device 1000 will be omitted.

Like or similarly to the control unit 1500 of the wireless communication device 1000 described above, the control unit 2600 may perform processing and operation of various types of information within the wearable device 2000. The control unit 2600 may control the other elements constituting the wearable device 2000. A redundant description of a part the same as or similar to the control unit 1500 of the wireless communication device 1000 will be omitted.

The control unit 2600 may activate the camera unit 2100. In this case, the control unit 2600 may perform control such that the camera unit 2100 produces an image or video. For example, the control unit 2600 may perform control such that the camera unit 2100 photographs the surroundings to produce an image or video. The image or video may be an image or video of medication administration.

The control unit 2600 may activate the camera unit 2100 on the basis of data received from the wireless communication device 1000. For example, the control unit 2600 may activate the camera unit 2100 on the basis of the data of the motion of the medical supply or the ambient light or both received from the wireless communication device 1000, or on the basis of the activation signal. As a more specific example, the control unit 2600 may activate the camera unit 2100 when the motion of the medical supply is made to a predetermined degree or more. As another more specific example, the control unit 2600 may activate the camera unit 2100 when the ambient light is at a predetermined illuminance or more. As still another more specific example, the control unit 2600 may activate the camera unit 2100 when the motion of the medical supply is made to a predetermined degree or more and the ambient light is at a predetermined illuminance or more. As still another more specific example, the control unit 2600 may activate the camera unit 2100 when the activation signal is received.

The control unit 2600 may activate the camera unit 2100 on the basis of the signal strength of data received from the wireless communication device 1000. For example, the control unit 2600 may activate the camera unit 2100 when the signal strength is in a predetermined range. The signal strength may be expressed as received signal strength indicator (RSSI), but is not limited thereto. When the signal strength is expressed as RSSI, examples of the predetermined range include a range equal to or greater than −90 dBm, a range equal to or greater than −70 dBm, and a range from −70 dBm to −50 dBm, but are not limited thereto.

The control unit 2600 may activate the camera unit 2100, considering the signal strength of the data received from the wireless communication device 1000 than the content of the data, wherein the signal strength has priority over the content. For example, the control unit 2600 does not activate the camera unit 2100 when the signal strength is not in the predetermined range even though the motion of the medical supply is made to a predetermine d degree or more. As another example, the control unit 2600 does not activate the camera unit 2100 when the signal strength is not in the predetermine d range even though the ambient light is at a predetermine d illuminance or more. As still another example, the control unit 2600 does not activate the camera unit 2100 when the signal strength is not in the predetermined range even though the motion of the medical supply is made to a predetermined degree or more and the ambient light is at a predetermined illuminance or more. As still another example, the control unit 2600 does not activate the camera unit 2100 when the signal strength is not in the predetermine d range even though the activation signal is received. That is, the control unit 2600 may activate the camera unit 2100, considering the signal strength of the data received from the wireless communication device 1000, prior considering the content of the data.

The control unit 2600 may perform control such that the user input unit 2200 acquires information from the user. The control unit 2600 may perform control such that the user input unit 2200 receives user input from the user.

The control unit 2600 may perform control such that the output unit 2300 performs a function of outputting information so that the user is able to check the information.

The control unit 2600 may perform control such that the communication unit 2400 performs a function of communicating with the outside, for example, transmitting or receiving data to or from the outside, or so on. The control unit 2600 may acquire information from the outside through the communication unit 2400.

The control unit 2600 may perform control such that the storing unit 2500 stores various types of data and programs required for the wearable device 2000 to operate. The control unit 2600 may perform control such that the storing unit 2500 stores information which the wearable device 2000 acquires.

Hereinafter, unless otherwise specially described, the operation of the wearable device 2000 may be interpreted as being performed under the control of the control unit 2600.

Not all the elements shown in FIG. 4 are essential elements of the wearable device 2000. The wearable device 2000 may further include an element not shown in FIG. 4. For example, the wearable device 2000 may further include at least one of the following: a motion sensor sensing movement of a user; an ambient light sensor measuring ambient light; a heart rate sensor measuring heart rate of a user; a blood oxygen saturation sensor measuring blood oxygen saturation of a user; and an electrocardiogram sensor measuring an electrocardiogram of a user. In addition, at least some of the elements of the wearable device 2000 shown in FIG. 4 may be omitted.

1.3 Server

Figure 5:
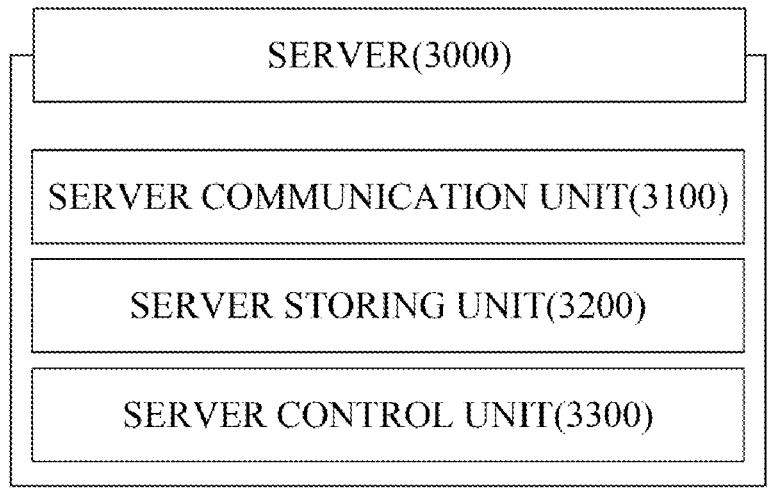
FIG. 5 is a block diagram illustrating a server according to an embodiment.

FIG. 5 is a block diagram illustrating a server according to an embodiment. Referring to FIG. 5, the server 3000 may include a server communication unit 3100, a server storing unit 3200, and a server control unit 3300.

Like or similarly to the communication unit 1300 of the wireless communication device 1000 described above, the server communication unit 3100 may perform a function of communicating with the outside, for example, transmitting or receiving data to or from the outside, or so on. For example, the server communication unit 3100 may receive the image or video from the wearable device 2000. As another example, the server communication unit 3100 may receive, from the wearable device 2000, data of the motion or the light or both. The data of the motion or the light or both may be data measured by the wearable device 2000. The data of the motion may incorporate the number of steps, postures, etc. of the user wearing the wearable device 2000. The data of the light may incorporate light around the wearable device 2000. As still another example, the server communication unit 3100 may receive, from the wearable device 2000, biometric information on the user wearing the wearable device 2000. A redundant description of a part the same as or similar to the communication unit 1300 of the wireless communication device 1000 will be omitted.

Like or similarly to the storing unit 1400 of the wireless communication device 1000 described above, the server storing unit 3200 may store various types of data and programs required for the server 3000 to operate. The server storing unit 3200 may store information that the server 3000 acquires. For example, the server storing unit 3200 may store the image or video received from the wearable device 2000. As another example, the server storing unit 3200 may store the data of the motion or the light or both received from the wearable device 2000. A redundant description of a part the same as or similar to the storing unit 1400 of the wireless communication device 1000 will be omitted.

Like or similarly to the control unit 1500 of the wireless communication device 1000 described above, the server control unit 3300 may perform processing and operation of various types of information within the server 3000. The server control unit 3300 may control the other elements constituting the server 3000. A redundant description of a part the same as or similar to the control unit 1500 of the wireless communication device 1000 will be omitted.

The server control unit 3300 may perform control such that the server communication unit 3100 performs a function of communication with the outside, for example, transmitting or receiving data to or from the outside, or so on. The server control unit 3300 may acquire information from the outside through the server communication unit 3100.

The server control unit 3300 may perform control such that the server storing unit 3200 stores various types of data and programs required for the server 3000 to operate. The server control unit 3300 may perform control such that the server storing unit 3200 stores information which the server 3000 acquires.

The server control unit 3300 may determine whether medication has been administered. For example, the server control unit 3300 may determine whether medication has been administered, on the basis of the image or video acquired from the wearable device 2000 through the server communication unit 3100.

Hereinafter, unless otherwise specially described, the operation of the server 3000 may be interpreted as being performed under the control of the server control unit 3300.

Not all the elements shown in FIG. 5 are essential elements of the server 3000. The server 3000 may further include an element not shown in FIG. 5. In addition, at least some of the elements of the server 3000 shown in FIG. 5 may be omitted.

The elements of the server 3000 may be physically included in one server, or may be distributed servers distributed for each function. For example, the server 3000 may include a first server performing a first function and a second server performing a second function. As a specific example, the server 3000 may include a first server determining whether medication has been administered, and a second server managing a result of determining whether medication has been administered. The first server and the second server may be physically separate particular servers. For example, the first server may be located in a first country, such as the Republic of Korea, and the second server may be located in a second country, such as the United States, Europe, Japan, and China.

1.4 Additional Elements

Referring back to FIG. 2, not all the elements shown in FIG. 2 are essential elements of the system. Some of the elements of the system shown in FIG. 2 may be omitted, or an element not shown in FIG. 2 may be further included.

For example, the system may further include a user terminal. Examples of the user terminal include a smartphone, a tablet PC, a laptop computer, and a desktop computer, but are not limited thereto. The user terminal may exchange data with at least some among the wireless communication device, the wearable device, and the server. The user terminal may provide the user, a guardian, or a healthcare worker with information on medication administration of the user or with an application for managing medication administration of the user. The user terminal may include an input unit, an output unit, a communication unit, a storing unit, a control unit, etc. The configuration or realization method of the elements of the user terminal is the same as that of the elements of the wireless communication device 1000 or the wearable device 2000, so a redundant part will be omitted.

An application running on the user terminal may provide a scheduling service, a notification service, or the like for inducing medication administration of the user. Herein, in running the application, the user terminal may apply data acquired from the wearable device 2000 or the server 3000.

2. Method for Determining Whether Medication Has Been Administered

2.1 Introduction

Hereinafter, a method for determining whether medication has been administered according to an embodiment will be described. For convenience of description, a description is made assuming that a method for determining whether medication has been administered is performed by the server, which is only one of various embodiments and does not mean that the method for determining whether medication has been administered is performed only by the server.

In other words, the method for determining whether medication has been administered according to an embodiment is not necessarily performed only by the server, but may be performed by a device other the server, such as the wireless communication device or the wearable device. In addition, a part of the method for determining whether medication has been administered may be performed by the server and the other part may be performed by a device other than the server, such as the wireless communication device or the wearable device.

In the following description of the method for determining whether medication has been administered according to an embodiment, unless otherwise mentioned, the operation that the server performs may be interpreted as being performed by the server control unit or by another element of the server controlled by the server control unit.

The server may determine whether medication has been administered using a model. Examples of the model include a deep learning model, such as an artificial neural network, a support vector machine, generalized linear models, decision trees, random forests, a gradient boosting machine, and combinations thereof, but are not limited thereto.

Hereinafter, some examples of the method for determining whether medication has been administered, on the basis of a video according to an embodiment will be described.

Figure 6:
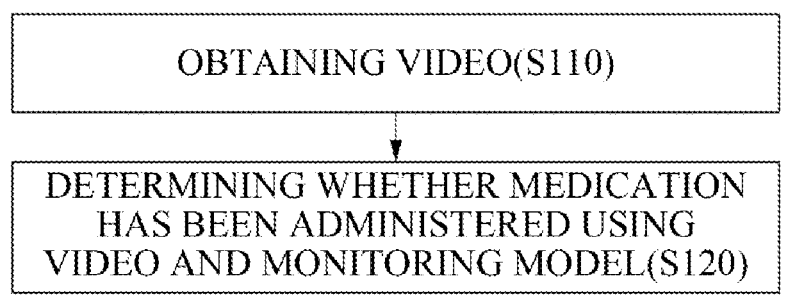
FIGS. 6 and 7 are diagrams illustrating a method for determining whether medication has been administered using a monitoring model according to an embodiment.
Figure 7:
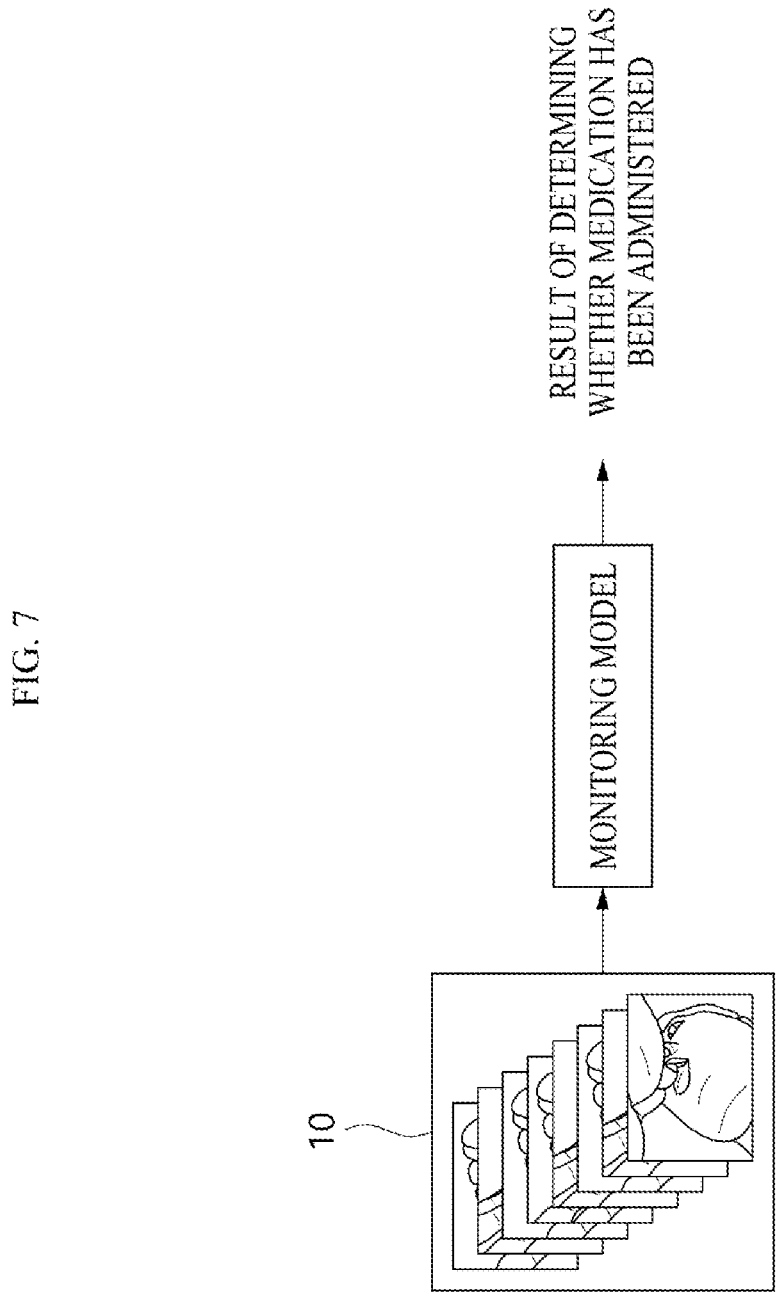

2.2 Method for Determining Whether Medication Has Been Administered Using Monitoring Model FIGS. 6 and 7 are diagrams illustrating a method for determining whether medication has been administered using a monitoring model according to an embodiment.

At step S110, the server may obtain a video. For example, the server may receive the video from the wearable device. Herein, the video may be acquired by the camera unit of the wearable device and transmitted through the communication unit of the wearable device. The video may include multiple image frames. The number of the multiple image frames may be 50 or more, 100 or more, 200 or more, 400 or more, 600 or more, 800 or more, or 1000 or more. The entire medication administration process may be captured in the video. Alternatively, most of the entire medication administration process may be captured in the video.

At step S120, the server may determine whether medication has been administered using the video and a monitoring model. The video may be obtained at step S110.

Referring to FIG. 7, the server may input the video 10 to the monitoring model and determine whether medication has been administered. For example, the server control unit may input the video 10 received through the server communication unit to the monitoring model and determine whether medication has been administered. As another example, the server control unit may store the video 10 received through the server communication unit, in the server storing unit, and input the video 10 stored in the server storing unit to the monitoring model, thereby determining whether medication has been administered. In this case, input data of the monitoring model may be the video 10 and output data may be a result of determining whether medication has been administered.

The video input to the monitoring model may have a specific format. For example, the video may include a predetermine d number of image frames. As another example, the video may have a predetermined resolution. As still another example, the video may have a predetermined ratio (a ratio between a width and a height).

The server may input the video to the monitoring model without performing preprocessing. For example, the server control unit may input the video received through the server communication unit to the monitoring model without performing preprocessing. That is, the video 10 input to the monitoring model may be the same as a video acquired by the camera unit. Alternatively, the server may perform preprocessing on the video and input the preprocessed video to the monitoring model. For example, the server control unit may perform preprocessing on the video received through the server communication unit and input the preprocessed video to the monitoring model. That is, the video 10 input to the monitoring model may be a result of performing preprocessing on a video acquired by the camera unit. Examples of the preprocessing include normalization, resizing, cropping, noise removal, and combinations thereof, but are not limited thereto.

The result of determining whether medication has been administered which is output from the monitoring model may be an index indicating whether medication has been administered. That is, output data of the monitoring model may be the index indicating whether medication has been administered. The server may acquire, using the monitoring model, the index indicating whether medication has been administered, for the video input to the monitoring model. As a non-limiting example, the index may be expressed as a numerical value.

The index, which is the output data of the monitoring model, indicating whether medication has been administered may have various formats.

For example, the index, which is the output data of the monitoring model, indicating whether medication has been administered may include an index indicating medication administration and an index indicating medication non-administration. Herein, the monitoring model may output either the index indicating medication administration or the index indicating medication non-administration. For example, the monitoring model outputs a value of 1 when medication administration is estimated, or outputs a value of 0 when medication non-administration is estimated.

As another example, the index, which is the output data of the monitoring model, indicating whether medication has been administered may include the following: an index indicating the probability that medication administration is estimated (hereinafter, referred to as a "medication administration probability index"); and an index indicating the probability that medication non-administration is estimated (hereinafter, referred to as a "medication non-administration probability index"). Herein, the monitoring model may output the medication administration probability index and the medication non-administration probability index together. The server may determine whether medication has been administered using the medication administration probability index and the medication non-administration probability index. For example, when the medication administration probability index is greater than the medication non-administration probability index, the server may determine that medication has been administered. When the medication non-administration probability index is greater than the medication administration probability index, the server determines that medication has not been administered. As another example, the server may determine that medication has been administered when the medication administration probability index satisfies a predetermined condition. As an example of satisfying the predetermined condition, the medication administration probability index is equal to or greater than a predetermined value, but no limitation thereto is imposed.

Examples of the monitoring model include: a transformer model using an attention mechanism; a recurrent neural network (RNN) model such as long short-term memory (LSTM); a hybrid model such as 2D CNN-LSTM; and a deep learning model such as 3D ConvNet, Inflated 3D ConvNet (I3D), and SlowFast Network. However, the examples are not limited thereto.

Compared to the case in which the server determines whether medication has been administered, on the basis of a single image frame or several image frames, the case in which the server determines whether medication has been administered, on the basis of the video may have an improved accuracy of determining whether medication has been administered. For example, in the case in which whether medication has been administered is determine d using only a single image frame, it is determined that medication has been administered when medicine is detected in the image frame. As another example, in the case in which whether medication has been administered is determine d using only several image frames, it is determined that medication has been administered when medicine is detected in a predetermined number or more of image frames among the several image frames. However, even in those cases, the user may have not actually administered medication. Thus, it is difficult to accurately determine whether medication has been administered, using only a single image frame or several image frames. Conversely, as described above, in the case in which whether medication has been administered is determined on the basis of the video, it is not determined that medication has been administered just because medicine is detected in a specific image frame, but whether medication has been administered is determined considering a medication administration process captured in the video overall. Therefore, compared to the case in which whether medication has been administered is determined on the basis of a single image frame or several image frames, whether medication has been administered is accurately determined.

Figure 8:
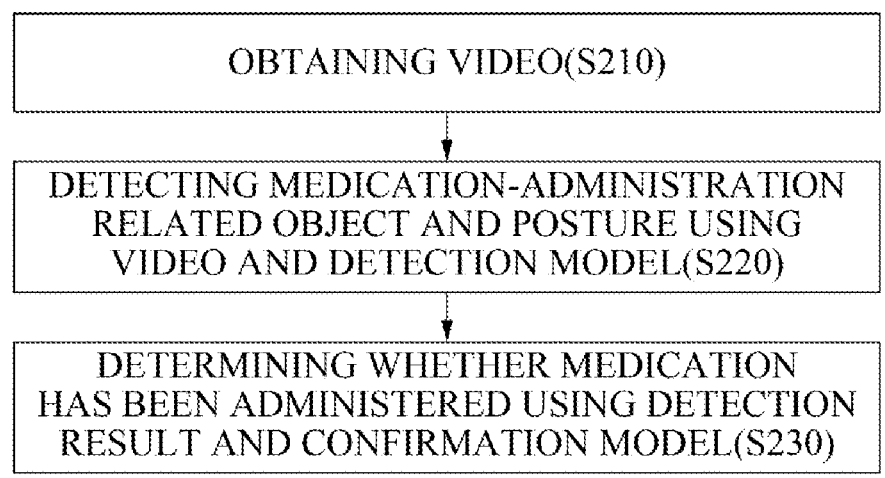
FIGS. 8 and 9 are diagrams illustrating a method for determining whether medication has been administered using a detection model and a confirmation model according to an embodiment.
Figure 9:
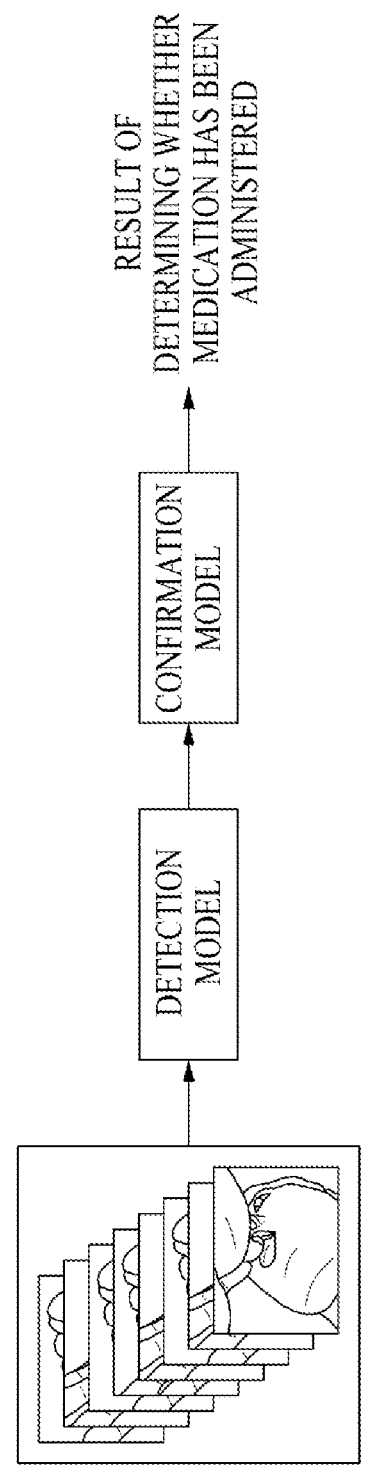

2.3 Method for Determining Whether Medication Has Been Administered Using Detection Model and Confirmation Model FIGS. 8 and 9 are diagrams illustrating a method for determining whether medication has been administered using a detection model and a confirmation model according to an embodiment. The server may determine whether medication has been administered using a video, a detection model, and a confirmation model. The server may obtain a video (S210), may detect objects and postures related to medication administration (hereinafter, referred to as medication-administration related objects and medication-administration related postures) using the video and a detection model (S220), and may determine whether medication has been administered using a result of detecting the medication-administration related objects and postures (hereinafter, referred to as a "detection result") and a confirmation model (S230).

At step S210, the server may obtain a video. For example, the server may receive the video from the wearable device. Herein, the video may be acquired by the camera unit of the wearable device and transmitted through the communication unit of the wearable device. The video may include multiple image frames. The number of the multiple image frames may be 50 or more, 100 or more, 200 or more, 400 or more, 600 or more, 800 or more, or 1000 or more. The entire medication administration process may be captured in the video. Alternatively, most of the entire medication administration process may be captured in the video.

At step S220, the server may detect the medication-administration related objects and postures using the video and the detection model. For example, the server control unit may detect the medication-administration related objects and postures using the video received through the server communication unit and the detection model. As another example, the server control unit may store the video received through the server communication unit in the server storing unit, and may detect the medication-administration related objects and postures using the video stored in the server storing unit and the detection model. The video may be acquired at step S210.

Figure 10:
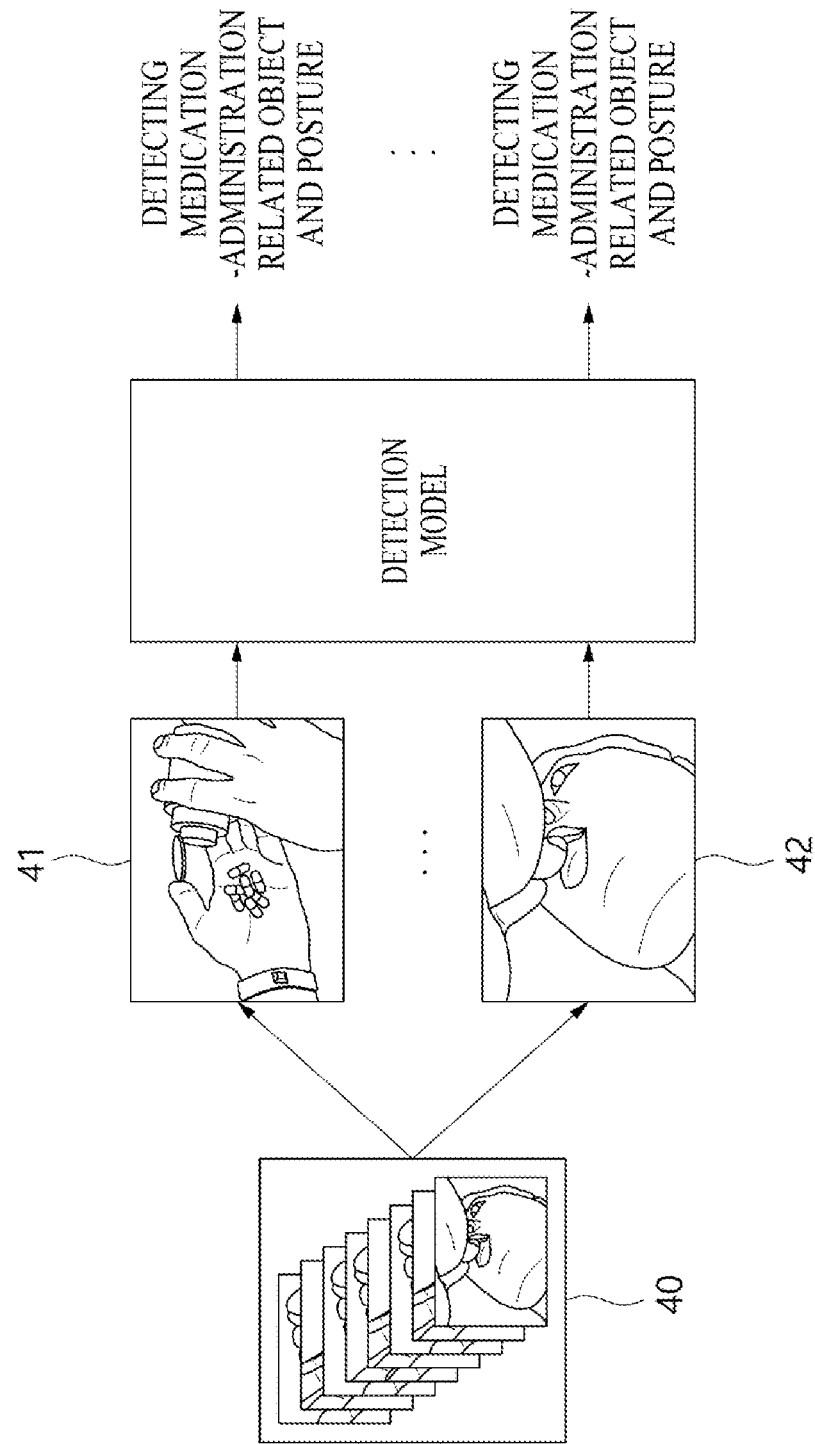
FIG. 10 is a diagram illustrating detection of medication-administration related objects and postures using a detection model according to an embodiment.

FIG. 10 is a diagram illustrating detection of medication-administration related objects and postures using a detection model according to an embodiment.

Referring to FIG. 10, the server may input image frames 41 and 42 of a video 40 to the detection model and detect the medication-administration related objects and postures included in the image frames 41 and 42. In this case, input data of the detection model may be the image frames 41 and 42. The server may input the video to the detection model image frame by image frame and detect medication-administration related objects and postures in the image frames. In this case, the server detects medication-administration related objects and postures with respect to all image frames of the video, so that the medication-administration related objects and postures included in the video are detected. The server may detect medication-administration related objects and postures with respect to only some of all image frames of the video.

The fact that the server inputs an image frame to the detection model and detects a medication-administration related object may mean that the server inputs an image frame to the detection model and determines whether a medication-administration related object is present in the image frame. The fact that the server inputs an image frame to the detection model and detects a medication-administration related posture may mean that the server inputs an image frame to the detection model and determines whether a medication-administration related posture is present in the image frame. Herein, determining whether a medication-administration related posture is present may mean determining whether a specific scene corresponding to a medication-administration related posture is present. In this case, the fact that the server inputs an image frame to the detection model and detects a medication-administration related posture may mean that the server inputs an image frame to the detection model and determines whether a specific scene corresponding to a medication-administration related posture is present in the image frame. The medication-administration related objects and the medication-administration related postures will be described in detail later.

The image frame input to the detection model may have a specific format. For example, the image frame may have a predetermined resolution. As another example, the image frame may have a predetermined ratio (a ratio between a width and a height).

The server may input the image frame to the detection model without performing preprocessing. For example, the server control unit may input the image frame received through the server communication unit to the detection model without performing preprocessing. That is, the image frames 41 and 42 input to the detection model may be the same as image frames acquired by the camera unit. Alternatively, the server may perform preprocessing on an image frame and input the preprocessed image frame to the detection model. For example, the server control unit may perform preprocessing on the image frame received through the server communication unit and input the preprocessed image frame to the detection model. That is, the image frames 41 and 42 input to the detection model may be results of preprocessing on image frames acquired by the camera unit. Examples of the preprocessing include normalization, resizing, cropping, noise removal, and combinations thereof, but are not limited thereto.

The detection model may output data related to medication-administration related objects and postures (hereinafter, referred to as "detection model output data"). In this case, output data of the detection model may be referred to as detection model output data. The server may acquire the detection model output data using the detection model. When the video includes N image frames, the server inputs the N image frames to the detection model and acquires N pieces of detection model output data corresponding to the N image frames. That is, the server may input the video to the detection model image frame by image frame and may acquire a detection result that includes the detection model output data corresponding to each image frame and corresponds to the video. As a non-limiting example, the detection model output data may be expressed as a numerical value. The detection model output data will be described in more detail later.

Hereinafter, the medication-administration related objects and the medication-administration related postures will be described in more detail.

Figure 11:
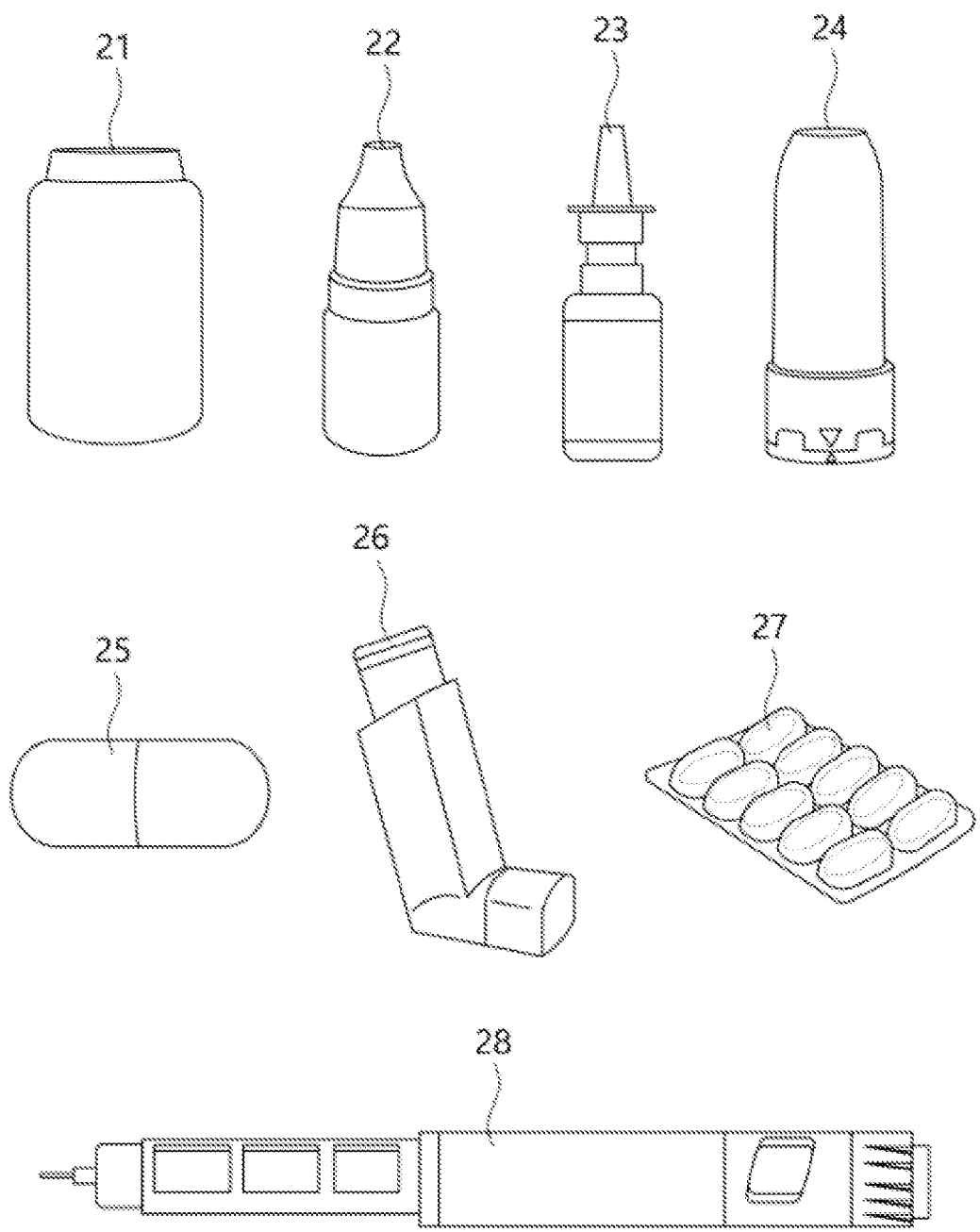
FIG. 11 is a diagram illustrating several types of medication-administration related objects.

FIG. 11 is a diagram illustrating several types of medication-administration related objects. The medication-administration related objects may include various types of objects related to medication administration, such as objects which are used by the user for medication administration. As a non-limiting example, referring to FIG. 11, medication-administration related objects may include a medicine bottle 21, an eye dropper 22, a nasal spray 23, a turbuhaler 24, a pill 25, an inhaler 26, a blister pack 27, a syringe 28, etc. Although not shown, the medication-administration related objects may include a user's body parts, such as the arms, hands, wrists, palms, outer parts of the palms, face, mouth, and nose.

Figure 12:
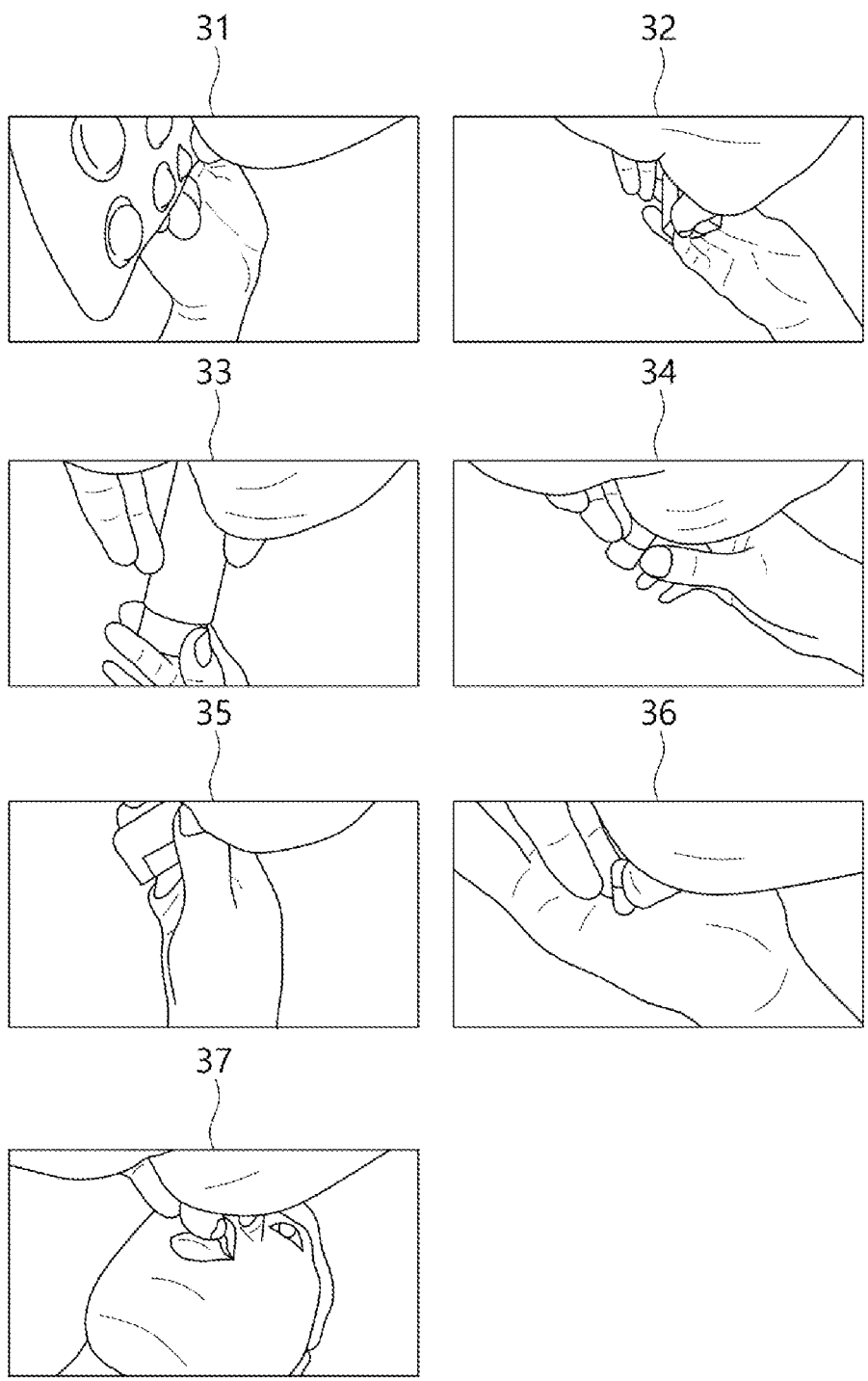
FIG. 12 is a diagram illustrating several types of medication-administration related postures.

FIG. 12 is a diagram illustrating several types of medication-administration related postures. The medication-administration related postures may include various types of postures related to medication administration, such as positioning of the user for medication administration. As anon-limiting example, referring to FIG. 12, the medication-administration related postures may include the following: postures for holding medication-administration related objects, such as a posture 31 for holding a blister pack, a posture 32 for holding an inhaler, a posture 33 for holding a turbuhaler, a posture 34 for holding an eye dropper, a posture 35 for holding a nasal spray, and a posture 36 for holding a pill; a posture 37 for swallowing medicine such as a pill; postures for inhaling medicine using medication-administration related objects, such as an inhaler, a turbuhaler, and a nasal spray; a posture for administering an eyedrop using a medication-administration related object such as an eye dropper; a posture for injecting medicine using a medication-administration related object such as a syringe; and a posture for opening a medication-administration related object such as a medicine bottle.

Comparing a medication-administration related posture and a medication-administration related object, the medication-administration related posture may be regarded as a specific posture with one or more medication-administration related objects. For example, the posture 31 for holding a blister pack may be regarded as a posture with the blister pack and a hand. As another example, the posture 37 for swallowing medicine may be regarded as a posture with medicine and a face. That is, the medication-administration related posture may include at least a portion of a body and at least a portion of a medical supply. Accordingly, detecting a medication-administration related posture by the server may be not detecting one or more medication-administration related objects individually, but detecting a specific posture with the medication-administration related objects.

In some embodiments, the detection model may detect a medication-administration related object and posture that are related to medication administration of a specific type. For example, the detection model has trained to detect medication-administration related objects and postures associated with swallowing medicine, such as oral administration of a pill poured out of a medicine bottle, and is thus able to detect the medication-administration related objects and the medication-administration related postures associated with swallowing medicine from an image frame. As a more specific example, when an image frame is input, the detection model may detect a medicine bottle, a pill, a behavior of opening a medicine bottle, a behavior of holding a pill, and a behavior of swallowing a pill. In this case, the detection model may not be able to detect a medication-administration related object and a medication-administration related posture which are related to medication administration other than the specific type. For example, the detection model that has trained to detect a medication-administration related object and a medication-administration related posture which are associated with swallowing medicine, such as oral administration of a pill poured out of a medicine bottle, may not be able to detect a medication-administration related object and a medication-administration related posture which are associated with inhalation of medicine using an inhaler.

In some embodiments, the detection model may detect a medication-administration related object and posture that are related to multiple types of medication administration. For example, the detection model has trained to detect medication-administration related objects and postures which are related to at least two of medication administration among a swallow of medicine, use of an inhaler, use of a turbuhaler, use of a nasal spray, administration of an eyedrop, and injection of medicine, and is thus able to detect the medication-administration related objects and postures which are related to the at least two of medication administration, from an image frame.

Hereinafter, the detection model output data will be described in more detail.

As described above, the server may acquire the detection model output data using the detection model. The detection model output data may include multiple sub data Each piece of the multiple sub data may correspond to a specific area in an image frame. The specific area may be at least one of the following: an area corresponding to a medication-administration related object; an area corresponding to a medication-administration related posture; and an area unrelated to medication administration.

The detection model output data may include location information incorporating locations of a medication-administration related object and posture in an image frame. For example, the sub data of the detection model output data may include the location information. In this case, the location information may incorporate a location, in an image frame, of any one of a predetermined number of areas corresponding to the sub data. The location information may be expressed as a bounding box. Examples of expressions of the bounding box include Pascal VOC, and COCO, but are not limited thereto.

The detection model output data may include probability information on a medication-administration related object and posture. For example, the sub data of the detection model output data may include the probability information.

The probability information may include presence probability information or class probability information or both. The presence probability information may incorporate whether a medication-administration related object or a medication-administration related posture or both are present. The class probability information may incorporate the probability of a class of a medication-administration related object or a medication-administration related posture or both.

In some embodiments, classes of medication-administration related objects and medication-administration related postures may refer to types of medication-administration related objects and medication-administration related postures. For example, when a first medication-administration related object and posture and a second medication-administration related object and posture differ in type, the first medication-administration related object and posture and the second medication-administration related object and posture are different classes. As a more specific example, a medicine bottle and a pill may be different classes. As another more specific example, a medicine bottle and an inhaler may be different classes.

In some embodiments, a class of medication-administration related objects and postures may refer to a group of same or similar types of medication-administration related objects and postures. For example, when a first medication-administration related object and posture and a second medication-administration related object and posture are the same or similar in type, the first medication-administration related object and posture and the second medication-administration related object and posture are the same class. As a more specific example, a pill and a medicine bottle may be the same classes. However, even in this case, a medicine bottle and an inhaler may be different classes.

The class probability information may include object class probability information corresponding to a medication-administration related object or posture class probability information corresponding to a medication-administration related posture or both.

The probability information may include one or more probability values. The presence probability information may include one or more presence probability values. The class probability information may include one or more class probability values. The numbers of probability values included in the probability information may vary according to case.

The server may detect, on the basis of the detection model output data, a medication administration related object or a medication-administration related posture or both included in an image frame. The server may detect, on the basis of the sub data of the detection model output data, a medication-administration related object or a medication-administration related posture or both included in an image frame.

The server may detect, on the basis of the probability information of the sub data, a medication-administration related object or a medication-administration related posture or both included in an image frame. For example, the server may detect, on the basis of the presence probability information, a medication-administration related object or a medication-administration related posture or both by determining whether the medication-administration related object or the medication-administration related posture or both are present within an area corresponding to the presence probability information. As a more specific example, when the presence probability value is equal to or greater than a predetermined value, the server may determine that a medication-administration related object or a medication-administration related posture or both are present within an area corresponding to the presence probability value, and detects the medication-administration related object or the medication-administration related posture or both. As another example, the server may estimate, on the basis of the class probability information, a class of a medication-administration related object or a medication-administration related posture or both that are expected to be present within an area corresponding to the class probability information. As a more specific example, when the class probability value is equal to or greater than a predetermined value, the server may estimate that a class of a medication-administration related object or a medication-administration related posture or both that are expected to be present within an area corresponding to the class probability value is a class corresponding to the class probability value.

FIG. 13 is a diagram illustrating an example of detection model output data.

As an example of the detection model output data, FIG. 13 shows a case in which the server acquires data of three areas 51, 52, and 53 in an image frame 50. Specifically, the server may acquire data corresponding to each of the following: the area 51 corresponding to a medicine bottle, which is a medication-administration related object; the area 52 corresponding to a posture for holding a pill, which is a medication-administration related posture; and the area 53 unrelated to a medication-administration related object and posture. As shown in FIG. 13, a predetermined number of areas 51, 52, and 53 acquired by the server may include the areas 51 and 52 corresponding to a medication-administration related object or a medication-administration related posture or both as well as the area 53 unrelated thereto. However, compared to the areas 51 and 52 corresponding to a medication-administration related object or a medication-administration related posture or both, a probability value may be low for the unrelated area 53. Accordingly, as described above, the server may determine, on the basis of the probability value, the areas 51 and 52 corresponding to a medication-administration related object or a medication-administration related posture or both among the areas 51, 52, and 53, and may detect the medication-administration related object or the medication-administration related posture or both.

(b) of FIG. 13 shows a case in which detection model output data 61 include three pieces of sub data 62, 63, and 64 corresponding to the three areas 51, 52, and 53, respectively.

(b) of FIG. 13 shows, as an example of presence probability information, presence probability information 72 incorporating probability that a medication-administration related object or a medication-administration related posture or both are present within the bounding boxes 51, 52, and 53. In (b) of FIG. 13, the sub data 62, 63, and 64 each include one presence probability value, p1, p2, and p3 respectively, but no limitation thereto is imposed. In addition, (b) of FIG. 13 shows, as an example of class probability information, class probability information 73 incorporating the probability of a class of a medication-administration related object or a medication-administration related posture or both that are expected to be present within the bounding boxes 51, 52, and 53. The class probability information 73 includes object class probability information 74 and posture class probability information 75. In (b) of FIG. 13, each of the sub data 62, 63, and 64 includes "a" object class probability values as the object class probability information 74 and "b" posture class probability values as the posture class probability information 75, a total of "a+b" class probability values, but no limitation thereto is imposed.

The detection model output data may have a specific format. For example, referring to (b) of FIG. 13, the detection model output data 61 may have a 2D matrix format. Herein, rows of the detection model output data 61 each may correspond to one piece of sub data, 62, 63, and 64 respectively. In addition, columns of the detection model output data 61 each may correspond to a specific type of information, such as location information and probability information, included in the sub data 62, 63, and 64. However, the format of the detection model output data 61 shown in (b) of FIG. 13 is only an example, and is thus not limited thereto.

FIG. 13 shows the case in which the server acquires data of the three areas 51, 52, and 53 within the image frame 50 and the detection model output data 61 includes the three pieces of sub data 62, 63, and 64, but the numbers of areas acquired by the server may vary. For example, the server may acquire data of k areas. In this case, the detection model output data may include k pieces of sub data. According to the format shown in (b) of FIG. 13, the detection model output data may be expressed as a 2D matrix having k rows.

In addition, not all the elements shown in FIG. 13 are essential elements of the detection model output data. The detection model output data may further include an element not shown in FIG. 13. In addition, at least some of the elements of the detection model output data shown in FIG. 13 may be omitted. For example, the detection model output data may not include information on the bounding boxes. Alternatively, the detection model output data may not include the presence probability information. Alternatively, the detection model output data may not include the object class probability information or the posture class probability information or either.

Examples of the detection model include deep learning models, such as R-CNN, Fast R-CNN, Faster R-CNN, SPPNet, YOLO, and SSD, but are not limited thereto.

The detection model may include multiple sub detection models. The multiple sub detection models may detect a medication-administration related object or a medication-administration related posture or both of at least partially different classes for the models.

For example, the detection model may include: a first detection model detecting a medication-administration related object of a first type and a medication-administration related posture of the first type; and a second detection model detecting a medication-administration related object of a second type and a medication-administration related posture of the second type.

As another example, the detection model may include a detection model detecting a medication-administration related object (hereinafter, referred to as an "object detection model"), and a detection model detecting a medication-administration related posture (hereinafter, referred to as a "posture detection model").

Figure 14:
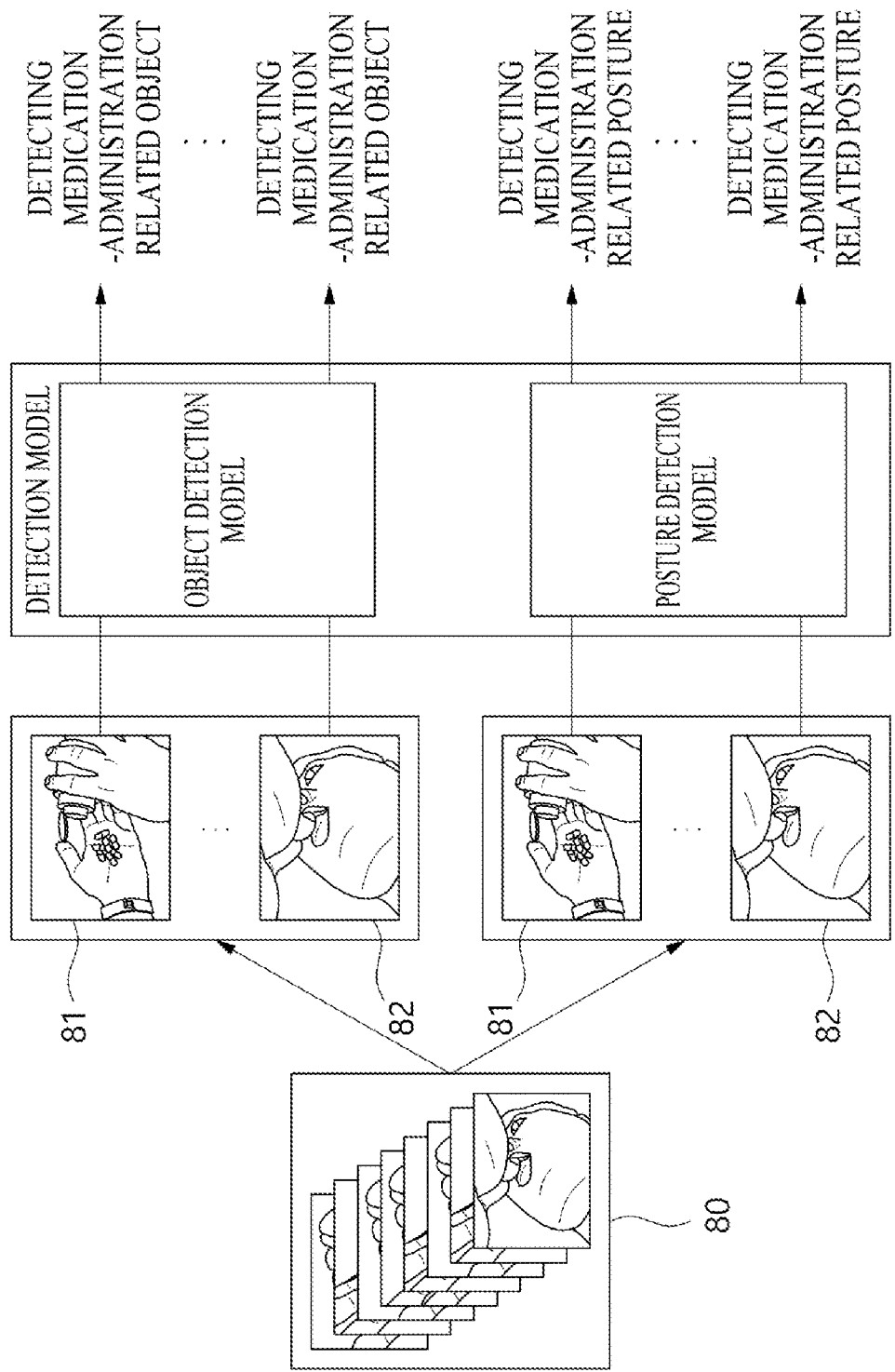
FIG. 14 is a diagram illustrating a detection model including an object detection model and a posture detection model according to an embodiment.

FIG. 14 is a diagram illustrating a detection model including an object detection model and a posture detection model according to an embodiment. Referring to FIG. 14, the server may input image frames 81 and 82 of a video 80 to the object detection model and detect medication-administration related objects included in the image frames 81 and 82. In addition, the server may input the image frames 81 and 82 of the video 80 to the posture detection model and detect medication-administration related postures included in the image frames 81 and 82. In this case, medication-administration related objects and postures in all image frames of the video 80 are detected using the object detection model and the posture detection model, so that the medication-administration related objects and postures included in the video 80 are detected. The image frames 81 and 82 shown in FIG. 14 may be input to the same object detection model. The image frames 81 and 82 shown in FIG. 14 may be input to the same posture detection model.

Examples of the sub detection models include deep learning models, such as R-CNN, Fast R-CNN, Faster R-CNN, SPPNet, YOLO, and SSD, but are not limited thereto.

Referring back to FIG. 8, at step S230, the server may determine whether medication has been administered using the detection result and the confirmation model. For example, the server control unit may determine whether medication has been administered using the detection result and the confirmation model. As another example, the server control unit may store the detection result in the server storing unit, and may determine whether medication has been administered using the detection result stored in the server storing unit and the confirmation model. The detection result may include the detection model output data. The detection result may be acquired at step S220.

The server may input the detection result as it is to the confirmation model. In this case, input data input to the confirmation model may be the same as the detection result of the detection model. Alternatively, the server may transform the detection result and input the resulting detection result to the confirmation model. In this case, input data input to the confirmation model may be generated on the basis of the detection result.

Figure 15:
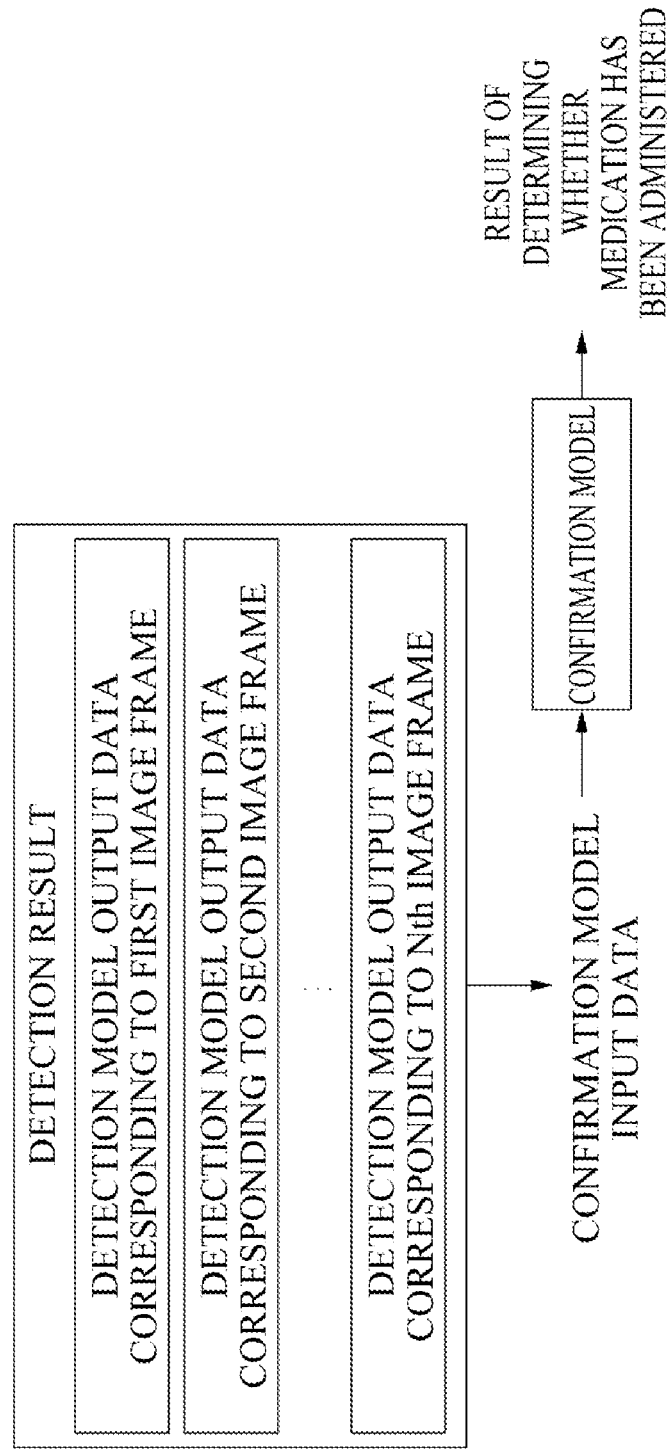
FIG. 15 is a diagram illustrating determination of whether medication has been administered using a confirmation model according to an embodiment.

FIG. 15 is a diagram illustrating determination of whether medication has been administered using a confirmation model according to an embodiment.

Referring to FIG. 15, the server may input confirmation model input data to the confirmation model and determine whether medication has been administered. In this case, input data of the confirmation model may be the confirmation model input data and output data may be a result of determining whether medication has been administered.

The server may generate the confirmation model input data on the basis of the detection result. Referring to FIG. 15, the detection result may include detection model output data corresponding to each image frame of the video. When a video includes N image frames, the detection result includes N pieces of detection model output data Herein, the server may generate the confirmation model input data by synthesizing the N pieces of the detection model output data.

The confirmation model input data may incorporate whether medication-administration related objects and postures of a specific class are present in the video. Alternatively, the confirmation model input data may incorporate movements of medication-administration related objects and postures of a specific class in the video over time.

Figure 16:
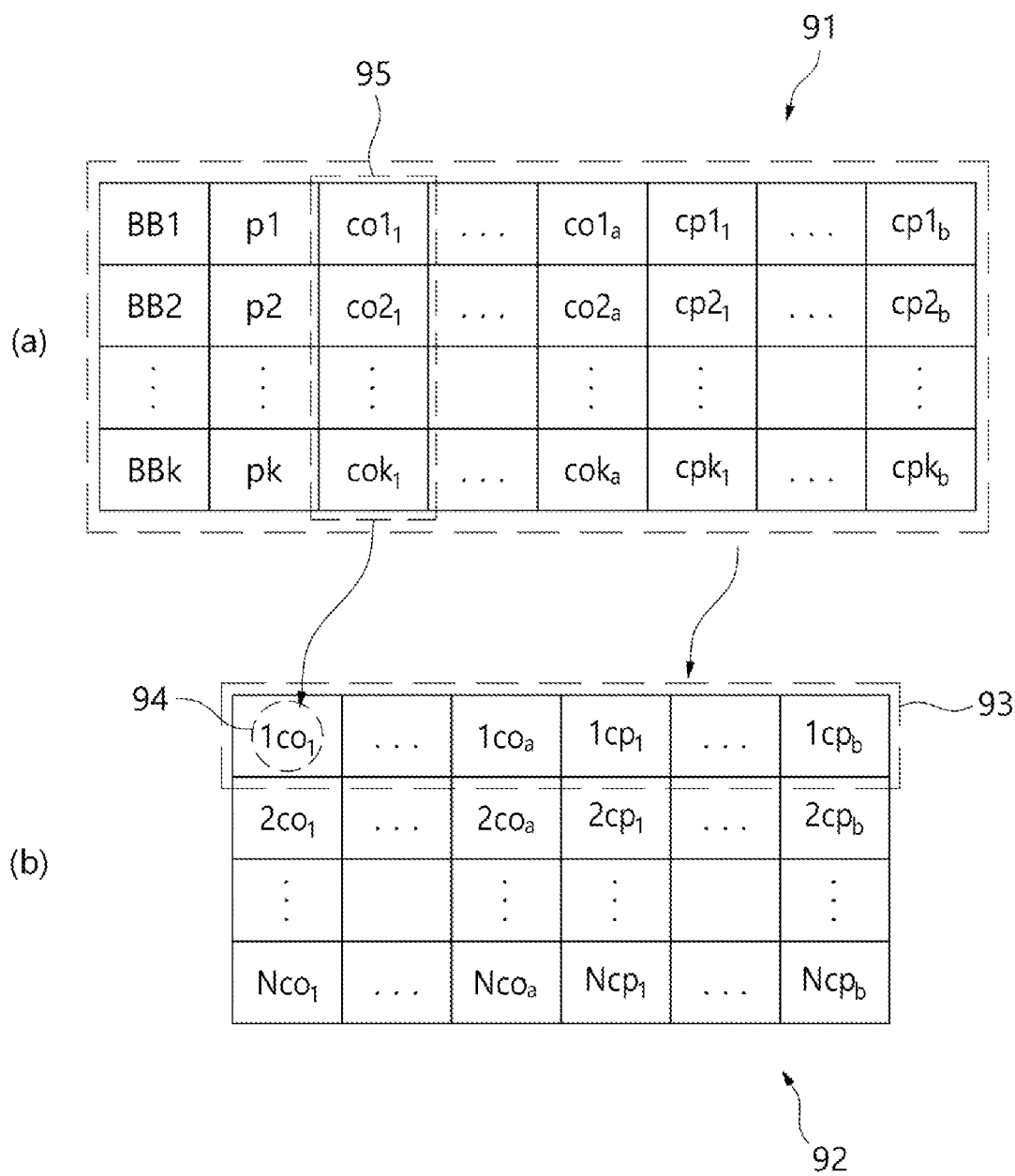
FIG. 16 is a diagram illustrating detection model output data and confirmation model input data according to an embodiment.

FIG. 16 is a diagram illustrating detection model output data and confirmation model input data according to an embodiment, assuming that the detection model outputs data of k areas and a video includes N image frames. (a) of FIG. 16 shows an example of detection model output data and (b) of FIG. 16 shows an example of confirmation model input data.

The confirmation model input data may include sub data corresponding to each image frame. For example, referring to (b) of FIG. 16, confirmation model input data 92 may include N pieces of sub data 93 corresponding to N image frames respectively. Comparing the detection model output data and the confirmation model input data, sub data of the detection model output data may correspond to a specific area in an image frame, and sub data of the confirmation model input data may correspond to a specific image frame.

The confirmation model input data may include sub data arranged in time series. For example, the confirmation model input data may include sub data arranged in ascending order in time series.

The sub data of the confirmation model input data may correspond to the detection model output data. For example, referring to FIG. 16, each piece of sub data 93 of the confirmation model input data may correspond to one piece of detection model output data 91. That is, the detection model output data 91 may include only information on one image frame, but the confirmation model input data 92 may include information on multiple image frames (for example, all image frames of the video). The sub data of the confirmation model input data may be generated using the detection model output data corresponding thereto.

The sub data of the confirmation model input data may incorporate whether a medication-administration related object or a medication-administration related posture or both are present in an image frame. For example, referring to FIG. 16, the sub data 93 of the confirmation model input data may include information 94 incorporating whether a medication-administration related object or a medication-administration related posture or both of a specific class are present in an image frame. The information 94 may be generated by synthesizing class probability information 95 of the detection model output data. Specifically, the information 94 corresponding to a specific class may be generated by synthesizing specific class probability information 95 of the detection model output data. Examples of generating the information 94 corresponding to a specific class by synthesizing the specific class probability information 95 include the following: adding probability values of the specific class probability information 95 and determining the sum as the information 94; determining a weighted average of the probability values as the information 94; and determining the maximum value among the probability values as the information 94. However, the examples are not limited thereto.

The confirmation model input data may have a specific format. For example, referring to (b) of FIG. 16, the confirmation model input data 92 may have a 2D matrix format. Herein, each row of the confirmation model input data 92 may correspond to one piece of the sub data 93. In addition, each column of the confirmation model input data 92 may correspond to a specific type of information such as probability information included in the sub data 93. However, the format of the confirmation model input data 92 shown in (b) of FIG. 16 is only an example, and is thus not limited thereto.

Referring back to FIG. 15, the result of determining whether medication has been administered which is output from the confirmation model may be an index indicating whether medication has been administered. That is, output data of the confirmation model may be the index indicating whether medication has been administered. The details of the index, which is the output data of the monitoring model, indicating whether medication has been administered may be applied to the index, which is the output data of the confirmation model, indicating whether medication has been administered, so a description thereof will be omitted.

Examples of the confirmation model include deep learning models, such as an RNN model, i.e., LSTM, and a hybrid model, i.e., 2D CNN-LSTM, but are not limited thereto.

Compared to the case in which whether medication has been administered is determine d using the confirmation model input data generated on the basis of a single image frame or several image frames, the case in which the server determines whether medication has been administered using the confirmation model input data generated on the basis of the video may have an improved accuracy. The reason is the same as or similar to the reason that the case in which the server determines whether medication has been administered, on the basis of the video has an improved accuracy, compared to the case in which the server determines whether medication has been administered, on the basis of a single image frame or several image frames, which is described in 2.2 Method for Determining Whether Medication Has Been Administered Using Monitoring Model. Therefore, a description of the reason will be omitted.

Although using a medication-administration related object and a medication-administration related posture in determining whether medication has been administered has been described, whether medication has been administered may be determine d using only either a medication-administration related object or a medication-administration related posture. However, using both a medication-administration related object and a medication-administration related posture has an improved accuracy of determining whether medication has been administered, compared to using only either a medication-administration related object or a medication-administration related posture. For example, the case in which the confirmation model input data includes information on both a medication-administration related object and a medication-administration related posture has an improved accuracy of determining whether medication has been administered using the confirmation model, compared to the case in which the confirmation model input data includes information on only either a medication-administration related object or a medication-administration related posture. To this end, it is more advantageous for the detection model to detect both a medication-administration related object and a medication-administration related posture than to detect only either a medication-administration related object or a medication-administration related posture.

2.4 Method for Determining Whether Medication Has Been Administered, Considering Category of Video The server may define a category of the video, and determine whether medication has been administered, considering the category. For example, the server may determine whether medication has been administered using a particular monitoring model according to the category of the video. As another example, the server may determine whether medication has been administered using a particular detection model according to the category of the video. As still another example, the server may determine whether medication has been administered using a particular confirmation model according to the category of the video.

Defining a category of the video may refer to determining a type of medication administration corresponding to the video. For example, the server may define a category of the video by determining which category the video corresponds to among two or more categories corresponding to different types of medication administration. In this case, examples of the categories include a medicine swallow category, an inhaler use category, a turbuhaler use category, a nasal spray use category, an eyedrop administration category, and a medicine injection category, but are not limited thereto.

The server may define a category of the video using a classification model. In this case, the server may determine whether medication has been administered, further using the classification model. For example, the server may determine whether medication has been administered using the classification model in addition to the monitoring model. As another example, the server may determine whether medication has been administered using the classification model in addition to the detection model and the confirmation model.

Figure 17:
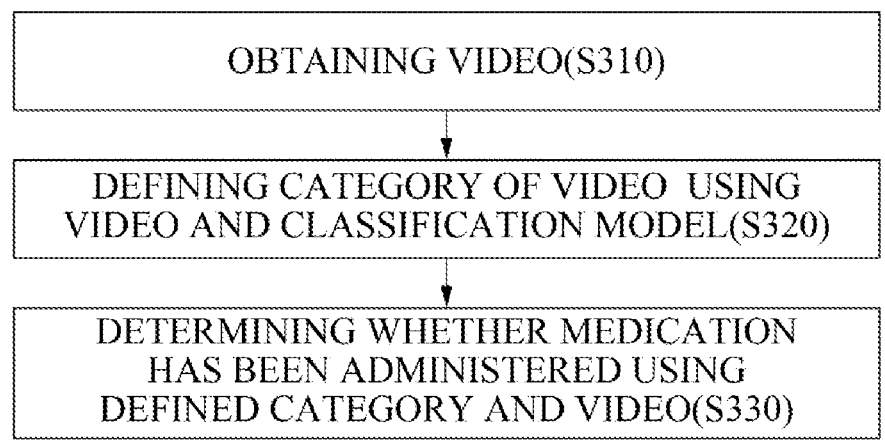
FIG. 17 is a diagram illustrating a method for determining whether medication has been administered using a classification model according to an embodiment.

FIG. 17 is a diagram illustrating a method for determining whether medication has been administered using a classification model according to an embodiment. The server may obtain a video (S310), may define a category of the video using the video and the classification model (S320), and may determine whether medication has been administered using the defined category and the video (S330).

At step S310, the server may obtain a video. For example, the server may receive the video from the wearable device. Herein, the video may be acquired by the camera unit of the wearable device and transmitted through the communication unit of the wearable device. The video may include multiple image frames. The number of the multiple image frames may be 50 or more, 100 or more, 200 or more, 400 or more, 600 or more, 800 or more, or 1000 or more. The entire medication administration process may be captured in the video. Alternatively, most of the entire medication administration process may be captured in the video.

At step S320, the server may define the category of the video using the video and the classification model. For example, the server control unit may define the category of the video using the video received through the server communication unit and the classification model. As another example, the server control unit may store the video received through the server communication unit in the server storing unit, and may define the category of the video using the video stored in the server storing unit and the classification model. The video may be obtained at step S310.

The fact that the server defines the category of the video using the classification model may mean that the server acquires an index indicating the category of the video (hereinafter, referred to as a "category index") using the classification model. As a non-limiting example, the category index may be expressed as a numerical value.

Figure 18:
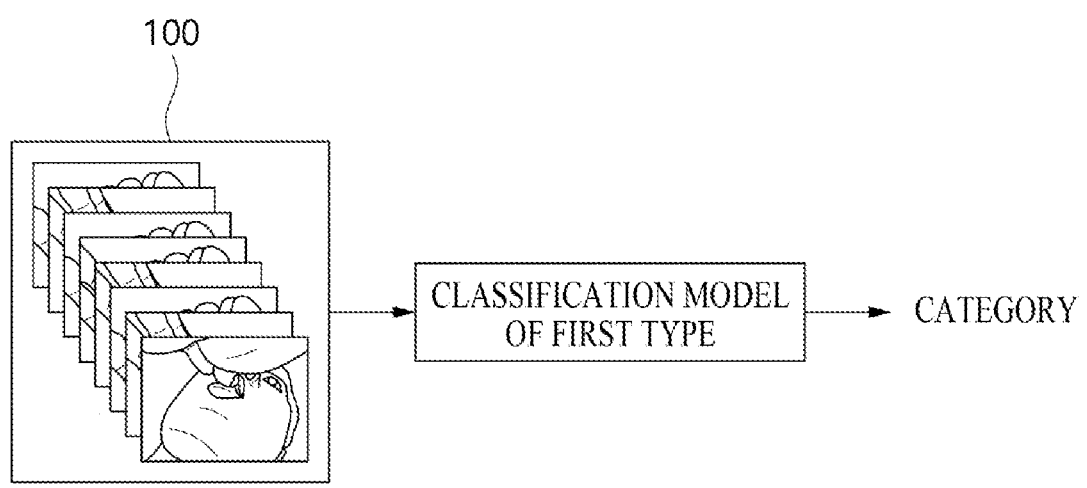
FIGS. 18 to 20 are diagrams illustrating a classification model according to an embodiment.
Figure 19:
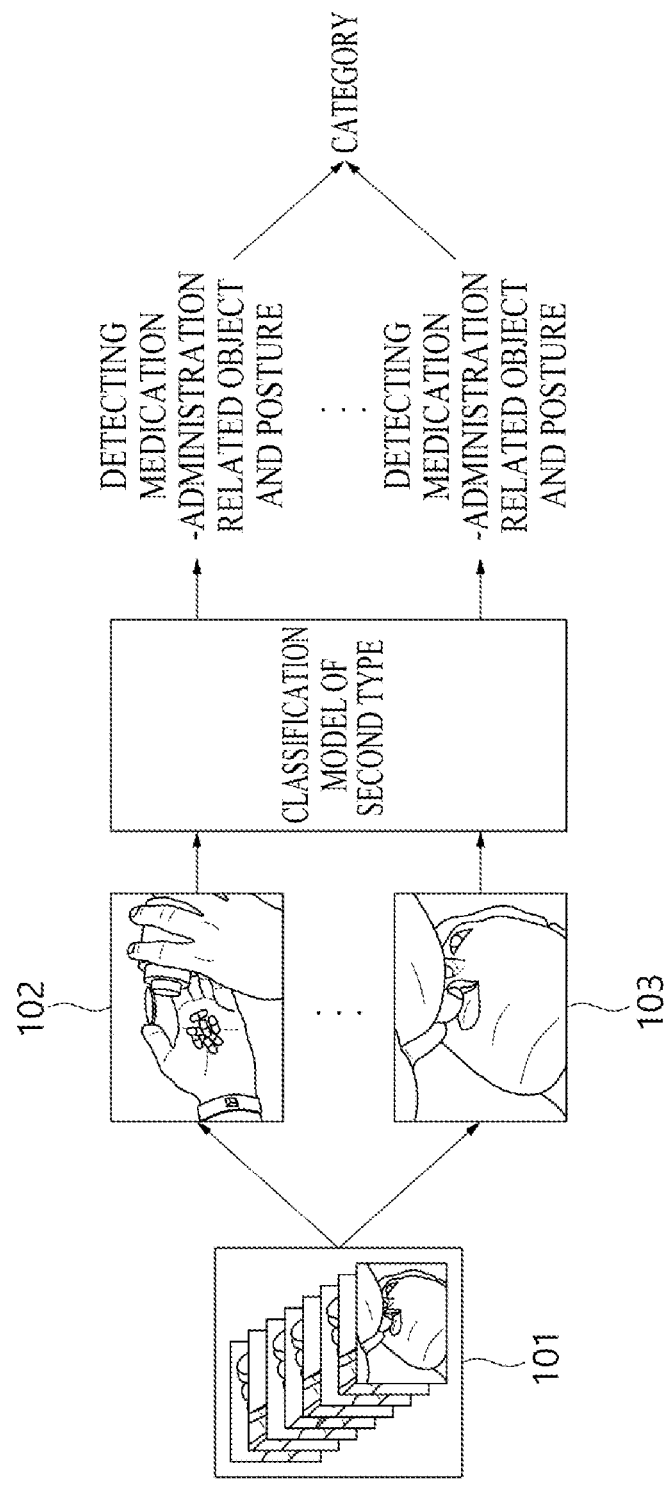
Figure 20:
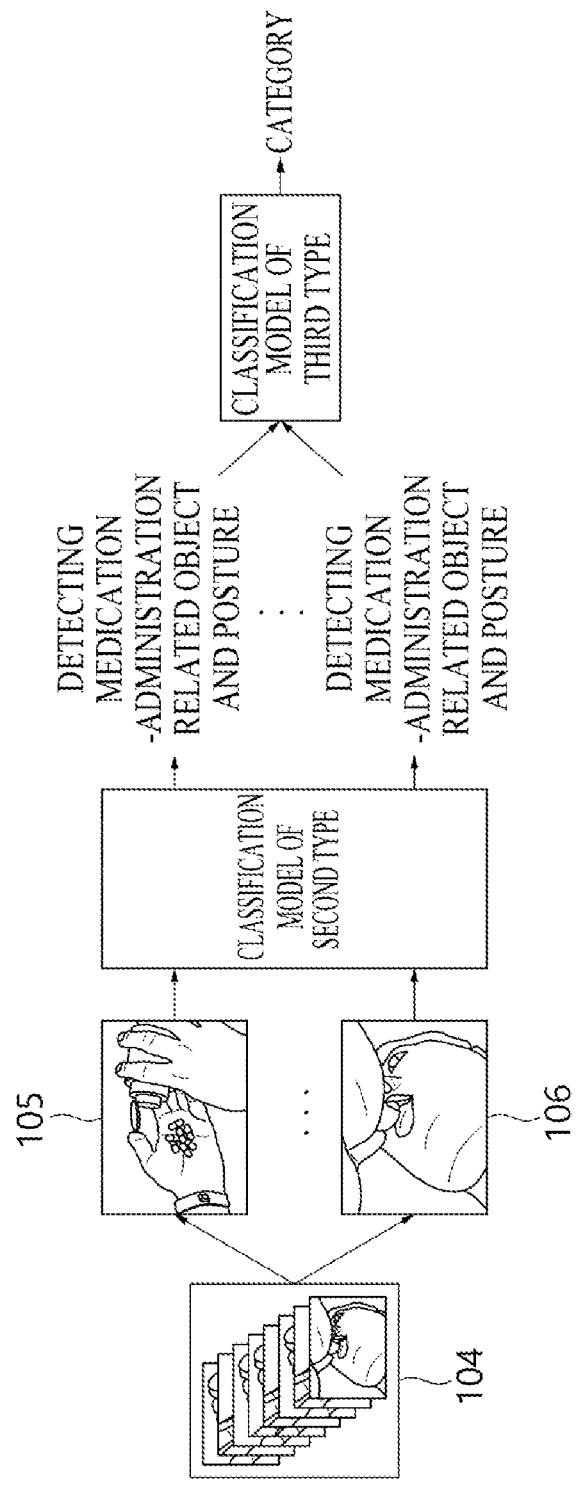

FIGS. 18 to 20 are diagrams illustrating a classification model according to an embodiment.

Referring to FIG. 18, the server may input a video 100 to the classification model and define the category of the video 100. For example, the server control unit may input the video 100 received through the server communication unit to the classification model and define the category of the video 100. As another example, the server control unit may store the video 100 received through the server communication unit in the server storing unit, may input the video 100 stored in the server storing unit to the classification model, and may define the category of the video 100. Hereinafter, the classification model that receives a video and defines the category of the video is referred to as a classification model of a first type. In this case, input data of the classification model of the first type may be the video.

The video input to the classification model of the first type may have a specific format. For example, the video may include a predetermine d number of image frames. As another example, the video may have a predetermined resolution. As still another example, the video may have a predetermine d ratio (a ratio between a width and a height).

The server may input the video to the classification model of the first type without performing preprocessing. For example, the server control unit may input the video received through the server communication unit to the classification model of the first type without performing preprocessing. That is, the video input to the classification model of the first type may be the same as a video acquired by the camera unit. Alternatively, the server may perform preprocessing on the video and input the preprocessed video to the classification model of the first type. For example, the server control unit may perform preprocessing on the video received through the server communication unit and input the preprocessed video to the classification model of the first type. That is, the video input to the classification model of the first type may be a result of performing preprocessing on a video acquired by the camera unit. Examples of the preprocessing include normalization, resizing, cropping, noise removal, and combinations thereof, but are not limited thereto.

Formats of output data of the classification model of the first type may be various.

For example, output data of the classification model of the first type may include multiple indexes indicating different categories. Herein, the classification model of the first type may output one of the multiple indexes. The server may determine the output index as the category index of the video.

As another example, output data of the classification model of the first type may include multiple indexes indicating probabilities that categories are estimated. Hereinafter, an index indicating the probability that the category is estimated is referred to as a category probability index. Multiple category probability indexes may correspond to different categories respectively. Herein, the classification model of the first type may output the multiple category probability indexes. In this case, the server may define the category of the video using the multiple category probability indexes. That is, the server may determine the category index of the video using the multiple category probability indexes. For example, the server may define the category of the video as the category corresponding to the maximum value among the multiple category probability indexes.

The classification model of the first type may be realized in a structure that is the same as or similar to that of the above-described monitoring model. However, even in this case, the classification model of the first type and the monitoring model may be the same or similar only in structure, but may differ in parameter, such as a weighting or a filter value. In addition, the classification model of the first type is not necessarily realized in a structure that is the same as or similar to that of the monitoring model.

Referring to FIG. 19, the server may input a video 101 including image frames 102 and 103 to a classification model, may detect a medication-administration related object or a medication-administration related posture or both included in the image frames 102 and 103, and may define the category of the video 101 on the basis of the detection result. In this case, like the detection model described above, the classification model shown in FIG. 19 (hereinafter, referred to as a "classification model of a second type") may receive the image frames and detect a medication-administration related object or a medication-administration related posture or both included in the image frames. Accordingly, the classification model of the second type may be realized in a structure that is the same as or similar to that of the above-described detection model, and the details of the above-described detection model may be applied to the classification model of the second type. For example, second-type classification model output data that is output data of the classification model of the second type and the detection model output data described above may be the same or similar in format. Hereinafter, the difference between the classification model of the second type and the detection model will be mainly described.

The types of medication-administration related objects and postures detected by the classification model of the second type may include types that are different from the types of medication-administration related objects and postures detected by the detection model. The types of medication-administration related objects and postures detected by the detection model may include types that are different from the types of medication-administration related objects and postures detected by the classification model of the second type.

The classification model of the second type may detect medication-administration related objects, and the detection model may detect medication-administration related objects and medication-administration related postures. That is, the classification model of the second type may not detect medication-administration related postures. Herein, the types of medication-administration related objects detected by the classification model of the second type and the types of medication-administration related objects detected by the detection model may differ.

For example, the types of medication-administration related objects detected by the classification model of the second type may be more diverse than the types of medication-administration related objects detected by the detection model. As a specific example, a medication-administration related object detected by the classification model of the second type may be related to multiple types of medication administration, and a medication-administration related object detected by the detection model may be related to medication administration of a specific type among the multiple types. As a more specific example, the classification model of the second type may detect medication-administration related objects, such as a medicine bottle, an inhaler, a turbuhaler, and an eye dropper, related to multiple types of medication administration, and the detection model may detect a specific medication-administration related object, such as an inhaler, related to medication administration of a specific type, such as using an inhaler, among the multiple types. In this case, the detection model may detect one or more additional medication-administration related objects that the classification model of the second type does not detect. For example, the detection model may detect a body part in addition to an inhaler.

The classification model of the second type and the detection model may be the same or similar only in structure, but may differ in parameter, such as a weighting or a filter value. The classification model of the second type is not necessarily realized in a structure that is the same as or similar to that of the detection model.

The server may define the category of the video using medication-administration related objects and postures detected by the classification model of the second type. In this case, the server may determine the category index of the video using the second-type classification model output data.

A medication-administration related object and posture may have a category corresponding thereto.

Categories of medication-administration related objects and postures may be determined depending on types of medication administration related to the medication-administration related objects and postures. Medication-administration related objects and postures related to the same or similar types of medication administration may correspond to the same category. Medication-administration related objects and postures related to different types of medication administration may correspond to different categories. For example, referring to FIGS. 11 and 12, medication-administration related objects and postures, such as the medicine bottle 21, the pill 25, and the posture 36 for holding a pill, may correspond to a category related to a swallow of medicine. Medication-administration related objects and postures, such as the inhaler 26, and the posture 32 for holding an inhaler, may correspond to a category related to using an inhaler. Medication-administration related objects and postures, such as the turbuhaler 24, and the posture 33 for holding a turbuhaler, may correspond to a category related to using a turbuhaler. Medication-administration related objects and postures, such as the eye dropper 22, and the posture 34 for holding an eye dropper, may correspond to a category related to administration of an eyedrop. Medication-administration related objects and postures, such as the nasal spray 23, and the posture 35 for holding a nasal spray, may correspond to a category related to using a nasal spray. The description of such categories of medication-administration related objects and postures is only an example and is not limited thereto.

In some embodiments, the server may define the category of the video on the basis of the number of image frames from which a medication-administration related object or a medication-administration related posture or both are detected. In this case, the server may determine a category index of the video on the basis of the number of image frames from which a medication-administration related object or a medication-administration related posture or both are detected. For example, the server may calculate the number of image frames from which a medication-administration related object or a medication-administration related posture or both corresponding to a specific category are detected, and may define the category of the video on the basis of the calculated number. Specifically, the server may compare the number of image frames from which a medication-administration related object or a medication-administration related posture or both corresponding to a first category are detected, and the number of image frames from which a medication-administration related object or a medication-administration related posture or both corresponding to a second category are detected, and may define the category of the video as any one among the first category and the second category. Herein, the server may define the category of the video as the category with a large number of image frames, but no limitation thereto is imposed.

In some embodiments, the server may define the category of the video on the basis of the number of detected medication-administration related objects or detected medication-administration related postures or all. In this case, the server may determine a category index of the video on the basis of the number of medication-administration related objects or medication-administration related postures or all. For example, the server may calculate the number of medication-administration related objects or medication-administration related postures or all corresponding to a specific category in all image frames, and may define the category of the video on the basis of the calculated number. Specifically, the server may compare the number of medication-administration related objects or medication-administration related postures or all corresponding to a first category in all image frames, and the number of medication-administration related objects or medication-administration related postures or all corresponding to a second category in all image frames, and may define the category of the video as any one among the first category and the second category. Herein, the server may define the category of the video as the category with a large number of the objects or the postures or all, but no limitation thereto is imposed. In addition, in the case in which the number of medication-administration related objects is calculated, different parts of the same object may be regarded as one object or different objects. For example, the cap and the body of a medicine bottle may be regarded as one object and may be counted as one medication-administration related object, or may be regarded as two objects and may be counted as two medication-administration related objects. In particular, in the case in which different parts of a medication-administration related object are present physically separated, for example, the cap and the body of a medicine bottle are separated, the parts may be counted, being regarded as different objects.

In some embodiments, referring to FIG. 20, the server may define the category of the video using the second-type classification model output data and a classification model of a third type. For example, the server control unit may define the category of the video using the second-type classification model output data and the classification model of the third type. As another example, the server control unit may store the second-type classification model output data in the server storing unit, and may define the category of the video using the second-type classification model output data stored in the server storing unit and the classification model of the third type. Output data of the classification model of the third type may be a category index of the video.

The server may input the second-type classification model output data as it is to the classification model of the third type. In this case, input data input to the classification model of the third type may be the same as the second-type classification model output data. Alternatively, the server may transform the second-type classification model output data and input the resulting data to the classification model of the third type. In this case, input data input to the classification model of the third type may be generated on the basis of the second-type classification model output data. The details of generating the confirmation model input data on the basis of the detection result of the detection model described above may be applied to generating input data of the classification model of the third type on the basis of the second-type classification model output data, so a detailed description thereof will be omitted.

The classification model of the third type may be realized in a structure that is the same as or similar to that of the above-described confirmation model. However, even in this case, the classification model of the third type and the confirmation model may be the same or similar only in structure, but may differ in parameter, such as a weighting or a filter value. In addition, the classification model of the third type is not necessarily realized in a structure that is the same or similar to that of the confirmation model.

Referring back to FIG. 17, at step S330, the server may determine whether medication has been administered using the defined category and the video. The category may be a result of classification at step S320. The video may be obtained at step S310.

Figure 21:
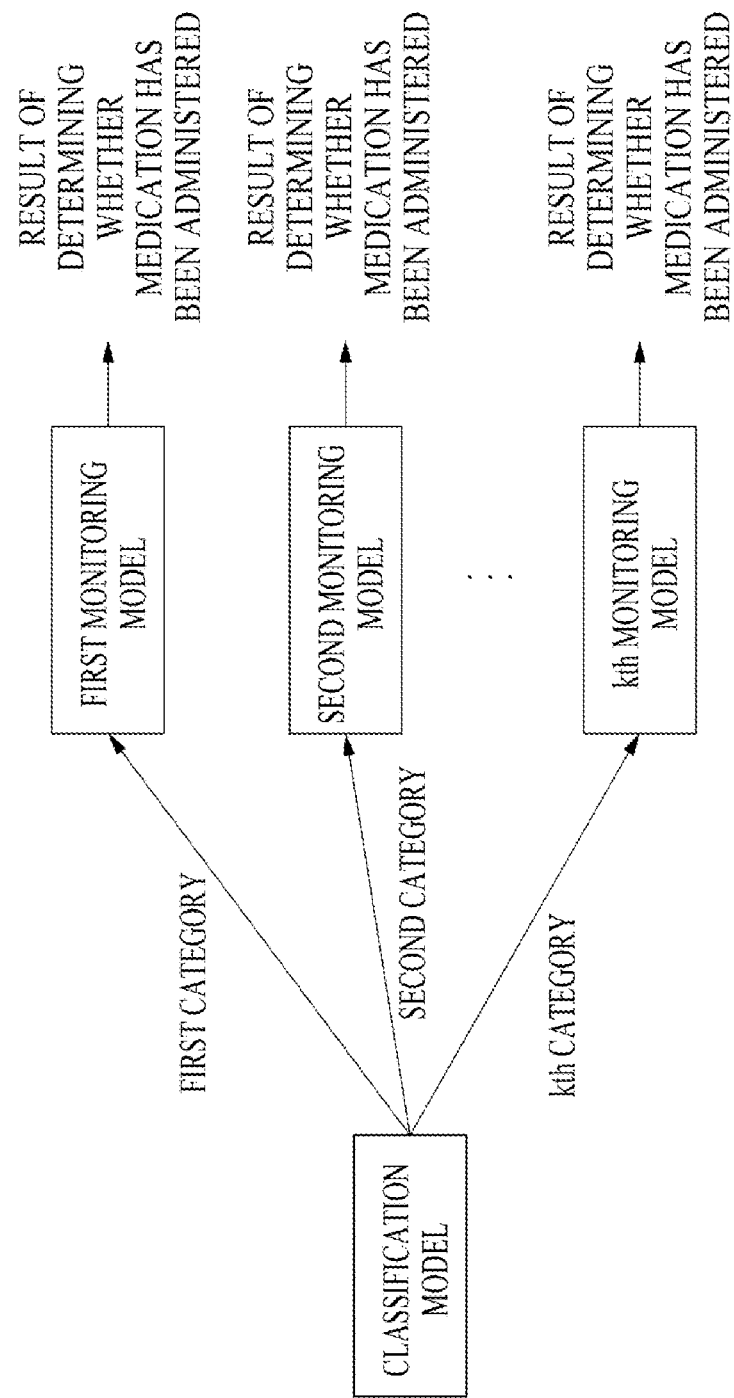
FIGS. 21 and 22 are diagrams illustrating determination of whether medication has been administered using categories resulting from classification and a video according to an embodiment.
Figure 22:
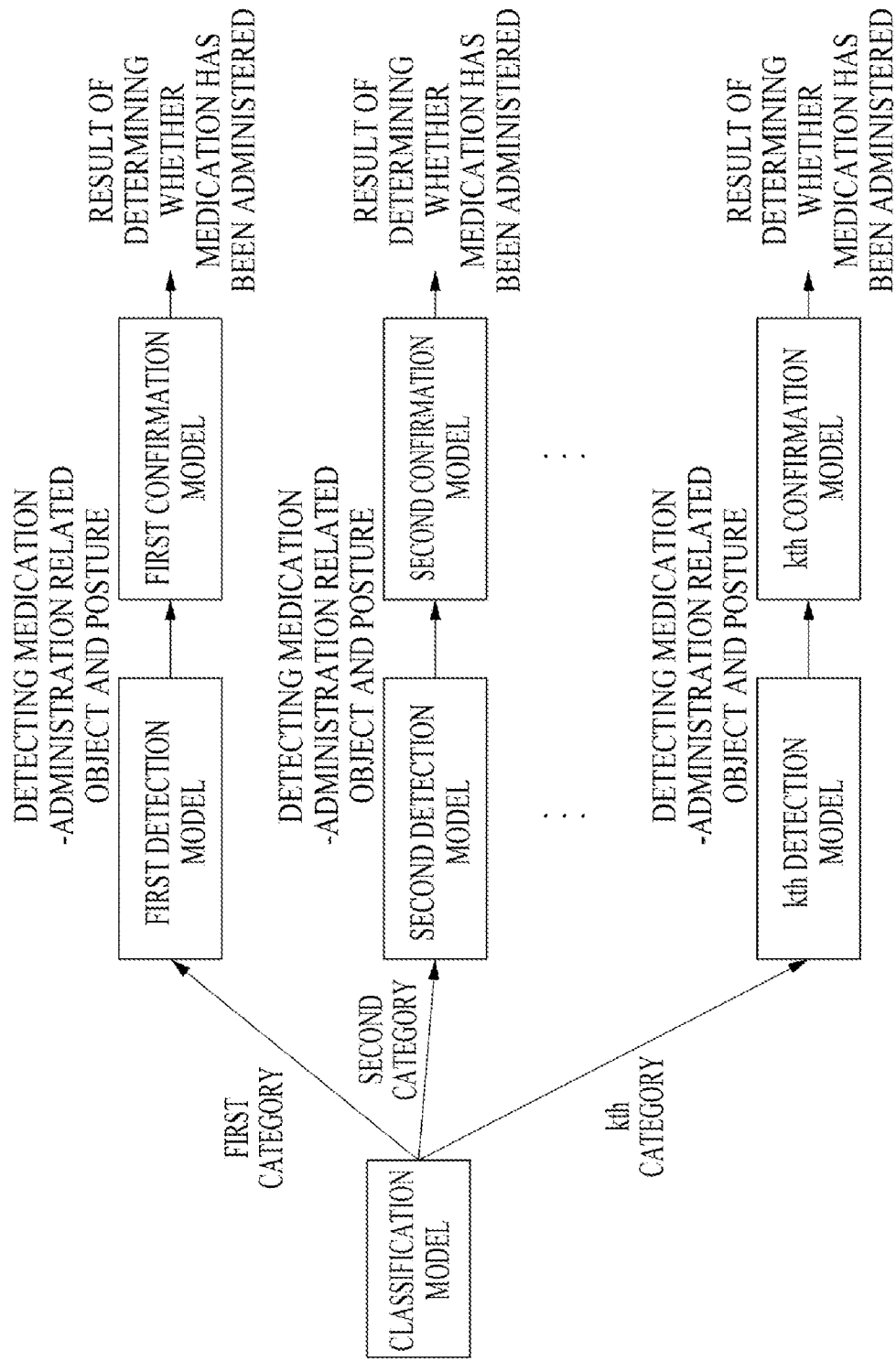

FIGS. 21 and 22 are diagrams illustrating determination of whether medication has been administered using categories resulting from classification and a video according to an embodiment. FIG. 21 shows a case of using a monitoring model as in 2.2 Method for Determining Whether Medication Has Been Administered Using Monitoring Model. FIG. 22 shows a case of using a detection model and a confirmation model as in 2.3 Method for Determining Whether Medication Has Been Administered Using Detection Model and Confirmation Model.

Referring to FIG. 21, the server may determine whether medication has been administered using a particular monitoring model for each category of the video. In this case, different monitoring models may determine whether different types of medication administration have been performed. For example, a first monitoring model corresponding to a first category may determine whether medication administration of a first type corresponding to the first category has been performed. A second monitoring model corresponding to a second category may determine whether medication administration of a second type corresponding to the second category has been performed. As a specific example, medication administration of a first type may be any one among a swallow of medicine, use of an inhaler, use of a turbuhaler, use of a nasal spray, administration of an eyedrop, and injection of medicine. Medication administration of a second type may be any one among a swallow of medicine, use of an inhaler, use of a turbuhaler, use of a nasal spray, administration of an eyedrop, and injection of medicine. No limitation thereto is imposed. The video input to the monitoring model may be the same as the video input to the classification model, but no limitation thereto is imposed.

Referring to FIG. 22, the server may determine whether medication has been administered using a particular detection model and a particular confirmation model for each category of the video. In this case, different detection models may detect different types of medication-administration related objects and postures. For example, a first detection model corresponding to a first category may detect a medication-administration related object and posture of a first type corresponding to the first category, and a second detection model corresponding to a second category may detect a medication-administration related object and posture of a second type corresponding to the second category. In addition, different confirmation models may determine whether different types of medication administration have been performed. For example, a first confirmation model corresponding to a first category may determine, on the basis of a medication-administration related object and posture of a first type corresponding to the first category, whether medication administration of the first type has been performed. A second confirmation model corresponding to a second category may determine, on the basis of a medication-administration related object and posture of a second type corresponding to the second category, whether medication administration of the second type has been performed. That is, the server may define a category of the video using the classification model, may detect a medication-administration related object and posture of a specific type using the detection model corresponding to the defined category, and may determine whether medication administration of the specific type has been performed using the confirmation model corresponding to the defined category. The video input to the detection model may be the same as the video input to the classification model, but no limitation thereto is imposed.

Although FIG. 22 shows that detection models and confirmation models are different for respective categories of videos, the detection models or the confirmation models may be the same. For example, detection models may be different for respective categories of videos, but confirmation models may be the same. As another example, detection models may be the same for respective categories of videos, but confirmation models may be different.

In addition, although FIGS. 21 and 22 show the case in which a video is classified into k categories, three or more categories, but a video may be classified into two categories.

Although defining, by the server, a category of a video using the classification model has been described, a method of defining a category of a video is not limited thereto. For example, the server may define a category of the video on the basis of data indicating the category of the video. Specifically, the server may receive the data from the outside, such as the wireless communication device or the wearable device, and may define a category of the video. In this case, the server may receive the data from the outside, such as the wireless communication device or the wearable device, and may determine a category index of the video.

The above-described method for determining whether medication has been administered, with the monitoring model, the detection model, the confirmation model, and the classification model in combination is only an example. Whether medication has been administered may be determined with such models in combination differently from the above-described examples. In addition, whether medication has been administered may be determined with at least some of the above-described models and other models in combination.

2.5 Model Training Method

Hereinafter, a method of training the above-described models will be described. A case in which the models are deep learning models will be described, but no limitation thereto is imposed.

Figure 23:
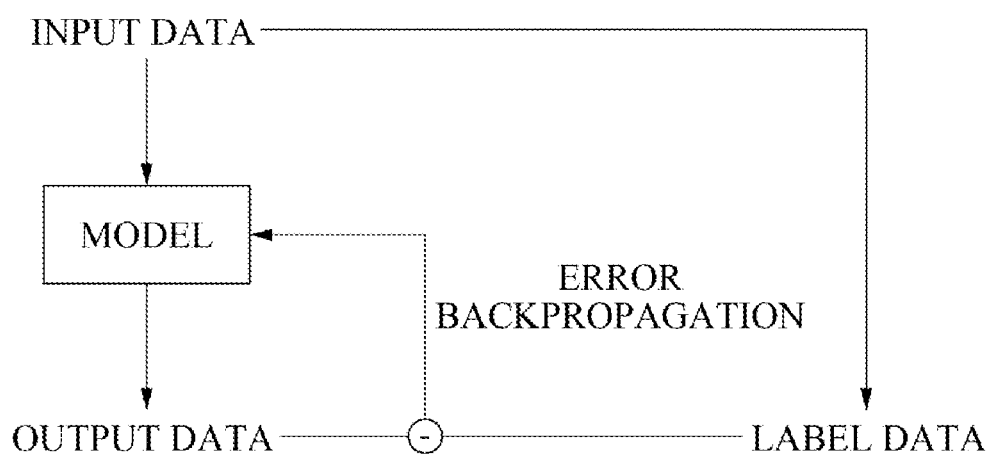
FIG. 23 is a diagram illustrating a method of training a model according to an embodiment.

FIG. 23 is a diagram illustrating a method of training a model according to an embodiment, which shows supervised learning. The server may train a model using training data. The training data may include input data and label data. The input data and the label data may correspond to each other. The server may input the input data to a model for which training is not completed, to acquire output data, and may compare the output data and the label data to train the model through error backpropagation. The server training the model may be the same as the server determining whether medication has been administered using the model, or may be a particular training server for training the model.

The server may prepare the training data. For example, the server may generate the training data. As a specific example, the server may receive input data and generate label data on the basis of the input data. As another example, the server may acquire the training data from the outside. As a specific example, the server may receive the training data generated by an external device, or may receive the training data generated by a person.

A model may be trained using various training techniques, such as Optimizer Adam, SGDScheduler, Random Contrast, Random Hue, Random Brightness, Random Flip left right, Random Crop, and Random Resize.

2.5.1 Method of Training Monitoring Model

The server may train a monitoring model. The server may train the monitoring model using monitoring model training data for training the monitoring model.

The monitoring model training data may include a training video and monitoring model label data of the training video, wherein the monitoring model label data indicates whether medication has been administered. The format of the training video may be the same as the above-described format of the video input to the monitoring model when whether medication has been administered is determined. In addition, the format of the monitoring model label data may be the same as the above-described format of the index indicating whether medication has been administered.

The training video may include a training video of medication administration and a training video of medication non-administration.

The monitoring model label data may include: a label corresponding to the training video of medication administration and indicating medication administration; and a label corresponding to the training video of medication non-administration and indicating medication non-administration. Alternatively, the monitoring model label data may include: a label indicating the probability that medication administration is estimated; and a label indicating the probability that medication non-administration is estimated.

Referring to FIG. 23, input data, label data, and output data shown in FIG. 23 may be a training video, monitoring model label data, and an index indicating whether medication has been administered, respectively. The server may input the training video to the monitoring model for which training is not completed, to acquire the index indicating whether medication has been administered, and may compare the index indicating whether medication has been administered and the monitoring model label data to train the monitoring model through error backpropagation.

2.5.2 Method of Training Detection Model

The server may train a detection model. The server may train the detection model using detection model training data for training the detection model.

The detection model training data may include a training image frame and detection model label data, wherein the detection model label data is related to a medication-administration related object or a medication-administration related posture or both included in the training image frame. The format of the training image frame may be the same as the above-described format of the image frame input to the detection model when whether medication has been administered is determined. In addition, the format of the detection model label data may be the same as the above-described format of the detection model output data.

The detection model label data may include label data of a medication-administration related object (hereinafter, referred to as "object label data") and label data of a medication-administration related posture (hereinafter, referred to as "posture label data").

The object label data may include labels for various types of medication-administration related objects, which are used by the user for medication administration. As a non-limiting example, the object label data may include a medicine bottle label, an eye dropper label, a nasal spray label, a turbuhaler label, a pill label, an inhaler label, a blister pack label, and a syringe label.

The object label data may include a label for a body part. As a non-limiting example, the object label data may include an arm label, a hand label, a wrist label, a palm label, an outer-part-of-palm label, a face label, a mouth label, and a nose label.

The posture label data may include various types of medication-administration related postures, such as positioning of the user for medication administration. As a non-limiting example, the posture label data may include: labels of postures for holding medication-administration related objects, such as a label of the posture for holding a blister pack, a label of the posture for holding an inhaler, a label of the posture for holding a turbuhaler, a label of the posture for holding an eye dropper, a label of the posture for holding a nasal spray, and a label of the posture for holding a pill; a label of the posture for swallowing medicine such as a pill; labels of postures for inhaling medicine using medication-administration related objects, such as an inhaler, a turbuhaler, and a nasal spray; a label of the posture for administering an eyedrop using a medication-administration related object such as an eye dropper; a label of the posture for injecting medicine using a medication-administration related object such as a syringe; and a label of the posture for opening a medication-administration related object such as a medicine bottle.

Hereinafter, more detailed examples of the detection model training data will be described.

FIGS. 24 to 28 are diagrams illustrating detection model training data according to an embodiment, which conceptually show detection model label data in training image frames.

Figure 24:
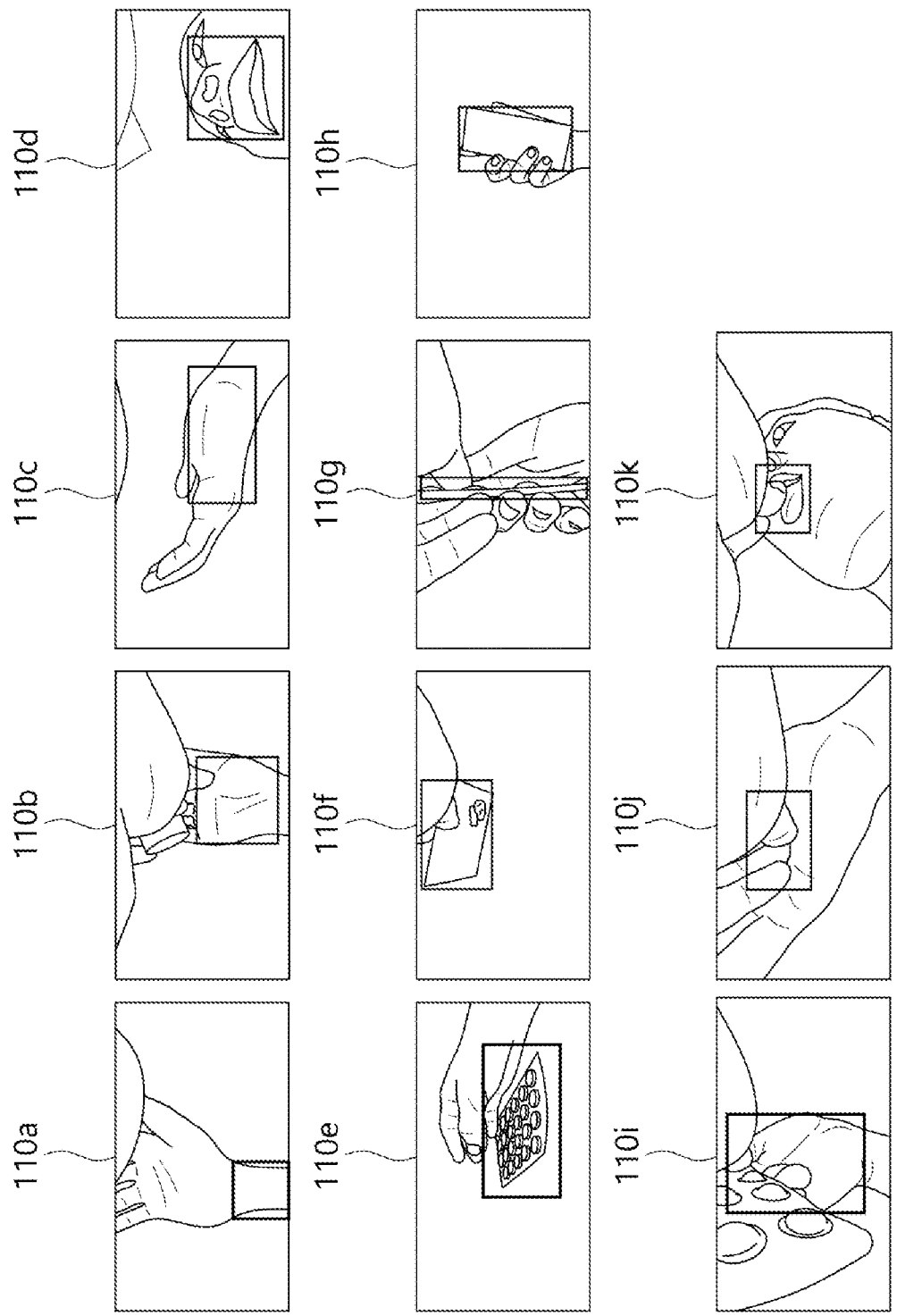
FIGS. 24 to 28 are diagrams illustrating detection model training data according to an embodiment.

FIG. 24 is a diagram illustrating an example of detection model training data related to a swallow of medicine using a blister pack among medical supplies. Referring to FIG. 24, the object label data may include: labels for a body, such as an arm label 110a, a palm label 110b, an outer-part-of-palm label 110c, and a face label (or a mouth-nose label) 110d; and labels for a blister pack, such as a blister-pack-top label 110e, a blister-pack-bottom label 110f, a blister-pack-side label 110g, and a blister pack box label 110h. The posture label data may include a label 110i of the posture for holding a blister pack, a label 110j of the posture for holding a pill, and a label 110k of the posture for swallowing a pill.

Figure 25:
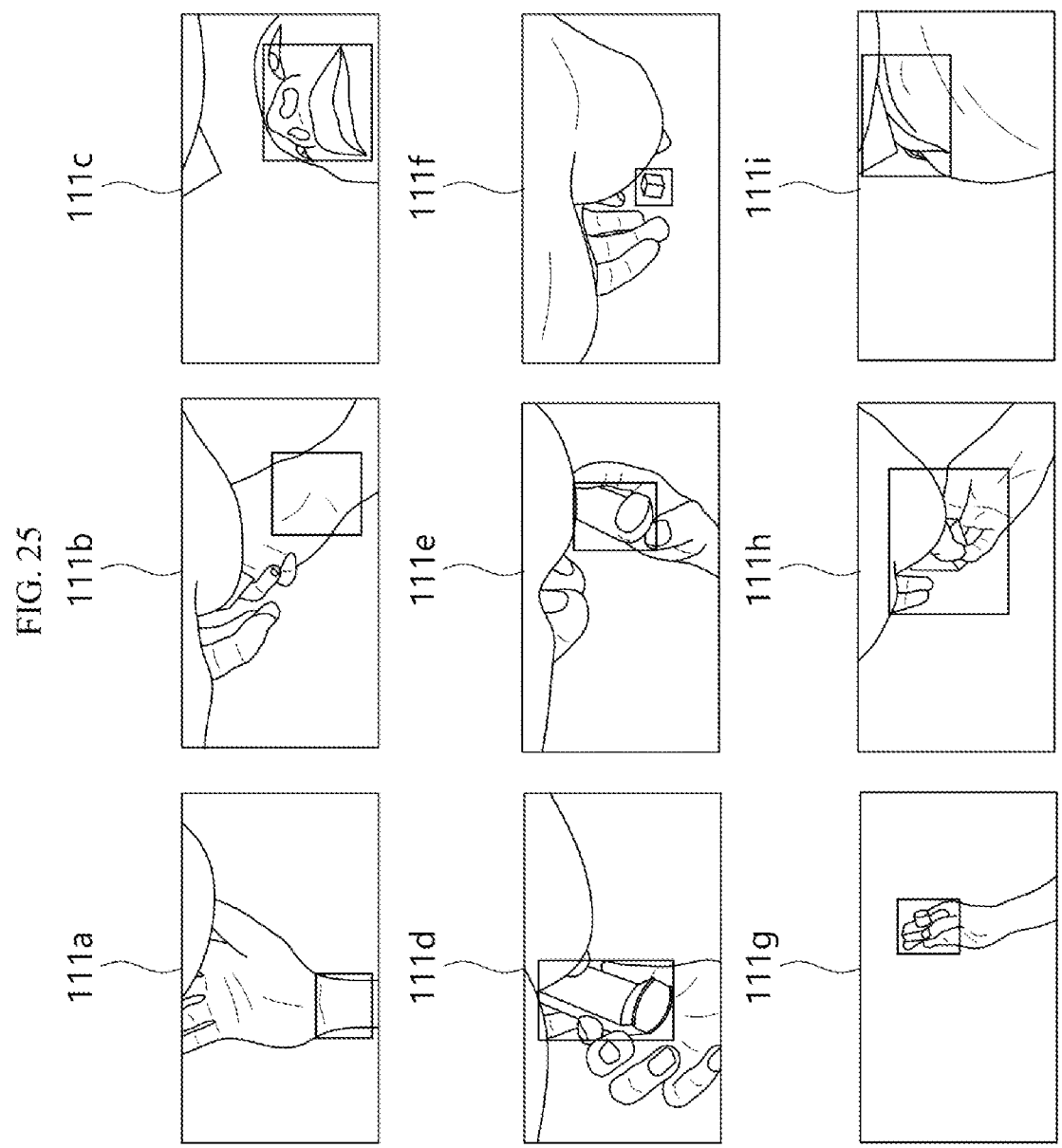

FIG. 25 is a diagram illustrating an example of detection model training data related to inhalation of medicine using an inhaler among medical supplies. Referring to FIG. 25, the object label data may include: labels for a body, such as an arm label 111a, a wrist label 111b, and a face label (or a mouth-nose label) 111c; and labels for an inhaler, such as an inhaler label 111d, an opened-inhaler label 111e, and an inhaler cap label 111f The posture label data may include a label 111g of the posture for holding an inhaler, a label 111h of the posture for opening an inhaler, and a label 111i of the posture for inhaling with an inhaler.

Figure 26:
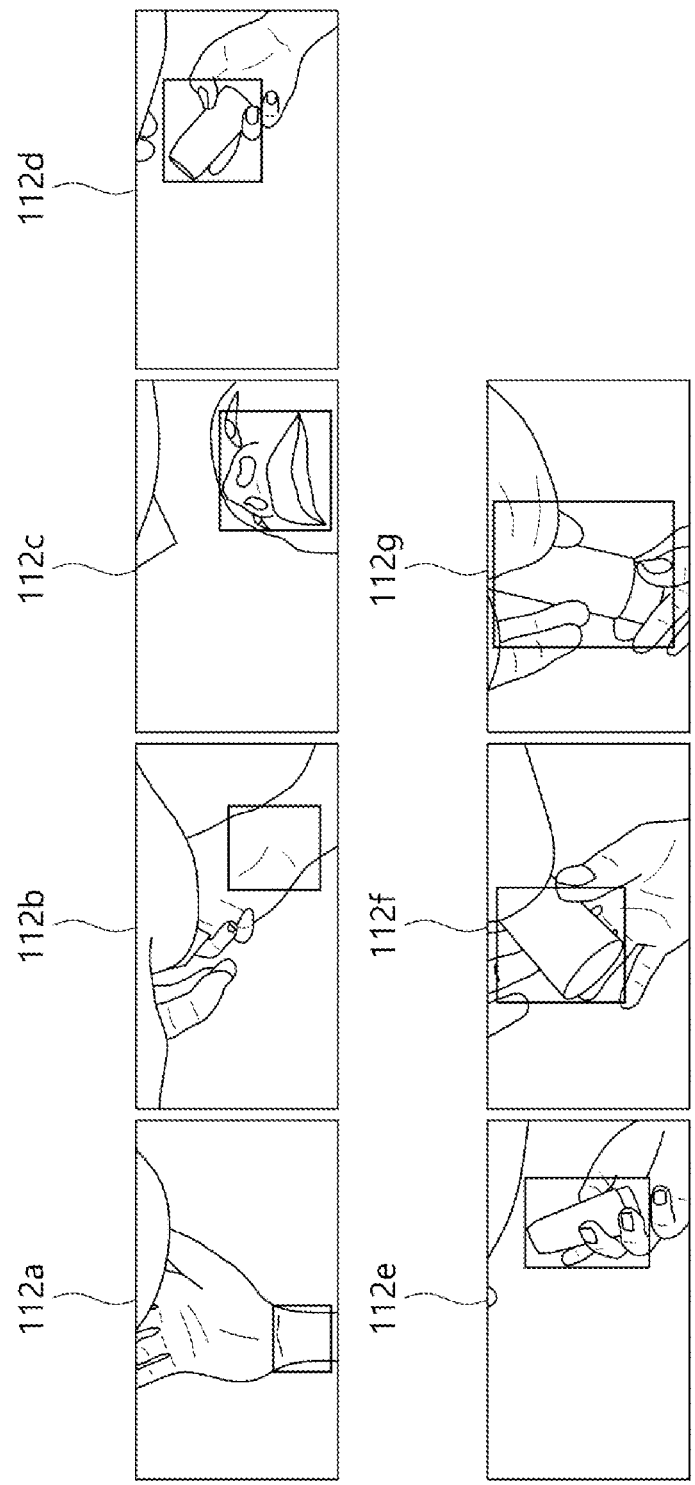

FIG. 26 is a diagram illustrating an example of detection model training data related to inhalation of medicine using a turbuhaler among medical supplies. Referring to FIG. 26, the object label data may include: labels for a body, such as an arm label 112a, a wrist label 112b, and a face label (or a mouth-nose label) 112c; and labels for a turbuhaler, such as a turbuhaler label 112d, an opened-turbuhaler label 112e, and a turbuhaler cap label 112f The posture label data may include a label 112g of the posture for holding a turbuhaler.

Figure 27:
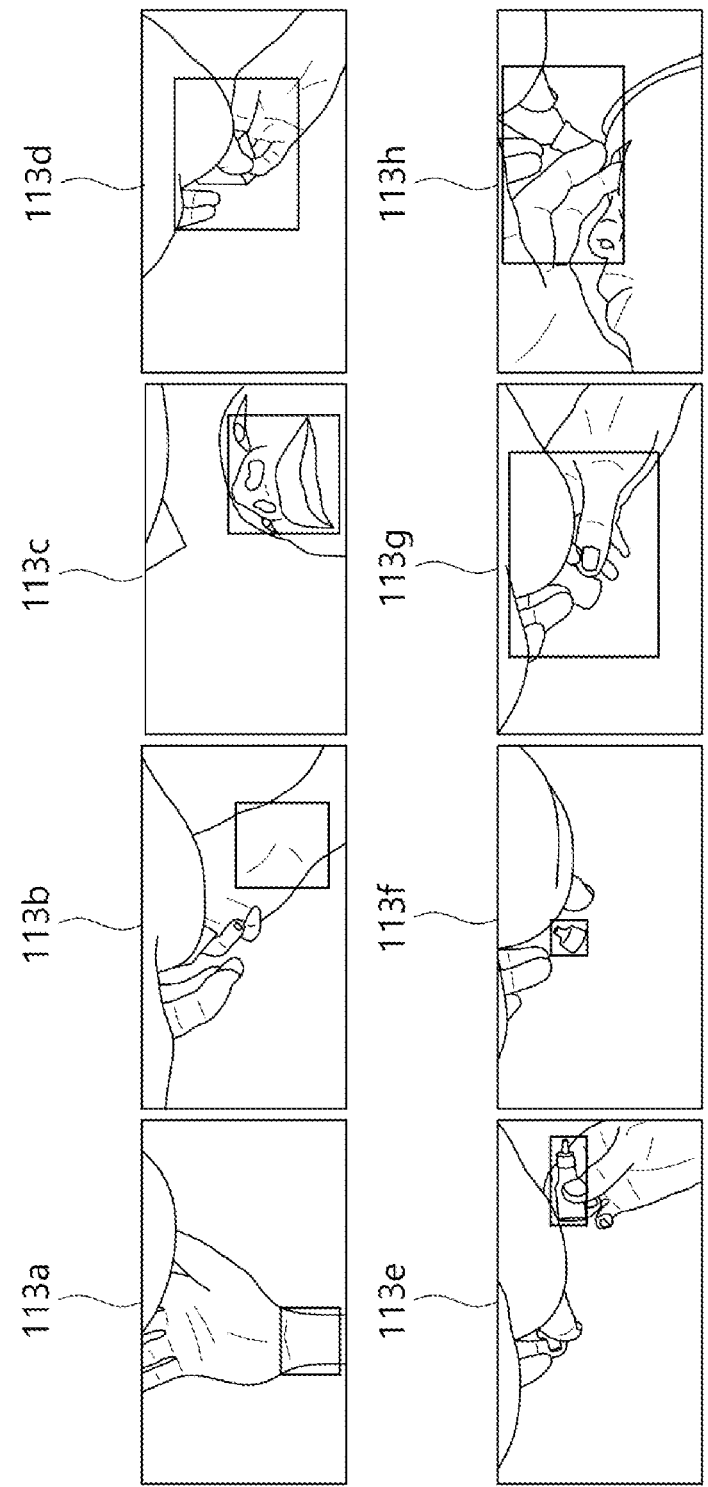

FIG. 27 is a diagram illustrating an example of detection model training data related to administration of an eyedrop using an eye dropper among medical supplies. Referring to FIG. 27, the object label data may include: labels for a body, such as an arm label 113a, a wrist label 113b, and a face label (or a mouth-nose label) 113c; and labels for an eye dropper, such as an eye dropper label 113d, an opened-eye-dropper label 113e, and an eye dropper cap label 113f The posture label data may include a label 113g of the posture for holding an eye dropper, and a label 113h of the posture for administering an eyedrop.

Figure 28:
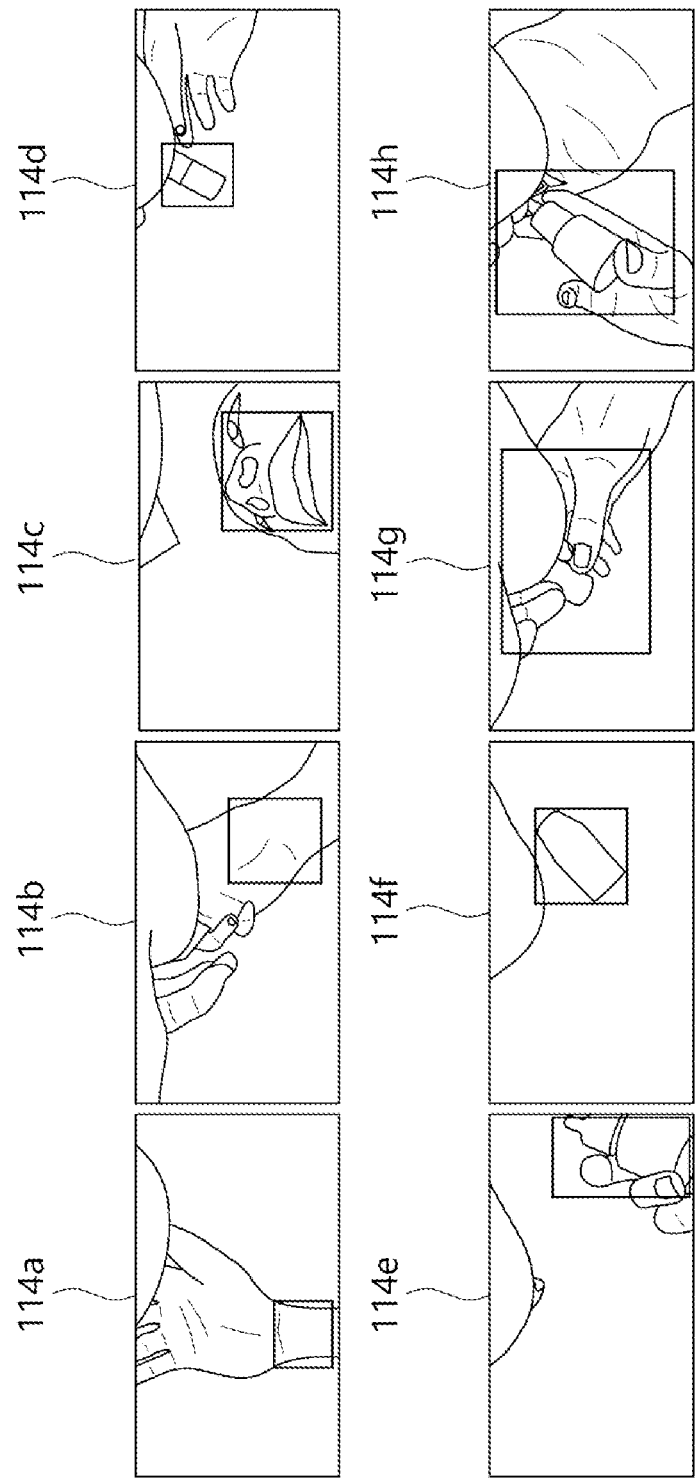

FIG. 28 is a diagram illustrating an example of detection model training data related to inhalation of medicine using a nasal spray among medical supplies. Referring to FIG. 28, the object label data may include: labels for a body, such as an arm label 114a, a wrist label 114b, and a face label (or a mouth-nose label) 114c; and labels for a nasal spray, such as a nasal spray label 114d, an opened-nasal-spray label 114e, and a nasal spray cap label 114f The posture label data may include a label 114g of the posture for holding a nasal spray, and a label 114h of the posture for spraying with a nasal spray.

Referring to FIGS. 24 to 28, depending on a type of medication administration or a type of medical supply, the detection model label data related thereto may include different labels. For example, detection model label data related to a swallow of medicine using a blister pack may include: the labels 110e, 110f, 110g, and 110h for a blister pack; the label 110i of the posture for holding a blister pack; the label 110j of the posture for holding a pill; and the label 110k of the posture for swallowing a pill. Detection model label data related to inhalation of medicine using an inhaler may include: the labels 111d, 111e, and 111f for an inhaler; the label 111g of the posture for holding an inhaler; the label 111h of the posture for opening an inhaler; and the label 111i of the posture for inhaling with an inhaler.

Even the types of medication administration or the types of medical supplies differ, the detection model label data related thereto may include the same label. For example, all of medication administration shown in FIGS. 24 to 28 includes the arm labels 110*a*, 111*a*, 112*a*, 113*a*, and 114*a*, and the face labels 110*d*, 111*c*, 112*c*, 113*c*, and 114*c*.

Depending on a medication-administration related object or a medication-administration related posture or both detected by the detection model, detection model training data used when the detection model is trained may vary.

Depending on a type of medication administration to be determined by the server, detection model training data used when the detection model is trained may vary. For example, in the case of the detection model that is used to determine whether medication administration using a blister pack has been performed, the server may train the detection model using the detection model training data as shown in FIG. 24. In the case of the detection model that is used to determine whether medication administration using a blister pack has been performed and whether inhalation of medicine using an inhaler has been performed, the server needs to train the detection model using the detection model training data as shown in FIG. 24 as well as the detection model training data as shown in FIG. 25. That is, the more various the types of medication administration to be determine d are, the more types of detection model training data the server uses to train the detection model.

The detection model training data shown in FIGS. 24 to 28 is only an example, so the detection model training data is not limited thereto. The detection model training data may further include a label not shown in FIGS. 24 to 28. In addition, at least some of the labels of the detection model training data shown in FIGS. 24 to 28 may be omitted.

Referring back to FIG. 23, input data, label data, and output data shown in FIG. 23 may be a training image frame, detection model label data, and detection model output data, respectively. The server may input the training image frame to the detection model for which training is not completed, to acquire the detection model output data, and may compare the detection model output data and the detection model label data to train the detection model through error backpropagation.

2.5.3 Method of Training Confirmation Model

The server may train a confirmation model. The server may train the confirmation model using confirmation model training data for training the confirmation model.

The confirmation model training data may include confirmation model input data for training and confirmation model label data that corresponds to the confirmation model input data for training and indicates whether medication has been administered. The format of the confirmation model input data for training may be the above-described format of the confirmation model input data. In addition, the format of the confirmation model label data may be the same as the above-described format of the index indicating whether medication has been administered.

The confirmation model input data for training may include confirmation model input data for training which represents medication administration and confirmation model input data for training which represents medication non-administration.

The confirmation model input data for training may be generated on the basis of a video. The confirmation model input data for training may incorporate a medication-administration related object or a medication-administration related posture or both included in the video. The confirmation model input data for training which represents medication administration may be generated on the basis of a training video of medication administration. The confirmation model input data for training which represents medication non-administration may be generated on the basis of a training video of medication non-administration.

The confirmation model label data may include a label indicating medication administration and a label indicating medication non-administration. Alternatively, the confirmation model label data may include: a label indicating the probability that medication administration is estimated; and a label indicating the probability that medication non-administration is estimated.

Referring to FIG. 23, input data, label data, and output data shown in FIG. 23 may be confirmation model input data for training, confirmation model label data, and an index indicating whether medication has been administered, respectively. The server may input the confirmation model input data for training to the confirmation model for which training is not completed, to acquire the index indicating whether medication has been administered, and may compare the index indicating whether medication has been administered and the confirmation model label data to train the monitoring model through error backpropagation.

2.5.4 Method of Training Classification Model

The server may train a classification model.

In the case of the classification model of the first type, the server may train the classification model of the first type using first-type classification model training data for training the classification model of the first type.

The first-type classification model training data may include a training video and first-type classification model label data indicating the category of the training video (or indicating the probability that the category is estimated). The format of the training video may be the same as the above-described format of the video input to the classification model of the first type when whether medication has been administered is determined. In addition, the format of the first-type classification model label data may be the same as the above-described format of the index indicating the category (or an index indicating the probability that the category is estimated).

The training video may include multiple videos corresponding to different categories. As a non-limiting example, the training video may include: a video corresponding to the category of a swallow of medicine; a video corresponding to the category of use of an inhaler; a video corresponding to the category of use of a turbuhaler; a video corresponding to the category of administration of an eyedrop; and a video corresponding to the category of use of a nasal spray.

The training video may include a training video of medication administration and a training video of medication non-administration.

The first-type classification model label data may include multiple labels corresponding to different categories. For example, the first-type classification model label data may include: a label corresponding to the category of a swallow of medicine; a label corresponding to the category of use of an inhaler; a label corresponding to the category of use of a turbuhaler; a label corresponding to the category of administration of an eyedrop; and a label corresponding to the category of use of a nasal spray.

Referring to FIG. 23, input data, label data, and output data shown in FIG. 23 may be a training video, first-type classification model label data, and an index indicating a category (or an index indicating the probability that a category is estimated), respectively. The server may input the training video to the classification model of the first type for which training is not completed, to acquire the index indicating the category (or the index indicating the probability that the category is estimated), and may compare the index indicating the category (or the index indicating the probability that the category is estimated) and the first-type classification model label data to train the classification model of the first type through error backpropagation.

In the case of the classification model of the second type, the server may train the classification model of the second type using second-type classification model training data for training the classification model of the second type.

The second-type classification model training data may include a training image frame and second-type classification model label data, wherein the second-type classification model label data is related to a medication-administration related object or a medication-administration related posture or both included in the training image frame. The format of the training image frame may be the same as the above-described format of the image frame input to the classification model of the second type when whether medication has been administered is determined. In addition, the format of the second-type classification model label data may be the same as the above-described format of the second-type classification model output data.

The second-type classification model label data may include the object label data or the posture label data or both described above.

The second-type classification model label data may include a label of a type that is different from a label of a type that the detection model label data includes. The detection model label data may include a label of a type that is different from a label of a format that the second-type classification model label data includes.

The second-type classification model label data may include the object label data, and the detection model label data may include the object label data and the posture label data. That is, the second-type classification model label data may not include the posture label data. Herein, the object label data of the second-type classification model label data may include a label of a type that is different from a label of a type that the object label data of the detection model label data includes. For example, the object label data of the second-type classification model label data may include a label related to multiple types of medication administration, and the object label data of the detection model label data may include a label related to medication administration of a specific type among the multiple types. As a specific example, the object label data of the second-type classification model label data may include labels, such as the medicine bottle label, the inhaler label, the turbuhaler label, and the eye dropper label, related to multiple types of medication administration, and the detection model label data may include the inhaler label that is a label related to medication administration of a specific type that is use of an inhaler. In this case, the object label data of the detection model label data may include an additional label that the object label data of the second-type classification model label data does not include. For example, in addition to the inhaler label, the object label data of the detection model label data may include a label for a body part.

Referring to FIG. 23, input data, label data, and output data shown in FIG. 23 may be a training image frame, second-type classification model label data, and second-type classification model output data, respectively. The server may input the training image frame to the classification model of the second type for which training is not completed, to acquire the second-type classification model output data, and may compare the second-type classification model output data and the second-type classification model label data to train the classification model of the second type through error backpropagation.

In the case of the classification model of the third type, the server may train the classification model of the third type using third-type classification model training data for training the classification model of the third type.

The third-type classification model training data may include third-type classification model input data for training and third-type classification model label data indicating the category corresponding to the third-type classification model input data for training (or indicating the probability that the category is estimated). The format of the third-type classification model input data for training may be the same as the above-described format of the input data input to the classification model of the third type when whether medication has been administered is determined. In addition, the format of the third-type classification model label data may be the same as the above-described format of the output data of the classification model of the third type.

The third-type classification model input data for training may include multiple input data corresponding to different categories. As anon-limiting example, the third-type classification model input data for training may include: input data corresponding to the category of a swallow of medicine; input data corresponding to the category of use of an inhaler; input data corresponding to the category of use of a turbuhaler; input data corresponding to the category of administration of an eyedrop; and input data corresponding to the category of use of a nasal spray.

The third-type classification model input data for training may include input data representing medication administration and input data representing medication non-administration. The details of the first-type classification model label data described above may be applied to the third-type classification model label data, so a redundant description thereof will be omitted.

Referring to FIG. 23, input data, label data, and output data shown in FIG. 23 may be third-type classification model input data for training, third-type classification model label data, and an index indicating a category (or an index indicating the probability that a category is estimated), respectively. The server may input the third-type classification model input data for training to the classification model of the third type for which training is not completed, to acquire the index indicating the category (or the index indicating the probability that the category is estimated), and may compare the index indicating the category (or the index indicating the probability that the category is estimated) and the third-type classification model label data to train the classification model of the third type through error backpropagation.

The above-described training methods are only example and not limited thereto. The models may be trained through other methods, such as unsupervised learning, reinforcement learning, and imitation learning.

2.5.5 Model Training Sequence

The above-described models may be trained in association with each other.

In some embodiments, in the case in which whether medication has been administered is determined using the detection model and the confirmation model, the server may train one of the two models first and train the other. For example, the server may train the detection model first and train the confirmation model. As a specific example, the server may train the detection model first using the detection model training data, may then connect the detection model and the confirmation model, and may train the confirmation model using the training image frame of the detection model training data again. In this case, the data input to the confirmation model to train the confirmation model may be generated on the basis of the detection model output data. In addition, when the confirmation model is trained, the already trained detection model is trained again or is not trained.

In some embodiments, in determining whether medication has been administered using the classification model of the first type and the monitoring model, when the classification model of the first type and the monitoring model are the same in structure, the server trains one of the two models first and trains the other second.

In some embodiments, in determining whether medication has been administered using the classification model of the second type, the detection model, and the confirmation model, when the classification model of the second type and the detection model are the same in structure, the server trains one of the two models first and trains the other second.

The above-described models may be trained independently. For example, in the case in which whether medication has been administered is determine d using the detection model and the confirmation model, the server may train the detection model and the confirmation model independently. As a specific example, the server may train the detection model using the detection model training data, and separately, the server may train the confirmation model using the confirmation model training data. Herein, any one among the detection model and the confirmation model may be trained first.

2.6 Embodiments and Results

2.6.1 First Embodiment

FIG. 29 is a diagram illustrating a first embodiment that is an example of a method for determining whether medication has been administered using a monitoring model, which relates to a result of determining whether medication has been administered using a monitoring model. In FIG. 29, it was determined whether oral administration of a pill poured out of a medicine bottle had been performed, which is a swallow of medicine among various types of medication administration. As the monitoring model, ResNet101-based I3D network and ResNet50-based SlowFast network were used. In FIG. 29, a training video including 100 training image frames was used in training the monitoring model, and each of the training image frames had a resolution of 224×224 pixels. Referring to FIG. 29, in the case of using I3D network as the monitoring model, the accuracy of determining whether a swallow of medicine had been performed was in a range of 77.8 to 81% depending on training methods. In addition, in the case of using SlowFast network as the monitoring model, the accuracy of determining whether a swallow of medicine had been performed was in a range of 74 to 80% depending on training methods. In the case of the monitoring model, it was found that the accuracy was a maximum of about 80% regardless of types of networks. However, the first embodiment is a result of training using about 1200 training videos. The accuracy shown in FIG. 29 may vary depending on a case, for example, the accuracy is improved as training is performed, or the accuracy is improved as a training video is changed.

2.6.2 Second Embodiment

Figure 31:
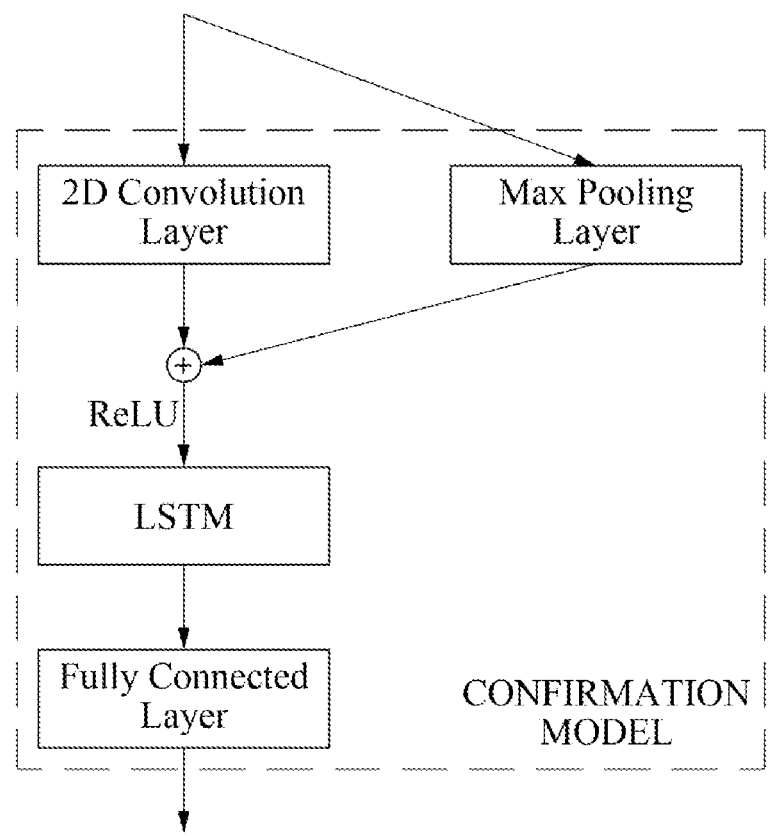

FIGS. 30 and 31 are diagrams illustrating a second embodiment that is an example of a method for determining whether medication has been administered using a detection model and a confirmation model, which relates to a result of determining whether medication has been administered using a detection model and a confirmation model. In FIG. 30, it was determine d whether oral administration of a pill poured out of a medicine bottle had been performed, which is a swallow of medicine among various types of medication administration. Version 2 relates to a case in which additional training was performed with supplemented training data after initial training (Version 1). As the detection model, ResNet101-based Faster R-CNN was used, and as the confirmation model, a combination of 2D convolution layer and LSTM was used. Describing the structure of the confirmation model in more detail with reference to FIG. 31, confirmation model input data input to the confirmation model is concatenated after passing through a 2D convolution layer and a max pooling layer, passes through ReLU, LSTM, and a fully connected layer, and is output as a result of determining whether medication has been administered. However, the structure of the confirmation model shown in FIG. 31 is illustrative, so the structure of the confirmation model is not limited thereto. For example, unlike the confirmation model of which a 2D convolution layer, LSTM, and a fully connected layer are designed in that order as shown in FIG. 31, the confirmation model may be designed in this order: LSTM, a 2D convolution layer, and a fully connected layer.

Referring back to FIG. 30, the accuracy of the detection model was 85.1% for initial training and was 88.8% for additional training. In addition, the accuracy of the confirmation model was 90.5% for initial training and was 94.5% for additional training. It was found that the accuracies of the models were improved as training data was supplemented. In addition, it was found that the case of using the detection model and the confirmation model had an improved accuracy of determining whether medication had been administered, compared to the first embodiment, which is the case of using the monitoring model as shown in FIG. 29. However, the accuracy shown in FIG. 30 may vary depending on a case, for example, the accuracy is improved as training is performed, or the accuracy is improved as a training video is changed.

2.6.3 Third Embodiment

FIG. 32 is a diagram illustrating a third embodiment that is an example of a method for determining whether medication has been administered using a classification model, which relates to a result of determining whether medication has been administered using a classification model and a monitoring model. In FIG. 32, it was determined whether medication had been administered, with respect to the following among various types of medication administration: oral administration of a pill poured out of a medicine bottle, which is a swallow of medicine; inhalation of medicine using an inhaler; and oral administration of a pill pressed out of a blister pack, which is a swallow of medicine. In FIG. 32, the case in which the model type is the monitoring model refers to the case in which whether medication had been administered was determined using only the monitoring model without using the classification model with respect to the three types of medication administration. The case in which the model type is the classification model+the monitoring model refers to the case in which whether medication had been administered was determined using the classification model and the monitoring model together with respect to the three types of medication administration. Herein, the monitoring model in the case of not using the classification model is a model capable of determining whether medication has been administered, with respect to the three types of medication administration. The monitoring model in the case of using the classification model is a model capable of determining whether medication has been administered, with respect to one specific type of medication administration among the three types of medication administration. That is, when the classification model was not used, one monitoring model was used, and when the classification model was used, three monitoring models were used.

Referring to FIG. 32, in the case of using only the monitoring model without using the classification model, it was found that with respect to the three types of medication administration, whether medication had been administered was determined with an accuracy of 60.1%. Conversely, in the case of using the classification model and the monitoring model together, it was found that whether medication had been administered was determined with the following accuracies: an accuracy of 77% for oral administration of a pill poured out of a medicine bottle, which is a swallow of medicine; an accuracy of 78.4% for inhalation of medicine using an inhaler; and an accuracy of 83.9% for oral administration of a pill pressed out of a blister pack, which is a swallow of medicine. It was found that whether medication had been administered was determined with an average accuracy of 79.8%. It is believed that when the classification model was used, the reason why the monitoring model related to a blister pack determined whether medication had been administered, with a high accuracy is that a hyperparameter optimized therefor was used in training the monitoring model related to the medicine bottle and the monitoring model related to the inhaler. However, the accuracy shown in FIG. 32 may vary depending on a case, for example, the accuracy is improved as training is performed, or the accuracy is improved as a training video is changed.

2.7 Additional Examples of Method for Determining Whether Medication Has Been Administered Hereinafter, some additional examples of method for determining whether medication has been administered will be described.

2.7.1 First Additional Example—Main Hand and Sub Hand

As described above, the server may determine whether medication has been administered, on the basis of a video acquired from a wearable device. Herein, in the case in which a video is generated by a wearable device worn on either a left part or a right part of the user's body (for example, a smart watch, a smart band, or a smart ring), a video generated when medication is administered using the body part on which the wearable device is worn and a video generated when medication is administered using the body part on which the wearable device is not worn may have different aspects. For example, in generating a video with a camera unit provided in a smart watch, a video generated when medication is administered using the hand wearing the smart watch and a video generated when medication is administered using the hand not wearing the smart watch may have different aspects. Hereinafter, the case in which the wearable device is a smart watch will be mainly described. The hand wearing a wearable device is referred to as a main hand and the hand not wearing the wearable device is referred to as a sub hand. For example, when a smart watch is worn on the left wrist, the left hand is a main hand and the right hand is a sub hand.

As described above, the medication administration patterns may vary between users. In terms of the main hand and the sub hand, for example, some users may administer medication using the main hands, and differently from the medication administration pattern of the some users, other users may administer medication using the sub hands.

In addition, as described above, even the same user may have different medication administration patterns depending on a case. In terms of the main hand and the sub hand, for example, the user may administer medication using the main hand at this time, but differently from the medication administration pattern at this time, the user may administer medication using the sub hand at the next time.

In the meantime, the user may administer medication using the main hand and the sub hand together depending on a case. For example, the user may hold a pill with the sub hand, may place the pill on the palm of the main hand, and may move the main hand to his/her mouth to swallow the pill. In this case, it may be unclear whether medication has been administered using the main hand or the sub hand. In addition, even in this case, the medication administration patterns of the user may vary depending on a case. For example, the user has swallowed a pill as described above at this time, but the user may swallow a pill in a different pattern at the next time, for example, the user holds a pill with the main hand, places the pill on the palm of the sub hand, and move the sub hand to his/her mouth to swallow the pill.

Herein, between the main hand and the sub hand, medication administration may be regarded as having been performed using the hand with which a main stage of medication administration has been performed. For example, when a main stage of medication administration has been performed with the main hand, medication administration is regarded as having been performed using the main hand. Main stages of medication administration may vary according to a type of medication administration. For example, in the case of swallowing a pill, a stage of moving a pill to his/her mouth to swallow the pill may be the main stage of medication administration. As another example, in the case of use of an inhaler, a stage of moving an inhaler to his/her mouth to inhale may be the main stage of medication administration. As still another example, in the case of use of a turbuhaler, a stage of moving a turbuhaler to his/her mouth to inhale may be the main stage of medication administration. As still another example, in the case of use of a nasal spray, a stage of moving a nasal spray to the nose to inhale may be the main stage of medication administration. As still another example, in the case of administration of an eyedrop, a stage of moving an eye dropper to the eye to administer an eyedrop may be the main stage of medication administration. As still another example, in the case of injection of medicine, a stage of moving a syringe to a part of the body for injection may be the main stage of medication administration. The main stages of medication administration depending on the types of medication administration described above are only examples, and may vary depending on a case without being limited thereto.

Alternatively, between the main hand and the sub hand, medication administration may be regarded as having been performed using the hand with which more stages of the entire medication administration process have been performed.

Hereinafter, medication administration that is regarded as having been performed using the main hand, for example, at least the main stage of medication administration has been performed using the main hand, or most parts of medication administration have been performed using the main hand, is referred to as medication administration in which the main hand is a subject. In addition, medication administration that is regarded as having been performed using the sub hand, for example, at least the main stage of medication administration has been performed using the sub hand, or most parts of medication administration have been performed using the sub hand, is referred to as medication administration in which the sub hand is a subject.

Depending on whether the user has administered medication using the main hand as a subject or using the sub hand as a subject, behaviors of the user may differ. Accordingly, different behaviors may be captured in a video representing the medication administration in which the main hand is a subject (hereinafter, referred to as a "main-hand video") and in a video representing the medication administration in which the sub hand is a subject (hereinafter, referred to as a "sub-hand video").

Figure 33:
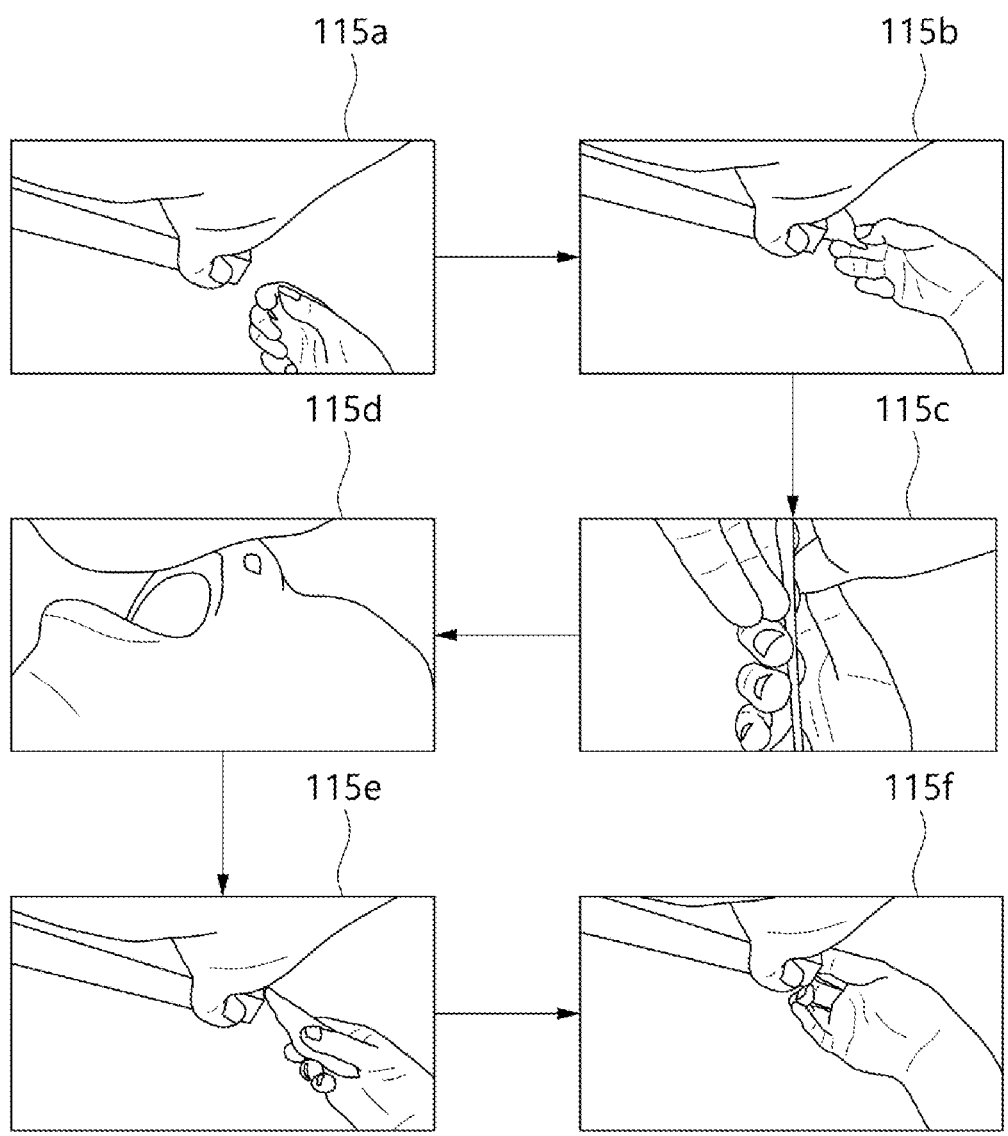
FIGS. 33 and 34 are diagrams illustrating medication administration in which a main hand is a subject and medication administration in which a sub hand is a subject, respectively, according to an embodiment.
Figure 34:
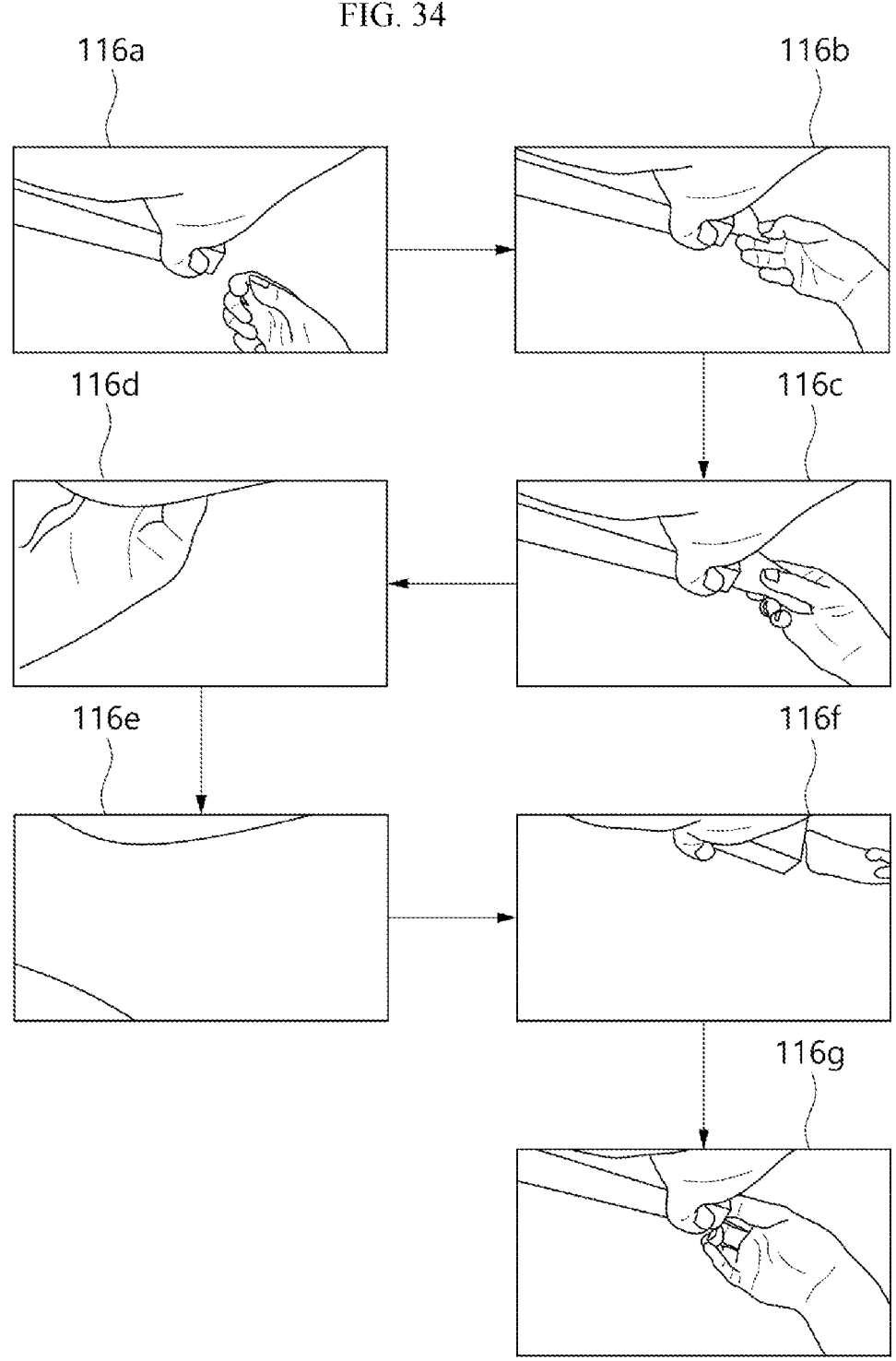

FIGS. 33 and 34 are diagrams illustrating the medication administration in which the main hand is a subject and the medication administration in which the sub hand is a subject, respectively, according to an embodiment, which relates to a swallow of medicine using a blister pack. FIGS. 33 and 34 show image frames of a video generated by a smart watch, which is a wearable device, of which a camera unit is provided to be located on the inner side of the wrist when the user wears the smart watch.

The same or similar behaviors may be captured in the main-hand video and the sub-hand video. For example, referring to FIGS. 33 and 34, both the main-hand video and the sub-hand video include the followings captured therein: behaviors 115a and 116a of the user holding a blister pack box; behaviors 115b and 116b of the user taking a blister pack out of the blister pack box; behaviors 115c and 116c of the user pressing a pill out of the blister pack; behaviors 115e and 116f of the user putting the blister pack into the blister pack box; and behaviors 115f and 116g of the user closing the blister pack box.

However, depending on a case, a behavior captured in one among the main-hand video and the sub-hand video may not be captured in the other. For example, referring to FIGS. 33 and 34, the behavior 115d of the user swallowing a pill is captured in the main-hand video, but is not captured in the sub-hand video (and a behavior 116e is captured therein). In addition, the behavior 116d of the user holding a pill is captured in the sub-hand video, but is not captured in the main-hand video. That is, the behaviors of the user captured in the main-hand video and the sub-hand video may differ, and even in this situation, the server needs to be capable of determining whether medication has been administered, on the basis of a video. Therefore, a model trained considering this needs to be provided.

The server may determine whether medication has been administered using a model trained using both the main-hand video and the sub-hand video. For example, a training video of the monitoring model training data may include the main-hand video and the sub-hand video. Alternatively, training image frames of the detection model training data may include image frames of the main-hand video and image frames of the sub-hand video. Alternatively, the confirmation model input data for training of the confirmation model training data may include input data corresponding to the main-hand video and input data corresponding to the sub-hand video. Alternatively, a training video (or training image frames) of the classification model training data may include the main-hand video (or image frames of the main-hand video) and the sub-hand video (or image frames of the sub-hand video). In this case, the server may determine whether medication has been administered, as medication administration or medication non-administration. Even in the case in which the server trains a model using both the main-hand video and the sub-hand video, the training methods described in 2.5 Model Training Method may be applied identically or similarly.

In addition to using both the main-hand video and the sub-hand video, the server may determine whether medication has been administered using a model that is trained to determine whether medication has been administered, by distinguishing the medication administration in which the main hand is a subject and the medication administration in which the sub hand is a subject. In this case, the server does not determine whether medication has been administered, as medication administration or medication non-administration, but determines whether medication has been administered, as the medication administration in which the main hand is a subject, as the medication administration in which the sub hand is a subject, or as medication non-administration.

For example, in the case in which whether medication has been administered is determined using the monitoring model, a training video of the monitoring model training data includes the main-hand video and the sub-hand video and the monitoring model label data includes: a label corresponding to the main-hand video and indicating the medication administration in which the main hand is a subject (hereinafter, referred to as a "main hand label"); and a label corresponding to the sub-hand video and indicating the medication administration in which the sub hand is a subject (hereinafter, referred to as a "sub hand label").

As another example, in the case in which whether medication has been administered is determined using the detection model and the confirmation model, training image frames of the detection model training data include image frames of the main-hand video and image frames of the sub-hand video and the confirmation model label data of the confirmation model training data may include the main hand label and the sub hand label.

Even in the case in which the server trains a model to determine whether medication has been administered, by distinguishing the medication administration in which the main hand is a subject and the medication administration in which the sub hand is a subject, the training methods described in 2.5 Model Training Method may be applied identically or similarly.

FIG. 35 is a diagram illustrating a result of determining whether medication has been administered, depending on whether the medication administration in which the main hand is a subject and the medication administration in which the sub hand is a subject are distinguished, according to an embodiment. FIG. 35 shows determination of whether medication has been administered using the detection model and the confirmation model. In FIG. 35, it was determined whether oral administration of a pill poured out of a medicine bottle had been performed, which is a swallow of medicine among various types of medication administration. As the detection model, ResNet101-based Faster R-CNN was used, and as the confirmation model, a combination of 2D convolution layer and LSTM was used (see FIG. 31). Referring to FIG. 35, it was found that the validation accuracy and the test accuracy of the case in which whether medication had been administered was determined distinguishing the medication administration in which the main hand was a subject and the medication administration in which the sub hand was a subject were 98.8% and 96.8%, respectively. The validation accuracy and the test accuracy were higher than the validation accuracy of 97.7% and the test accuracy of 88.8% of the case in which whether medication had been administered was determine d not distinguishing the medication administration in which the main hand was a subject and the medication administration in which the sub hand was a subject. That is, compared to the case in which whether medication has been administered is determined not distinguishing the medication administration in which the main hand is a subject and the medication administration in which the sub hand is a subject, the case in which whether medication has been administered is determined distinguishing the medication administration in which the main hand is a subject and the medication administration in which the sub hand is a subject may accurately determine whether medication has been administered.

The server may train a model first using any one among the main-hand video and the sub-hand video and may train the model using the other one. Alternatively, the server may train a model using the main-hand video and the sub-hand video alternately. Alternatively, the server may train a model using the main-hand video and the sub-hand video without a particular nie of sequence.

The server may use a model for determining whether medication administration in which the main hand is a subject has been fulfilled and a model for determining whether medication administration in which the sub hand is a subject has been fulfilled.

2.7.2 Second Additional Example—Omission of Some of Medication Administration Process The server may determine whether medication has been administered, by checking in real time whether the user has performed a specific behavior for each step of medication administration. For example, the server may determine whether medication has been administered, by checking whether the user holds a pill, whether the user puts the pill into his/her mouth, and whether the user swallows the pill, through the video or images step by step. In this case, since it is checked whether the user has performed a specific behavior for each step, no specific steps are omitted, which may be advantageous in determining whether medication has been administered. However, the user needs to perform an unnatural specific behavior so that whether medication has been administered is determined, which is inconvenient for the user.

Unlike this, the server may determine whether medication has been administered, without requesting the user to perform a particular specific behavior. That is, even though the user administers medication as usual, the server may analyze a video thereof and determine whether medication has been administered. However, in this case, it is not checked in real time whether the user has performed a specific behavior for each step, so a specific stage of medication administration may not be captured in the video depending on the user's positioning or the time taken for medication administration. Herein, the server needs to determine whether medication has been administered using a video of medication administration of which some of a medication administration process is omitted. In particular, in the case of taking a video for a predetermine d time and determining whether medication has been administered, when the user administers medication for a time longer than the predetermine d time, a latter part of the medication administration process is not captured in the video. For example, in the case of oral administration of a pill poured out of a medicine bottle, which is a swallow of medicine, the behavior of the user pouring a pill out of a medicine bottle or the behavior of the user holding the pill, which are the former parts of the medication administration process, may be captured in the video, but the behavior of the user swallowing the pill, which is the latter part of the medication administration process, may not be captured in the video. Alternatively, when the camera unit is activated later than the time when the user starts medication administration, the former (earlier) part of the medication administration process is not captured in the video. For example, when the camera unit is activated at the time when the user swallows a pill, the behavior of the user pouring the pill out of the medicine bottle or the behavior of the user holding the pill is not captured in the video. Even in the cases of such exceptional situations, the server is required to be capable of determining whether medication has been administered, so a model considering this needs to be provided.

Figure 36:
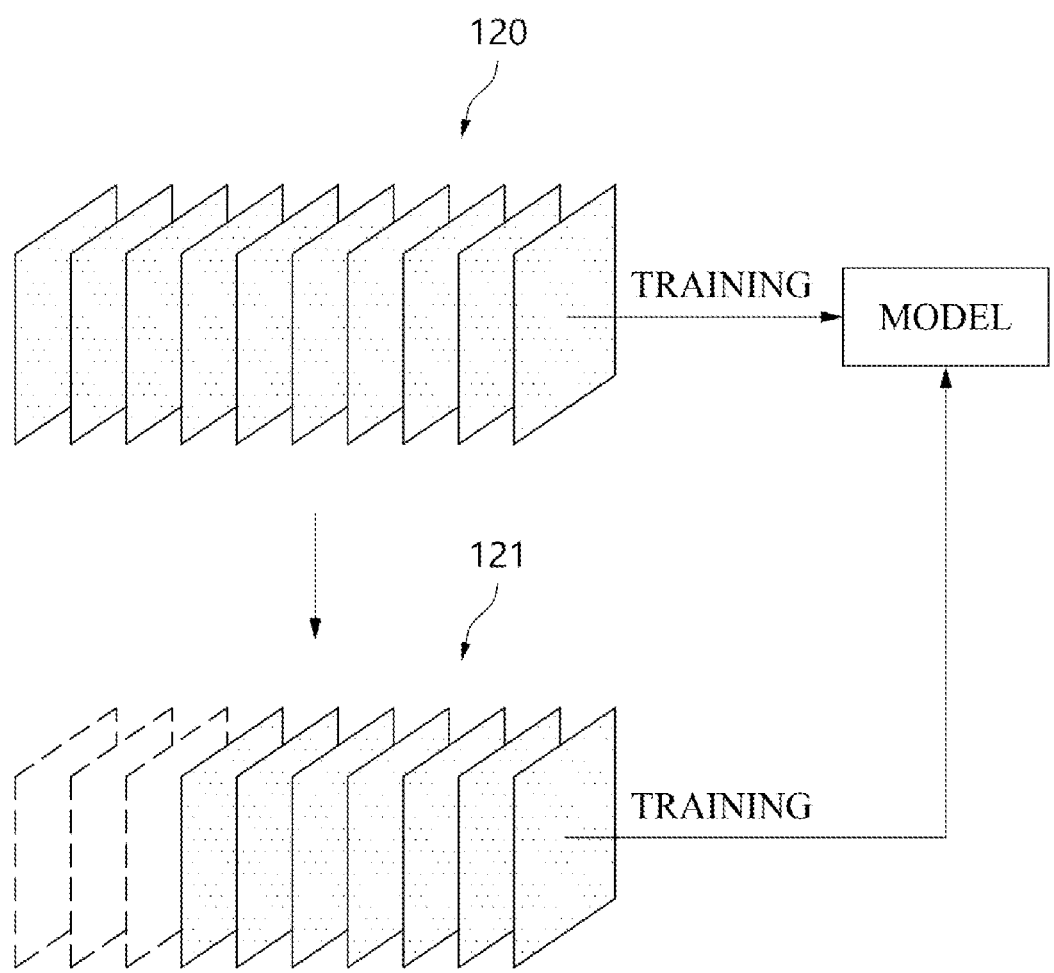
FIG. 36 is a diagram illustrating model training using a video of which some image frames are removed, according to an embodiment.

FIG. 36 is a diagram illustrating model training using a video of which some image frames are removed, according to an embodiment. Referring to FIG. 36, the server may train a model using a training video 120 including all image frames and a training video 121 of which some image frames are removed. The model may be a model for which input data is a video, such as the monitoring model, and the classification model of the first type.

Referring to FIG. 36, the training video 121 of which some image frames are removed may be generated on the basis of the training video 120 including all image frames.

Figure 37:
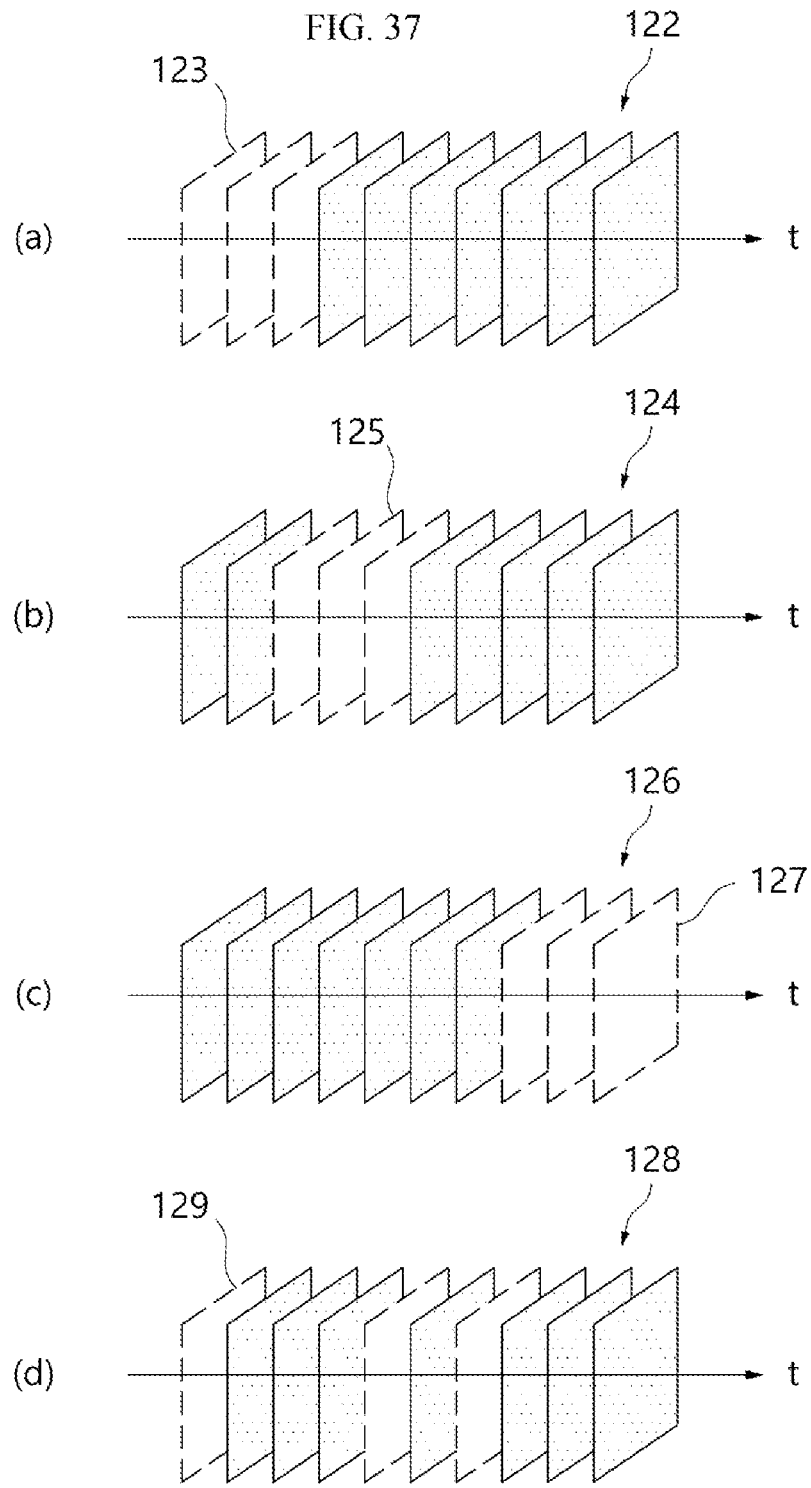
FIG. 37 is a diagram illustrating a method of removing some image frames of a training video, according to an embodiment.

FIG. 37 is a diagram illustrating a method of removing some image frames of a training video, according to an embodiment.

Referring to (a) to (c) of FIG. 37, training videos 122, 124, and 126 of which some image frames are removed may be training videos of which a predetermine d number of consecutive image frames 123, 125, and 127 are removed among all image frames of the training videos, respectively. Herein, the removed consecutive image frames may be the former part 123 of the training video as shown in (a) of FIG. 37, may be the middle part 125 of the training video as shown in (b) of FIG. 37, or may be the latter part 127 of the training video as shown in (c) of FIG. 37. In the case in which all image frames of a training video include the entire medication administration process, the training video of which an image frame corresponding to the former part is removed may be regarded as the case in which the former part of the medication administration process is not captured. Similarly, the training video of which an image frame corresponding to the middle part may be regarded as the case in which the middle part of the medication administration process is not captured. The training video of which an image frame corresponding to the latter part is removed may be regarded as the case in which the latter part of the medication administration process is not captured. That is, since the server trains a model using a training video of which consecutive image frames are removed, even though some stages of medication administration are not captured in a video, the server determines whether medication has been administered using the video.

Referring to (d) of FIG. 37, a training video 128 of which some image frames are removed may be a training video of which a predetermine d number of image frames 129 are randomly removed among all image frames of the training video.

The description of the removal of some image frames of a training video shown in FIG. 37 is only an example and is not limited thereto.

Even though some image frames of a training video are removed, the server may need to add data to the removed parts because the format of data input to a model is fixed. In this case, the server may add an image frame having a predetermined pixel value to the positions of the removed image frames. For example, all pixels of the added image frames may have the same pixel values, but are not limited thereto. That is, the above-described training video of which some image frames are removed may include the same number of image frames as the training video including all image frames, wherein information (for example, information on a pixel value) on the removed image frames is lost in the training video. Alternatively, the server may add an image frame having a predetermined pixel value to a position different from the positions of the removed image frames. For example, as shown in (a) of FIG. 37, even though the former part 123 of the training video is removed, the server adds image frames having a predetermined pixel value to the latter part of the training video. As another example, as shown in (c) of FIG. 37, even though the latter part 127 of the training video is removed, the server adds image frames having a predetermined pixel value to the former part of the training video.

The server may train a model first using any one among a training video of which some image frames are removed and a training video including all image frames, and may train the model using the other. For example, the server may train a model first using a training video of which some image frames are removed, and may train the model using a training video including all image frames. Alternatively, the server may train a model using a training video of which some image frames are removed and a training video including all image frames alternately. Alternatively, the server may train a model using a training video of which some image frames are removed and a training video including all image frames, without a particular rule of sequence.

Unlike the monitoring model or the classification model of the first type, the confirmation model does not use a video as input data, so the case of the confirmation model will be described below.

Figure 38:
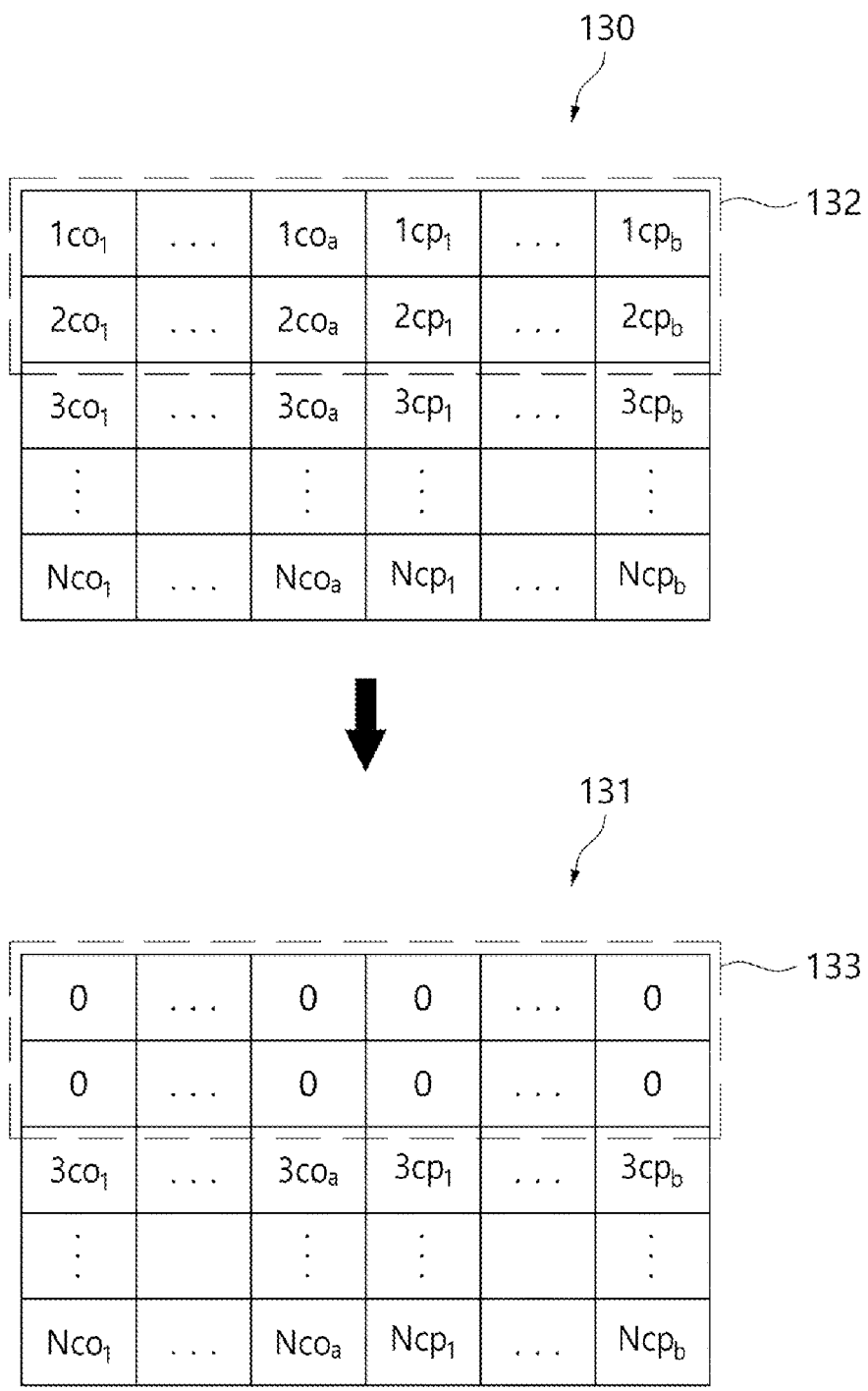
FIG. 38 is a diagram illustrating a method of removing some sub data of confirmation model input data for training, according to an embodiment.

FIG. 38 is a diagram illustrating a method of removing some sub data of confirmation model input data for training, according to an embodiment. As described above, the confirmation model input data includes sub data, and each piece of the sub data may correspond to an image frame. Therefore, similarly to the case in which some image frames of a training video are removed as shown in FIGS. 36 and 37, a situation in which some sub data of the confirmation model input data for training are removed and some of the medication administration process is omitted may be considered.

Referring to FIG. 38, confirmation model input data 131 for training of which some sub data are removed may be confirmation model input data for training of which some sub data 132 are removed from confirmation model input data 130 for training including all sub data. Similarly to the case in which some image frames of a training video are removed as shown in FIG. 37, the removed sub data of the confirmation model input data for training may correspond to consecutive image frames or random image frames. In addition, in removing sub data of the confirmation model input data for training corresponding to consecutive image frames, sub data corresponding to the image frames of the former part, middle part, or latter part may be removed.

Similarly to the removal of some image frames of a training video, even though some sub data of the confirmation model input data for training are removed, the server may need to add data to the removed part because the format of data input to the confirmation model is fixed. In this case, referring to FIG. 38, the server may add sub data 133 having a predetermined value (for example, 0 in FIG. 38) to the position of the removed sub data. In addition, the above-described confirmation model input data for training of which some sub data are removed may include the same number of sub data as the confirmation model input data for training including all sub data, wherein information on the removed sub data is lost in the confirmation model input data for training.

The description of the removal of some sub data of the confirmation model input data for training shown in FIG. 38 is only an example and is not limited thereto.

The server may train the confirmation model first using any one among the confirmation model input data for training of which some sub data are removed and the confirmation model input data for training including all sub data, and may train the confirmation model using the other. For example, the server may train the confirmation model first using the confirmation model input data for training of which some sub data are removed, and may train the confirmation model using the confirmation model input data for training including all sub data. Alternatively, the server may train the confirmation model using the confirmation model input data for training of which some sub data are removed and the confirmation model input data for training including all sub data, alternately. Alternatively, the server may train the confirmation model using the confirmation model input data for training of which some sub data are removed and the confirmation model input data for training including all sub data, without a particular rule of sequence.

A model may be trained using a label smoothing technique. In this case, the server may determine more accurately whether medication has been administered. In particular, the server may determine more accurately whether medication has been administered, with respect to a video in which some of the medication administration process is omitted.

FIG. 39 is a diagram illustrating a model that is trained considering a situation in which some of a medication administration process is omitted, according to an embodiment, which relates to a result of determining whether medication has been administered, by the detection model and the confirmation model trained using the confirmation model input data for training of which some sub data are removed. Confirmation model 1 was a confirmation model that was trained using only the confirmation model input data for training including all sub data. Confirmation model 2 was a confirmation model that was trained using both the confirmation model input data for training of which some sub data were removed and the confirmation model input data for training including all sub data. Fundamentally, in model training, a 20-second video having the frame rate of 30 fps (so, the number of all image frames was 600) was used. That is, the confirmation model input data for training of which the number of all sub data was 600 was used. Among this, 200 consecutive pieces of sub data were removed to generate the confirmation model input data for training of which some sub data were removed. As the detection model, ResNet101-based Faster R-CNN was used, and as the confirmation model, a combination of 2D convolution layer and LSTM was used for both Confirmation models 1 and 2 (see FIG. 31).

Referring to FIG. 39, in the case of using Confirmation model 1 for a video of the entire medication administration process, the server determined whether medication had been administered, with an accuracy of 96.5%. In the case of using Confirmation model 2 for the video, the server determined whether medication had been administered, with an accuracy of 99.8%. In the case of using Confirmation model 1 for a video of medication administration in which some of the medication administration process was omitted, the server determine d whether medication had been administered, with an accuracy of 83.7%. In the case of using Confirmation model 2 for the video, the server determined whether medication had been administered, with an accuracy of 95.8%. That is, compared to the case of using the confirmation model that was trained using only the confirmation model input data for training including all sub data, the case of using the confirmation model that was trained using both the confirmation model input data for training of which some sub data were removed and the confirmation model input data for training including all sub data had an improved accuracy. In particular, for the video of medication administration in which some of the medication administration process was omitted, the accuracy of determining whether medication had been administered was improved. In other words, it was found that in the case of training a model using a training video of which some image frames were removed or the corresponding confirmation model input data for training of which some sub data were removed, the accuracy of determining whether medication had been administered was improved for the video of the medication administration in which some of the medication administration process was omitted.

FIG. 40 is a diagram illustrating removal of consecutive image frames and removal of random image frames according to an embodiment, which relates to a result of determining whether medication has been administered, by the detection model and the confirmation model trained using the confirmation model input data for training of which some sub data are removed. Confirmation model 3 was a confirmation model that was trained using the confirmation model input data for training of which consecutive sub data were removed and the confirmation model input data for training including all sub data. Confirmation model 4 was a confirmation model that was trained using the confirmation model input data for training of which random sub data were removed and the confirmation model input data for training including all sub data. The detection model and the confirmation model in the same structure as those in FIG. 39 were used. The number of all sub data and the number of removed sub data of the confirmation model input data for training were the same as those in FIG. 39.

Referring to FIG. 40, in the case of using Confirmation model 3 for a video of the entire medication administration process, the server determined whether medication had been administered, at an accuracy of 98.9%. In the case of using Confirmation model 4 for the video, the server determined whether medication had been administered, at an accuracy of 99.3%. In the case of using Confirmation model 3 for a video of medication administration in which some of the medication administration process was omitted, the server determined whether medication had been administered, an accuracy of 93.1%. In the case of using Confirmation model 4 for the video, the server determined whether medication had been administered, at an accuracy of 90.0%. That is, regardless of the method of removing sub data, for the video of the entire medication administration process, whether medication had been administered was determined at similar accuracy; however, for the video of medication administration in which some of the medication administration process was omitted, the using of the confirmation model trained using the confirmation model input data for training of which consecutive sub data were removed was advantageous to improve the accuracy of determining whether medication had been administered.

2.7.3 Third Additional Example—Change in Number of Frames

It has been described that whether medication has been administered is determined on the basis of a video including a predetermined number of image frames or confirmation model input data including a predetermined number of pieces of sub data. However, in some cases, whether medication has been administered needs to be determined for a video including image frames of which the number is different from a predetermined number or for confirmation model input data including pieces of sub data of which the number is different from a predetermined number.

For example, depending on a type of medication administration, the video recording time may vary, and as a result, whether medication has been administered may need to be determined for a video including image frames of which the number is different from a predetermined number or confirmation model input data including pieces of sub data of which the number is different from a predetermined number.

As another example, depending on a user, the video recording time may vary, and as a result, whether medication has been administered may need to be determined for a video including image frames of which the number is different from a predetermined number or confirmation model input data including pieces of sub data of which the number is different from a predetermined number.

First, how the server processes a video including image frames of which the number exceeds a predetermined number or confirmation model input data including pieces of sub data of which the number exceeds a predetermined number will be described.

Figure 41:
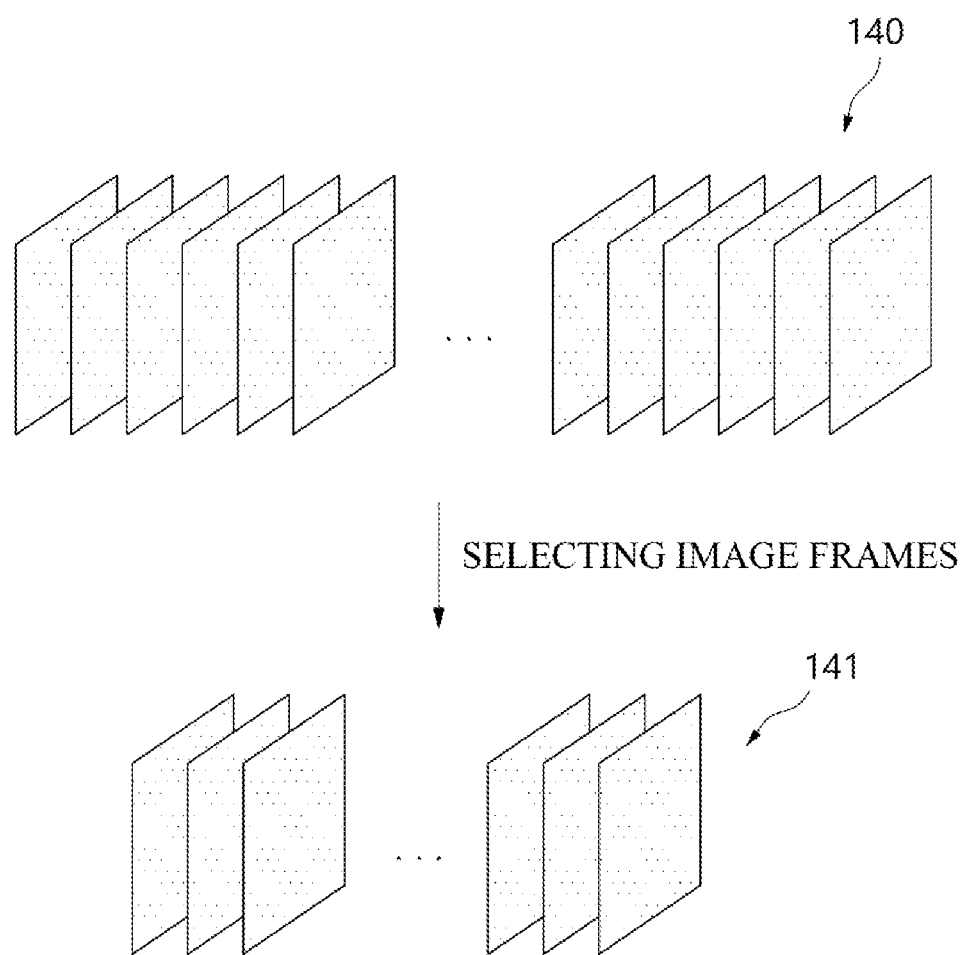
FIG. 41 is a diagram illustrating selection of image frames according to an embodiment.

FIG. 41 is a diagram illustrating selection of image frames according to an embodiment. Referring to FIG. 41, from a video 140 including image frames of which the number exceeds a predetermined number, the server may acquire a video 141 including the predetermine d number of image frames through frame selection.

In some embodiments, frame selection may refer to selecting odd-numbered image frames or even-numbered image frames. For example, in the case of a video including image frames of which the number is twice a predetermine d number, the server may select odd-numbered image frames or even-numbered image frames of the video to generate a video including the predetermined number of image frames. Similarly, in the case of a video including image frames of which the number is n times a predetermined number, the server may select every n-th image frame of the video to generate a video including the predetermined number of image frames.

Alternatively, frame selection may refer to selecting image frames randomly. For example, from a video including image frames of which the number exceeds a predetermined number, the server may select the predetermined number of image frames randomly to generate a video including the predetermined number of image frames.

The description of such frame selection is only an example and is not limited thereto.

Similarly, from confirmation model input data including pieces of sub data of which the number exceeds a predetermine d number, the server may acquire confirmation model input data including a predetermined number of pieces of sub data through sub data selection. The details of frame selection may be applied to sub data selection, so a detailed description thereof will be omitted.

Next, how the server processes a video including image frames of which the number is less than a predetermined number or confirmation model input data including pieces of sub data of which the number is less than the predetermined number will be described.

The server may add image frames to the video including image frames of which the number is less than a predetermine d number so that a video including the predetermine d number of image frames is generated. For example, the added image frames may be added to the former part of the video including image frames of which the number is less than the predetermined number. As another example, the added image frames may be added to the latter part of the video including image frames of which the number is less than the predetermined number. As still another example, the added image frames may be added to the middle part of the video including image frames of which the number is less than the predetermined number. As still another example, the added image frames may be added to a random position of the video including image frames of which the number is less than the predetermine d number.

Depending on a position to which an image frame is added, the accuracies of determining whether medication has been administered may vary. Herein, the positions to which image frames are added which improve the accuracy of determining whether medication has been administered may vary according to a type of model. For example, in the case of using a LSTM model or a model similar thereto, adding an image frame to the former part of the video may increase the accuracy of determining whether medication has been administered, compared to other cases.

The added image frames may have a predetermined pixel value. For example, all pixels of the added image frames may have the same pixel values, but are not limited thereto.

3. Method of Determining Medication Administration Content

The method for determining whether medication has been administered has been described, but in some cases, it may be necessary to determine the medication administration content. Herein, the medication administration content is related to the content of whether medication has been administered, in the broad sense, for example, which pill the user has swallowed, and how many pills the user has swallowed. Hereinafter, swallowing a pill will be mainly described.

Figure 42:
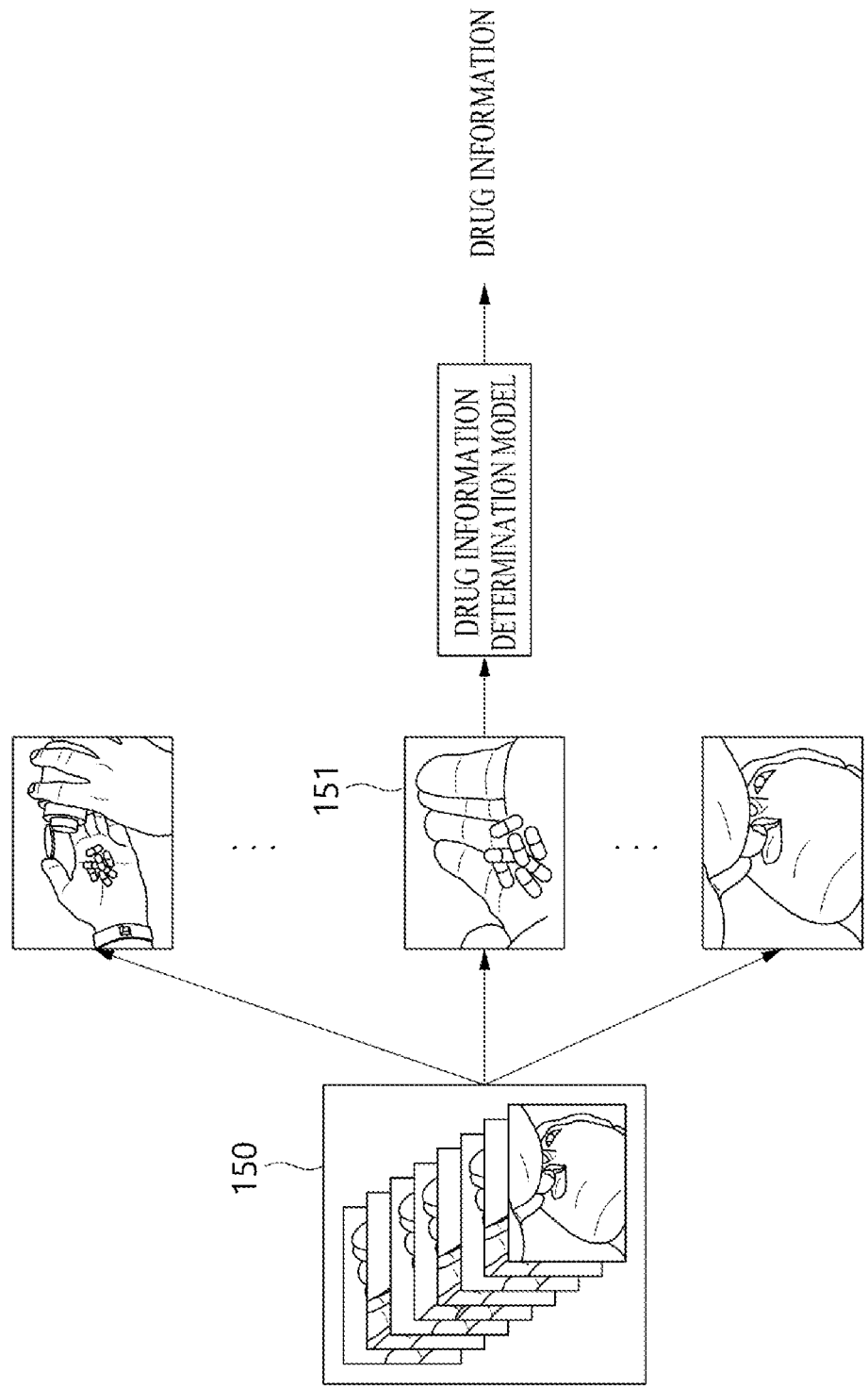
FIG. 42 is a diagram illustrating determination of drug information, in swallowing pills according to an embodiment.

FIG. 42 is a diagram illustrating determination of drug information, in swallowing pills according to an embodiment. The drug information may include the number of pills and types of pills. Referring to FIG. 42, the server may determine the drug information on the basis of an image frame 151 showing a scene in which pills are placed on the palm, among image frames of a video 150. For example, the server may input the image frame 151 showing the scene in which pills are placed on the palm, among the image frames of the video 150, into a drug information determination model to acquire the drug information.

When there are multiple image frames showing the scene in which pills are placed on the palm, the server may determine the drug information on the basis of the image frame corresponding to the latest time among the multiple image frames. Alternatively, the server may determine the drug information on the basis of each of the multiple image frames, and may synthesize the resulting pieces of drug information to determine final drug information.

The server may find the image frame showing the scene in which pills are placed on the palm using a model that is capable of detecting the situation in which pills are placed on the palm. For example, the server may input a video image frame by image frame to the model and may find the image frame showing the scene in which pills are placed on the palm, among all image frames. In the case in which the detection model is trained to detect the situation in which pills are placed on the palm, the detection result of the detection model is checked to find the image frame showing the scene in which pills are placed on the palm, without performing additional calculation using a particular model. In this case, the image frame showing the scene in which pills are placed on the palm may be found remarkably quickly, compared to the case of performing additional calculation using a particular model. In addition, the computational cost may be remarkably reduced.

The model may be realized identically or similarly to the above-described detection model, but is not limited thereto.

The server determining the medication administration content may be the same as the server determining whether medication has been administered. Alternatively, the server determining the medication administration content may be a particular server that is different from the server determining whether medication has been administered.

4. Method of Managing Information Related to Medication Administration

The server may manage various pieces of information related to medication administration. For example, the server may manage a current state of medication administration of the user, whether the user wears a wearable device, and the video recording time of a wearable device. The current state of medication administration may include a video, a result of analyzing a video (for example, a result of determining whether medication has been administered, such as information on whether a video represents medication administration or medication non-administration), a schedule of medication administration of the user, the time of medication administration of the user, and whether the user has administered medication again. The current state of medication administration will be described later in more detail.

The server managing the information related to medication administration may be the same as the server determining whether medication has been administered or determining the medication administration content. Alternatively, the server managing the information related to medication administration may be a particular server for management that is different from the server determining whether medication has been administered or determining the medication administration content.

Hereinafter, a method of managing information related to medication administration will be described in more detail.

4.1 Management of Current State of Medication Administration

The server may manage the current state of medication administration of the user.

The server may store the schedule of medication administration of the user.

The server may store the time of medication administration of the user. The time of medication administration may be determined on the basis of the time when a wearable device generates a video. For example, the time of medication administration may be the time when a wearable device generates a video.

The server may give a notification to the user on the basis of the schedule of medication administration of the user.

For example, near the time when the user is required to administer medication according to the schedule of medication administration, the server may give a notification to the wearable device or the user terminal to induce medication administration of the user.

As another example, the server may determine whether the user has administered medication in excess, and may transmit a result of determination to the wearable device or the user terminal to notify the user that medication has been administered again. Herein, the fact that medication has been administered in excess means that at the determined time, medication has been administered in excess of a predetermined number, for example, the user is supposed to take only one pill, but takes two pills. The server may determine whether the user has administered medication in excess, by comparing the medication administration content of the user and the schedule of medication administration.

The server may check with the user whether medication has been administered. The server may check with the user whether medication has been administered, through the wearable device or the user terminal.

For example, the server may check with the user whether medication has been administered, on the basis of the schedule of medication administration. Near the time when the user is required to administer medication according to the schedule of medication administration, the server may check with the user whether medication has been administered.

As another example, the server may receive a video and check with the user whether medication has been administered. The server may receive a video from the wearable device and check with the user whether medication has been administered.

As still another example, the server may determine whether the user has administered medication, and may check with the user whether medication has been administered. The server may analyze the video, and when it is determined that the user has administered medication, the server checks with the user whether the user has administered medication. Alternatively, regardless of a result of analyzing the video, the server may analyze the video to determine whether medication has been administered, and may check with the user whether medication has been administered.

The server may provide a guardian of the user or a medical staff with information on the current state of medication administration of the user. For example, the server may provide the guardian or the medical staff with at least some among a video, a schedule of medication administration of the user, whether medication has been administered, the time of medication administration, and whether medication has been administered again. In this case, the server storing unit may store identification information on the user of the wearable device in association with identification information on a device of the guardian or medical staff of the user.

When the server determines that the user has administered medication, the server may provide the guardian or the medical staff with information on the current state of medication administration of the user.

When the server determines that the user has not administered medication, the server may provide the guardian or the medical staff with information on the current state of medication administration of the user. For example, when the server determines that the user has not administered medication for a predetermined period, the server may notify the guardian or the medical staff that the user has not administered medication.

4.2 Management of Wearing Wearable Device

The server may manage wearing a wearable device of the user.

The server may check whether the user wears the wearable device, on the basis of information collected by the wearable device. For example, the server may analyze a movement of the wearable device through a motion sensor of the wearable device and may check whether the user wears the wearable device. Specifically, when the wearable device does not move for a predetermined period, the server may determine that the user is not wearing the wearable device.

When the server determines that the user is not wearing the wearable device, the server may give the user a notification through the wearable device or the user terminal to induce the user to wear the wearable device.

The server may check whether the use wears the wearable device properly. An incorrect video may be acquired depending on a direction in which the wearable device is worn. For example, in the case in which the wearable device is a smart watch or a smart band, the wearable device needs to be worn such that the camera unit faces the direction of the user's hand, so that the surroundings of the user's hand are photographed.

The server may analyze a video and check whether the user wears the wearable device properly. For example, when the server determines medication non-administration successively a predetermined number of times or more as a result of analyzing the video, the server may determine that the user wears the wearable device incorrectly. Alternatively, when medication-administration related objects and postures are not detected or are detected in number equal to or less than a predetermine d number as a result of analyzing the video, the server may determine that the user wears the wearable device incorrectly. Alternatively, when it is determine d that an area corresponding to a user's arm in an acquired image frame exceeds a predetermined percentage of the entire area of the image frame, the server may determine that the user wears the wearable device incorrectly.

The server may check whether the camera unit of the wearable device is covered by another object. For example, in the case in which the wearable device is a smart watch or a smart band, the server may check whether the camera unit is covered by a user's sleeve.

The server may analyze a video and check whether the camera unit of the wearable device is covered by another object. For example, when the server determines medication non-administration successively a predetermine d number of times or more as a result of analyzing the video, the server may determine that the camera unit is covered by another object. Alternatively, when medication-administration related objects and postures are not detected or are detected in number equal to or less than a predetermined number as a result of analyzing the video, the server may determine that the camera unit is covered by another object. Alternatively, the server may check whether the camera unit is covered by another object, on the basis of a pixel value of an acquired image frame.

When the server determines that the user wears the wearable device incorrectly, the server may give the user a notification through the wearable device or the user terminal to induce the user to wear the wearable device properly.

When wearing by the user occurs, the wearable device may perform a step of acquiring an image frame or a video and transmitting the same to the server. Accordingly, the server may manage wearing the wearable device of the user on the basis of the received image frame or video.

4.3 Management of Video Recording Time

The server may manage the video recording time.

The server may change the video recording time of the wearable device. For example, the server may lengthen or shorten the video recording time. The server may change the video recording time to optimize the video recording time for each user.

The server may analyze the video and determine whether the video recording time is proper for the user. For example, the server may determine whether the video recording time currently set in the wearable device is proper for the user, by determining what medication administration behavior the last image frame of the video corresponds to.

When the server determines that the video recording time is improper for the user, the server may change the video recording time. For example, when the server determines that the video recording time is short for a specific user, the server may lengthen the video recording time for the specific user. Alternatively, when the server determines that the video recording time is long for a specific user, the server may shorten the video recording time for the specific user.

5. Application to Telemedicine

The details of medication administration described above may be applied to a telemedicine situation.

Telemedicine is a medical behavior performed in places where doctors and patients are distant from each other, which is to determine a patient condition with a communication means and provide appropriate medical treatment. In this telemedicine situation, it may be difficult for a doctor to determine a patient condition, compared to the case in which a patient sees a doctor face to face. Therefore, it may be useful to provide a doctor with information on a patient condition.

FIG. 43 is a diagram illustrating provision of a secondary opinion report as an example of application to telemedicine. The secondary opinion report is a report on a user's health condition. A doctor or a guardian may refer to the secondary opinion report in checking the user's health condition or making a user's health care plan. Through this, a doctor may check the user's health condition or make the user's health care plan without seeing the user face to face. The server may provide a doctor with the secondary opinion report to provide or assist a telemedicine service.

The server may generate the secondary opinion report, considering the degree of medication adherence of the user. For example, the server may generate the secondary opinion report, considering the degree of medication adherence according to previous prescription. Herein, the degree of medication adherence according to the previous prescription may be calculated on the basis of a result of determining whether medication administration for the previous prescription has been performed.

The server may determine the user's health condition to generate the secondary opinion report. The server may determine the user's health condition after medication has been administered and a predetermined time has elapsed, and may generate the secondary opinion report. The predetermined time may vary according to at least one among a user, a type of medication, and a type of medication administration.

To determine the user's health condition, the server may transmit a question about the user's health condition to the wearable device. Examples of the question about a health condition include medication side effects, symptoms and emotions after medication administration, one or more clinical values, and one or more pain values, but are not limited thereto.

To determine the user's health condition after medication has been administered and a predetermined time has elapsed, the server may transmit a question about the health condition to the wearable device after medication has been administered and the predetermined time has elapsed.

The wearable device may acquire a user's answer to the question received from the server. The wearable device may transmit the acquired user's answer to the server. The server may determine the user's health condition on the basis of the acquired user's answer. The server may generate the secondary opinion report on the basis of the determine d user's health condition. The server may provide the generated secondary opinion report to a doctor or a guardian.

The server may determine the user's health condition or generate the secondary opinion report, further considering biometric information of the user. As described above, examples of the biometric information include information on movement, such as the number of steps, as well as a heart rate, blood oxygen saturation, and an electrocardiogram, but are not limited thereto.

The server may determine the user's health condition or generate the secondary opinion report, further considering biometric information before medication administration or biometric information after medication administration or both. For example, the server may determine the user's health condition or generate the secondary opinion report by comparing biometric information before medication administration and biometric information after medication administration.

The server may acquire biometric information of the user through the wearable device. The wearable device may measure biometric information of the user. The wearable device may measure biometric information of the user through the motion sensor, the heart rate sensor, the blood oxygen saturation sensor, and the electrocardiogram sensor of the wearable device. The wearable device may transmit the measured biometric information to the server.

FIG. 43 shows that the server determines the user's health condition through the wearable device, but the user's health condition may be determined through a user terminal, such as a smartphone, a tablet PC, a laptop computer, and desktop computer. In this case, the server may determine the user's health condition by communicating with the user terminal rather than the wearable device. Alternatively, the server may determine the user's health condition through both the wearable device and the user terminal.

In addition, FIG. 43 shows that the server determining whether medication has been administered is the same as the server generating the secondary opinion report, but the server generating the secondary opinion report may be different from the server determining whether medication has been administered.

FIG. 44 is a diagram illustrating provision of a prescription report as another example of application to telemedicine. A doctor or a pharmacist may give the user a prescription with reference to a prescription report. Through this, a doctor or a pharmacist may give the user a prescription without seeing the user face to face. The server may provide a doctor or a pharmacist with the prescription report to provide or assist a telemedicine service.

The server may calculate the degree of medication adherence of the user on the basis of information on prescription. For example, the server may calculate the degree of medication adherence of the user according to first prescription, on the basis of information on the first prescription. The degree of medication adherence of the user according to the first prescription may be calculated on the basis of a result of determining whether medication administration for the first prescription has been performed.

The server may generate the prescription report, considering the degree of medication adherence of the user. For example, the server may generate a prescription report on second prescription, considering to the degree of medication adherence according to the first prescription. Specifically, when the degree of medication adherence according to the first prescription is equal to or greater than a predetermined standard, the server generates a prescription report stating that user is allowed to be given second prescription. Alternatively, when the degree of medication adherence according to the first prescription is less than the predetermined standard, the server generates a prescription report stating that the user is not allowed to be given second prescription.

The server may generate a prescription report, considering schedule of medication administration of the user. For example, according to the schedule of medication administration, when it is estimated that the user has completed medication administration for the first prescription, the server may generate a prescription report. Alternatively, when there is a request for second prescription, the server may generate a prescription report. For example, when there is a request for second prescription from the user, the server may generate a prescription report. Herein, as shown in FIG. 44, the server may receive a request for second prescription from the user through the wearable device, but may receive a request for second prescription from the user through other paths, such as a user terminal. In addition, the server may receive a request for second prescription of the user from a doctor, a pharmacist, or a guardian other than the user.

The server may provide the generated prescription report to a doctor or a pharmacist.

FIG. 44 shows that the server determining whether medication has been administered is the same as the server generating the prescription report, but the server generating the prescription report may be different from the server determining whether medication has been administered.

6. Extension to Health Care

Although medication administration has been mainly described, the details of medication administration may extend to health care. The health care is related to management of a user's health in the broad sense in addition to medication administration, wherein examples of management of a user's health include ingestion and measurement of health information with a measuring device, such as measurement of blood pressure with a sphygmomanometer, measurement of blood glucose with a blood glucose meter. That is, the details of medication administration described in 1. System for Determining Whether Medication Has Been Administered, 2. Method for Determining Whether Medication Has Been Administered, 3. Method of Determining Medication Administration Content, 4. Method of Managing Information Related to Medication Administration, and 5. Application to Telemedicine may be applied to health care, such as measurement of health information with a measuring device, and ingestion.

The system for determining whether medication has been administered may extend to a system for determining whether a health care behavior has been performed. Hereinafter, from the above-described details of the system for whether medication has been administered, the part extending to a system for determining whether a health care behavior has been performed will be mainly described.

The wireless communication device 1000 may be attached to or located near a measuring device (for example, a sphygmomanometer, or a blood glucose meter). Alternatively, the wireless communication device 1000 may be attached to or located near an eating utensil (for example, a spoon, chopsticks, a fork, or a bowl).

The wireless communication device 1000 may collect data of a motion of the measuring device or ambient light or both. Alternatively, the wireless communication device 1000 may collect data of a motion of the eating utensil or ambient light or both.

The wireless communication device 1000 may check whether the user has started a health care behavior using the collected data. For example, the wireless communication device 1000 may check whether the user has started a health information measurement behavior. As another example, the wireless communication device 1000 may check whether the user has started an ingestion behavior. When it is checked that the user has started the health care behavior, the wireless communication device 1000 transmits an activation signal to the outside, such as the wearable device 2000 or the server 3000.

Alternatively, the wireless communication device 1000 may transmit the collected data to the outside, such as the wearable device 2000 or the server 3000.

The wearable device 2000 may communicate with the wireless communication device 1000. The wearable device 2000 may receive, from the wireless communication device 1000, the data of the motion of the measuring device or the ambient light or both. Alternatively, the wearable device 2000 may receive, from the wireless communication device 1000, the data of the motion of the eating utensil or the ambient light or both.

The wearable device 2000 may produce a video. For example, the wearable device 2000 may produce a video related to health care. As a specific example, the wearable device 2000 may produce the video related to measuring health information. As another specific example, the wearable device 2000 may produce a video related to ingestion.

The wearable device 2000 may produce the video on the basis of the data received from the wireless communication device 1000. For example, the wearable device 2000 may produce the video on the basis of the data of the motion of the measuring device or the ambient light or both, or on the basis of the activation signal. As another example, the wearable device 2000 may produce the video on the basis of the data of the motion of the eating utensil or the ambient light or both, or on the basis of the activation signal.

The server 3000 may receive the data of the motion of the measuring device or the ambient light or both from the wireless communication device 1000 or the wearable device 2000 or both. Alternatively, the server 3000 may receive the data of the motion of the eating utensil or the ambient light or both from the wireless communication device 1000 or the wearable device 2000 or both.

The server 3000 may determine whether the health care behavior has been performed. For example, the server 3000 may determine whether the health care behavior has been performed, on the basis of information acquired from the wireless communication device 1000 or the wearable device 2000 or both. As a specific example, the server 3000 may determine whether the health care behavior has been performed, by analyzing the video received from the wearable device 2000.

The method for determining whether medication has been administered may extend to a method for determining whether a health care behavior has been performed. Hereinafter, from the above-described details of the method for whether medication has been administered, the part extending to a method for determining whether a health care behavior has been performed will be mainly described.

The server may determine whether the health care behavior has been performed using the monitoring model. For example, the server may determine whether the measuring device has been used using the monitoring model. As another example, the server may determine whether ingestion has been performed using the monitoring model.

The server may input the video to the monitoring model and determine whether the health care behavior has been performed. In this case, output data of the monitoring model may be a result of determining whether the health care behavior has been performed.

The result of determining whether the health care behavior has been performed which is output from the monitoring model may be an index indicating whether the health care behavior has been performed. That is, output data of the monitoring model may be the index indicating whether the health care behavior has been performed. The server may acquire, using the monitoring model, the index indicating whether the health care behavior has been performed, for the input video. As a non-limiting example, the index may be expressed as a numerical value.

The training video of the monitoring model may include a training video of performance of the health care behavior and a training video of non-performance of the health care behavior.

The monitoring model label data may include: a label corresponding to the training video of performance of the health care behavior and indicating performance of the health care behavior; and a label corresponding to the training video of non-performance of the health care behavior and indicating non-performance of the health care behavior. Alternatively, the monitoring model label data may include: a label indicating the probability that performance of the health care behavior is estimated; and a label indicating the probability that non-performance of the health care behavior is estimated.

The server may determine whether the health care behavior has been performed using the detection model and the confirmation model. For example, the server may deter rune whether the measuring device has been used using the detection model and the confirmation model. As another example, the server may determine whether ingestion has been performed using the detection model and the confirmation model.

The server may detect objects and postures related to health care (hereinafter, referred to as health-care related objects and postures) using the detection model. For example, the server may detect objects and postures related to use of the measuring device (hereinafter, referred to as measuring-device-use objects and postures) using the detection model. As another example, the server may detect objects and postures related to ingestion (hereinafter, referred to as ingestion objects and postures) using the detection model.

The server may input image frames of the video to the detection model and detect health-care related objects and postures included in the image frames. The detection model may output data related to the health-care related objects and postures.

The health-care related objects may include various types of health-care related objects, which are used by the user for the health care behavior. For example, the measuring-device-use objects may include various types of measuring-device-use objects, which are used by the user during use of the measuring device. As a specific example, the measuring-device-use objects may include measuring devices such as a sphygmomanometer, and a blood glucose meter. As another example, the ingestion objects may include various types of ingestion objects, which are used by the user for ingestion. As a specific example, the ingestion objects may include eating utensils, such as a spoon, chopsticks, and a fork.

The health-care related postures may include various types of health-care related postures, such as positioning of the user for the health care behavior. For example, the measuring-device-use postures may include various types of measuring-device-use postures, such as positioning of the user during use of the measuring device. As a specific example, the measuring-device-use postures may include: a posture for holding a measuring-device-use object, such as a posture for holding a measuring device; a posture for using a measuring device; and a posture for opening a measuring device. As another example, the ingestion postures may include various types of ingestion postures, such as positioning of the user for ingestion. As a specific example, the ingestion postures may include a posture for holding food, and a posture for taking food.

The detection model training data may include a training image frame and detection model label data included in the training image frame, wherein the detection model label data is related to the health-care related objects and postures.

The server may determine whether the health care behavior has been performed using the detection result and the confirmation model. For example, the server may determine whether the measuring device has been used using the detection result and the confirmation model. As another example, the server may determine whether ingestion has been performed using the detection result and the confirmation model.

The confirmation model input data, which is input data of the confirmation model, may incorporate whether health-care related objects and postures of a specific class are present in the video. Alternatively, the confirmation model input data may incorporate movements of the health-care related objects and postures of a specific class in the video over time.

Output data of the confirmation model may be a result of determining whether the health care behavior has been performed. For example, output data of the confirmation model may be a result of determining whether the measuring device has been used. As another example, output data of the confirmation model may be a result of determining whether ingestion has been performed.

The result of determining whether the health care behavior has been performed which is output from the confirmation model may be an index indicating whether the health care behavior has been performed. That is, output data of the confirmation model may be the index indicating whether the health care behavior has been performed.

The confirmation model input data for training may include the confirmation model input data for training which represent performance of the health care behavior and the confirmation model input data for training which represent non-performance of the health care behavior.

The confirmation model label data may include a label indicating performance of the health care behavior and a label indicating non-performance of the health care behavior. Alternatively, the confirmation model label data may include: a label indicating the probability that performance of the health care behavior is estimated; and a label indicating the probability that non-performance of the health care behavior is estimated.

The server may determine whether the health care behavior has been performed using the classification model. The server may define a category of the video and determine whether the health care behavior has been performed using the video and the defined category.

Defining a category of the video may refer to determining a type of health care corresponding to the video. For example, the server may define a category of the video by determining which category the video corresponds to among two or more categories corresponding to different types of health care. In this case, examples of the categories include a medication administration category, a blood pressure measurement category, a blood glucose measurement category, and an ingestion category, but are not limited thereto.

A health-care related object and posture may have a category corresponding thereto. Categories of health-care related objects and postures may be determine d depending on types of health care related to the health-care related objects and postures. Health-care related objects and postures related to the same or similar types of health care may correspond to the same category. Health-care related objects and postures related to different types of health care may correspond to different categories. For example, a health-care related object and posture, such as the blood glucose meter, and the posture for holding a blood glucose meter, may correspond to a category related to using a blood glucose meter. A health-care related object and posture, such as the sphygmomanometer, and the posture for holding a sphygmomanometer, may be included in a category related to using a sphygmomanometer. A health-care related object and posture, such as the eating utensil, and the posture for holding food, may be included in the category related to ingestion. The description of such categories of health-care related objects and postures is only an example and is not limited thereto.

The server may determine whether the health care behavior has been performed using a particular monitoring model for each category of the video. Alternatively, the server may determine whether the health care behavior has been performed using a particular detection model and a particular confirmation model for each category of the video.

A main-hand video may be a video of the health care behavior in which the main hand is a subject. A sub-hand video may be a video of the health care behavior in which the sub hand is a subject.

The server may determine whether the health care behavior has been performed using a model trained using both the main-hand video and the sub-hand video.

In addition to using both the main-hand video and the sub-hand video, the server may determine whether the health care behavior has been performed using a model trained to determine whether the health care behavior has been performed, by distinguishing performance of the health care behavior in which the main hand is a subject and performance of the health care behavior in which the sub hand is a subject. In this case, the server does not determine whether health care behavior has been performed, as performance of the health care behavior or non-performance of the health care behavior, but determines whether the health care behavior has been performed, as performance of the health care behavior in which the main hand is a subject, as performance of the health care behavior in which the sub hand is a subject, or as non-performance of the health care behavior.

The method of determining the medication administration content may extend to a method of determining the health care content. Hereinafter, from the above-described details of the method of determining the medication administration content, the part extending to a method of determining the health care content will be mainly described.

The server may determine the health care content. Herein, the health care content is related to the content of whether the health care behavior has been performed, in the broad sense, for example, what the blood pressure or blood glucose level measured by the user is, what kind of food the user has ingested is, and what the amount of food the user has ingested is.

The server may analyze the video and acquire the blood pressure or blood glucose level measured by the user. Alternatively, the server may receive user input and acquire the blood pressure or blood glucose level measured by the user.

The server may analyze the video and acquire the type or amount of food that the user has ingested. Alternatively, the server may receive user input and acquire the type or amount of food that the user has ingested.

The server may manage various pieces of information related to health care. For example, the server may manage the current state of health care of the user. As a specific example, the server may manage a measuring device use schedule of the user. As another specific example, the server may manage an ingestion schedule of the user.

A method according to an embodiment may be realized as program instructions executable by various computer means and may be recorded on a computer-readable recording medium. The computer-readable recording medium may include program instructions, data files, data structures, and the like separately or in combinations. The program instructions recorded on the computer-readable recording medium may be specially designed and configured for the present disclosure or may be well-known to and usable by those skilled in the art of computer software. Examples of the computer-readable recording medium includes: magnetic media such as hard disks, floppy disks, and magnetic tapes; optical media such as CD-ROMs, and DVDs; magneto-optical media such as floptical disks; and hardware devices, such as ROM, RAM, and flash memory, which are particularly structured to store and execute program instructions.

Combinations thereof may also be included, but no limitation thereto is imposed. Examples of the program instructions may include mechanical language codes made by a compiler, as well as high level language codes executable by a computer using an interpreter, etc.

The present disclosure has been described with reference to exemplary embodiments thereof, but is not limited thereto. It will be apparent to those skilled in the art that various changes and modifications thereof may be made within the spirit and scope of the present disclosure. Therefore, it is to be understood that such changes and modifications belong to the scope of the appended claims.

What is claimed is:

1. A method of training a model for determining whether medication is administered using information acquired by a wearable device worn on a user's wrist, which is performed by a computing unit, the method comprising:
    preparing a main-hand training video on which a situation, in which the user administers medication using a main hand as a first subject between the main hand that is a hand wearing the wearable device and a sub hand that is a hand not wearing the wearable device, is recorded;
    preparing a sub-hand training video on which a situation in which the user administers medication using the sub hand as a second subject is recorded;
    preparing a medication non-administration training video on which a situation in which the user does not administer medication is recorded;
    calculating a first output value related to whether medication has been administered using the main-hand training video and the model and updating the model based on a first backpropagation obtained by comparing the first output value with a first medication administration label;
    calculating a second output value related to whether medication has been administered using the sub-hand training video and the model and updating the model based on a second backpropagation obtained by comparing the second output value with a second medication administration label; and
    calculating a third output value related to whether medication has been administered using the medication non-administration training video and the model and updating the model based on a third backpropagation obtained by the third output value with a medication non-administration label to update,
    wherein the first medication administration label indicates medication administration in which the main hand is the first subject, the second medication administration label indicates medication administration in which the sub hand is the second subject, and the medication non-administration label indicates medication non-administration.

2. The method of claim 1, wherein:
    the main-hand training video includes a first image frame including at least a portion of the main hand and a second image frame including at least a portion of the sub hand;
    the sub-hand training video includes a third image frame including at least a portion of the main hand and a fourth image frame including at least a portion of the sub hand; and
    the medication non-administration training video includes a fifth image frame including at least a portion of the main hand and a sixth image frame including at least a portion of the sub hand.

3. The method of claim 2, wherein the model includes a detection model for detecting at least one of a medication-administration-related object and a medication-administration-related posture and a confirmation model for determining whether medication is administered,
    wherein the training method further includes:
    preparing a first label set including a first label which corresponds to the first image frame and indicates the main hand included in the first image frame and a second label which corresponds to the second image frame and indicates the sub hand included in the second image frame;
    preparing a second label set including a third label which corresponds to the third image frame and indicates the main hand included in the third image frame and a fourth label which corresponds to the fourth image frame and indicates the sub hand included in the fourth image frame; and
    preparing a third label set including a fifth label which corresponds to the fifth image frame and indicates the main hand included in the fifth image frame and a sixth label which corresponds to the sixth image frame and indicates the sub hand included in the sixth image frame,
    wherein the updating of the model based on the first backpropagation obtained by comparing the first output value with the first medication administration label includes updating the detection model using the first image frame, the second image frame, and the first label set,
    the updating of the model based on the second backpropagation obtained by comparing the second output value with the second medication administration label includes updating the detection model using the third image frame, the fourth image frame, and the second label set, and
    the updating of the model based on the third backpropagation obtained by comparing the third output value with the medication non-administration label includes updating the detection model using the fifth image frame, the sixth image frame, and the third label set.

4. The method of claim 3, wherein:
    the updating the model based on the first backpropagation obtained by comparing the first output value with a first medication administration label includes updating the confirmation model using main hand output data obtained by inputting the main-hand training video to the detection model and the first medication administration label;
    the updating of the model based on the second backpropagation obtained by comparing the second output value with the second medication administration label includes updating the confirmation model using sub hand output data obtained by inputting the sub-hand training video to the detection model and the second medication administration label; and
    the updating of the model based on the third backpropagation obtained by comparing the third output value with the medication non-administration label includes updating the confirmation model using medication non-administration output data obtained by inputting the medication non-administration training video to the detection model and the medication non-administration label.

5. A method of determining whether medication is administered using information acquired by a wearable device worn on a user's wrist, which is performed by a computing unit, the method comprising:
- receiving a video including a plurality of image frames; and
- determining whether the user administers medication using a model for determining whether medication is administered and the video,
- wherein the model is updated based on a first backpropagation by comparing a first output value related to whether medication is administered that is calculated using a main-hand training video and the model with a first medication administration label, wherein the main-hand training video is a video on which a situation, in which the user administers medication using a main hand as a first subject between the main hand that is a hand wearing the wearable device and a sub hand that is a hand not wearing the wearable device, is recorded,
- wherein the model is updated based on a second backpropagation by comparing a second output value related to whether medication is administered that is calculated using a sub-hand training video and the model with a second medication administration label, wherein the sub-hand training video is a video on which a situation in which the user administers medication using the sub hand as a second subject is recorded, and
- wherein the model is updated based on a third backpropagation by comparing a third output value related to whether medication is administered that is calculated using a medication non-administration training video and the model with a medication non-administration label, wherein the medication non-administration training video is a video on which a situation in which the user does not administer medication is recorded,
- wherein the first medication administration label indicates medication administration in which the main hand is the first subject, the second medication administration label indicates the medication administration in which the sub hand is the second subject, and the medication non-administration label indicates medication non-administration.

6. The method of claim 5, wherein:
- the main-hand training video includes a first image frame including at least a portion of the main hand and a second image frame including at least a portion of the sub hand;
- the sub-hand training video includes a third image frame including at least a portion of the main hand and a fourth image frame including at least a portion of the sub hand; and
- the medication non-administration training video includes a fifth image frame including at least a portion of the main hand and a sixth image frame including at least a portion of the sub hand.

7. The method of claim 6, wherein the model includes a detection model for detecting at least one of a medication-administration-related object and a medication-administration-related posture and a confirmation model for determining whether medication is administered,
- wherein the detection model is updated using the first image frame, the second image frame, and a first label set, wherein the first label set includes a first label which corresponds to the first image frame and indicates the main hand included in the first image frame and a second label which corresponds to the second image frame and indicates the sub hand included in the second image frame,
- wherein the detection model is updated using the third image frame, the fourth image frame, and a second label set, wherein the second label set includes a third label which corresponds to the third image frame and indicates the main hand included in the third image frame and a fourth label which corresponds to the fourth image frame and indicates the sub hand included in the fourth image frame, and
- wherein the detection model is updated using the fifth image frame, the sixth image frame, and a third label set, wherein the third label set includes a fifth label which corresponds to the fifth image frame and indicates the main hand included in the fifth image frame and a sixth label which corresponds to the sixth image frame and indicates the sub hand included in the sixth image frame.

8. The method of claim 7, wherein:
- the confirmation model is updated using main hand output data obtained by inputting the main-hand training video to the detection model and the first medication administration label;
- the confirmation model is updated using sub hand output data obtained by inputting the sub-hand training video to the detection model and the second medication administration label; and
- the confirmation model is updated using medication non-administration output data obtained by inputting the medication non-administration training video to the detection model and the medication non-administration label.

9. A non-transitory computer-readable storage medium on which a computer program for executing the method of claim 1 on a computer is recorded.

10. A non-transitory computer-readable storage medium on which a computer program for executing the method of claim 5 on a computer is recorded.

* * * * *